United States Patent
Wong

(10) Patent No.: US 11,161,890 B2
(45) Date of Patent: Nov. 2, 2021

(54) IL-15-BASED FUSIONS TO IL-7 AND IL-21

(71) Applicant: Altor Bioscience LLC, Miramar, FL (US)

(72) Inventor: Hing C. Wong, Weston, FL (US)

(73) Assignee: Altor Bioscience LLC., Culver City, CA (US)

( * ) Notice: Subject to any disclaimer, the term of this patent is extended or adjusted under 35 U.S.C. 154(b) by 73 days.

(21) Appl. No.: 16/114,870

(22) Filed: Aug. 28, 2018

(65) Prior Publication Data

US 2019/0300591 A1 Oct. 3, 2019

Related U.S. Application Data

(60) Provisional application No. 62/551,218, filed on Aug. 28, 2017.

(51) Int. Cl.

| | |
|---|---|
| C07K 14/54 | (2006.01) |
| C07K 14/715 | (2006.01) |
| A61P 37/04 | (2006.01) |
| A61K 38/20 | (2006.01) |
| A21D 8/04 | (2006.01) |
| C12N 15/81 | (2006.01) |
| A61K 38/00 | (2006.01) |

(52) U.S. Cl.
CPC .......... *C07K 14/5443* (2013.01); *A21D 8/047* (2013.01); *A61K 38/2086* (2013.01); *A61P 37/04* (2018.01); *C07K 14/54* (2013.01); *C07K 14/5418* (2013.01); *C07K 14/7155* (2013.01); *C12N 15/81* (2013.01); *A61K 38/00* (2013.01); *C07K 2319/00* (2013.01); *C07K 2319/02* (2013.01); *C07K 2319/30* (2013.01); *C12Y 302/01002* (2013.01); *C12Y 302/0106* (2013.01); *C12Y 302/01033* (2013.01)

(58) Field of Classification Search
CPC ................................................. C07K 14/5433
See application file for complete search history.

(56) References Cited

U.S. PATENT DOCUMENTS

| | | | |
|---|---|---|---|
| 5,116,964 A | | 5/1992 | Capon et al. |
| 5,541,087 A | | 7/1996 | Lo et al. |
| 5,620,939 A | | 4/1997 | Halasa et al. |
| 8,507,222 B2 | | 8/2013 | Wong et al. |
| 9,428,573 B2 | * | 8/2016 | Wong ..................... C12P 21/00 |
| 9,464,127 B2 | * | 10/2016 | Wong ..................... A61K 38/2086 |
| 10,150,805 B2 | * | 12/2018 | Wong ..................... A61P 35/00 |
| 2010/0303811 A1 | * | 12/2010 | Ochi ..................... A61P 37/04 424/134.1 |
| 2014/0134128 A1 | | 5/2014 | Wong et al. |
| 2017/0020964 A1 | | 1/2017 | Conejo-garcia et al. |

FOREIGN PATENT DOCUMENTS

| | | |
|---|---|---|
| WO | 94/04689 A1 | 3/1994 |
| WO | 94/29350 A2 | 12/1994 |
| WO | 96/32478 A1 | 10/1996 |
| WO | 97/34631 A1 | 9/1997 |
| WO | 2005/046449 A2 | 5/2005 |
| WO | 2012/040323 A2 | 3/2012 |
| WO | 2019/046313 A1 | 3/2019 |

OTHER PUBLICATIONS

Dubois et al., The Journal of Immunology, 2008, vol. 180, pp. 2099-2106).*
Mikayama et al. Proc. Natl. Acad. Sci. USA (1993) vol. 90, p. 10056-10060.*
Voet et al. Biochemistry John Wiley & Sons, Inc., (1990) pp. 126-128 and 228-234.*
Jatiani et al., (Oct. 1, 2010) "Jak/STAT Pathways in Cytokine Signaling and Myeloproliferative Disorders: Approaches for Targeted Therapies", Genes & Cancer, 1(10):979-993.
Kimmel Alanr, (1987) "Identification and Characterization of Specific Clones: Strategy for Confirming the Validity of Presumptive Clones", Methods in Enzymology, 152:507-511.
Kishida et al., (Oct. 2003) "Interleukin (IL)-21 and IL-15 Genetic Transfer Synergistically Augments Therapeutic Antitumor Immunity and Promotes Regression of Metastatic Lymphoma", Molecular Therapy, 8(4):552-558.
Klebanoff et al., (Jul. 5, 2005) "Central Memory Self/tumor-Reactive CD8+ T Cells Confer Superior Antitumor Immunity Compared with Effector Memory T Cells", PNAS, 102(27):9571-9576.
Knorr et al., (2013) "Clinical-Scale Derivation of Natural Killer Cells from Human Pluripotent Stem Cells for Cancer Therapy", Stem Cells Translational Medicine, 2(4):274-283.
Kobayashi et al., (Sep. 1, 1989) "Identification and Purification of Natural Killer Cell Stimulatory Factor (NKSF), a Cytokine with Multiple Biologic Effects on Human Lymphocytes", Journal of Experimental Medicine, 170 (3):827-845.
Kroemer et al., (Oct. 7, 2015) "Natural and Therapy-Induced Immunosurveillance in Breast Cancer", Nature Medicine, 21:1128-1138.
Leonard et al., (2016) "IL-21 Signaling in Immunity", F1000 Research, 5:10 pages.
Manoharan M., (Dec. 10, 1999) "2'-Carbohydrate Modifications in Antisense Oligonucleotide Therapy: Importance of Conformation, Configuration and Conjugation", Biochimica et Biophysica Acta—Gene Structure and Expression, 1489(1):117-139.
Manoussaka et al., (Jan. 1, 1997) "Phenotypic and Functional Characterization of Long-Lived NK Cell Lines of Different Maturational Status Obtained from Mouse Fetal Liver", The Journal of Immunology, 158(1):112-119.
Miller et al., (Apr. 15, 2005) "Successful Adoptive Transfer and in Vivo Expansion of Human Haploidentical NK Cells in Patients with Cancer", Blood, 105(8):3051-3057.

(Continued)

*Primary Examiner* — Prema M Mertz
(74) *Attorney, Agent, or Firm* — Sheridan Ross P.C.

(57) ABSTRACT

The invention features multi-specific fusion protein complexes with one domain comprising IL-15 or a functional variant and a binding domain specific to IL-7 or IL-21.

6 Claims, 54 Drawing Sheets
(36 of 54 Drawing Sheet(s) Filed in Color)
Specification includes a Sequence Listing.

(56) References Cited

OTHER PUBLICATIONS

Moretta et al., (Dec. 1, 1990) "Identification of Four Subsets of Human CD3—CD16+ Natural Killer (NK) Cells by the Expression of Clonally Distributed Functional Surface Molecules: Correlation Between Subset Assignment of NK Clones and Ability to Mediate Specific Alloantigen Recognition", Journal of Experimental Medicine, 172(6):1589-1598.
Moskaug et al., (Sep. 15, 1989) "Translocation of Diphtheria Toxin A—Fragment to the Cytosol Role of The Site of Interfragment Cleavage", Journal of Biological Chemistry, 264(26):15709-15713.
Nayar et al., (2015) "Extending the Lifespan and Efficacies of Immune Cells Used in Adoptive Transfer for Cancer immunotherapies—A Review", OncoImmunology, 4(4):12 pages.
Novellino et al., (Mar. 2005) "A Listing of Human Tumor Antigens Recognized by T Cells: Mar. 2004 Update", Cancer Immunology, Immunotherapy, 54(3):187-207.
Oleksiewicz et al., (Oct. 15, 2012) "Anti-bacterial Monoclonal Antibodies: Back to the Future?", Archives of Biochemistry and Biophysics, 526(2):124-131.
Olsnes et al., (1981) "ChimericToxins", Pharmacology and Therapeutics, 15(3):355-381.
Oshimi K., (Jun. 1996) "Lymphoproliferative Disorders of Natural Killer Cells", International Journal of Hematology, 63(4):279-290. (Abstract Only).
Ouyang et al., (Apr. 11, 2008) "The Biological Functions of T Helper 17 Cell Effector Cytokines in Inflammation", Immunity, 28(4):454-467.
Ovadya et al., (Sep. 13, 2014) "Senescent cells: SASPected drivers of age-related pathologies", Biogerontology, 15:627-642.
Pardoll Drewm, (Mar. 22, 2012) "The Blockade of Immune Checkpoints in Cancer Immunotherapy", Nature Reviews Cancer, 12(4):252-264.
Parkhurst et al., (Oct. 2011) "Adoptive Transfer of Autologous Natural Killer Cells Leads to High Levels of Circulating Natural Killer Cells but Does Not Mediate Tumor Regression", Clinical Cancer Research, 17(19):6287-6297.
Parmiani et al., (Feb. 15, 2007) "Unique Human Tumor Antigens: Immunobiology and Use in Clinical Trials", The Journal of Immunology, 178(4):1975-1979.
Pastan et al., (Dec. 1986) "Immunotoxins", Cell, 47:641-648.
Pastan et al., (1992) "Recombinant Toxins as Novel Therapeutic Agents", Annual Review Biochemistry, 61:331-354.
Rager et al., (Sep. 5, 2011) "Cellular Therapy Following Allogeneic Stem-Cell Transplantation", Therapeutic Advances in Hematology, 2(6):409-428.
Reyburn et al., (Feb. 1997) "Human NK Cells: Their Ligands, Receptors and Functions", Immunological Reviews, 155(1):119-125.
Roddie et al., (Jan. 27, 2011) "Donor Lymphocyte Infusion Following Allogeneic Hematopoietic Stem Cell Transplantation", Expert Opinion on Biological Therapy, 11(4):473-487.
Rubnitz et al., (Feb. 20, 2010) "NKAML: A Pilot Study to Determine the Safety and Feasibility of Haploidentical Natural Killer Cell Transplantation in Childhood Acute Myeloid Leukemia", Journal of Clinical Oncology, 28(6):955-959.
Rueff et al., (Jun. 2014) "Lymphocyte Subset Recovery and Outcome after Autologous Hematopoietic Stem Cell Transplantation for Plasma Cell Myeloma", Biology of Blood and Marrow Transplantation, 20(6):896-899.
Ruggeri et al., (Mar. 15, 2002) "Effectiveness of Donor Natural Killer Cell Alloreactivity in Mismatched Hematopoietic Transplants", Science, 295(5562):2097-2100.
Rukavina et al., (Apr. 30, 2015) "Age-Related Decline of Perforin Expression in Human Cytotoxic T Lymphocytes and Natural Killer Cells", Blood, 92(7):2410-2420.
Sabatino et al., (Jul. 28, 2016) "Generation of clinical-grade CD19-specific CAR-modified CD8+ memory stem cells for the treatment of human B-cell malignancies", Blood, 128(4):519-528.
Sagiv et al., (Jul. 2, 2012) "Granule Exocytosis Mediates Immune Surveillance of Senescent Cells", Oncogene, 32(15):1971-1977.
Sagiv et al., (Feb. 2016) "NKG2D Ligands Mediate Immunosurveillance of Senescent Cells", Aging, 8(2):328-344.
See et al., (Sep. 1997) "The Role of Natural Killer Cells in Viral Infections", Scandinavian Journal of Immunology, 46(3):217-224.
Shah et al., (Oct. 2013) "Antigen Presenting Cell-Mediated Expansion of Human Umbilical Cord Blood Yields Log-Scale Expansion of Natural Killer Cells with Anti-Myeloma Activity", Plos One, 8(10): 9 pages.
Sliwkowski et al., (Sep. 13, 2013) "Antibody Therapeutics in Cancer", Science, 341(6151):1192-1198.
Sommermeyer et al., (Sep. 15, 2015) "Chimeric Antigen Receptor-Modified T Cells Derived from Defined CD8+ and CD4+ Subsets Confer Superior Antitumor Reactivity in Vivo", Leukemia, 30(2):492-500.
Soto-Gamez et al., (May 2017) "Therapeutic Interventions for Aging: The Case of Cellular Senescence", Drug Discovery Today, 22(5):786-795.
Srivastava et al., (2008) "Natural Killer Cell Immunotherapy for Cancer: A New Hope", Cytotherapy, 10(8):775-783.
Takahashi et al., (Jun. 1982) "Structure of Human Immunoglobulin Gamma Genes: Implications for Evolution of a Gene Family", Cell, GenBank Accession No. AAC82527.1 (supplement attached), 29:671-679.
Thaventhiran et al., (2012) "T Cell Co-inhibitory Receptors: Functions and Signalling Mechanisms", Journal of Clinical & Cellular Immunology, 12 pages.
Tomalia Donalda, (1993) "Starburst/Cascade Dendrimers: Fundamental Building Blocks for a New Nanoscopic Chemistry Set", Aldrichimica Acta, 26(4):91-101.
Tong et al., (Mar. 16, 2017) "Adoptive Natural Killer Cell Therapy is Effective in Reducing Pulmonary Metastasis of Ewing Sarcoma", OncoImmunology, 6(4):e1303586.
Toulme Jean-Jacques, (Jan. 1, 2001) "New Candidates for True Antisense", Nature Biotechnology, 19(1):17-18.
Trinchieri et al., (May 1, 1978) "Anti-Viral Activity Induced by Culturing Lymphocytes with Tumor-Derived or Virus-Transformed Cells. Enhancement of Human Natural Killer Cell Activity by Interferon and Antagonistic Inhibition of Susceptibility of Target Cells to Lysis", Journal of Experimental Medicine, 147(5):1314-1333.
Trinchieri et al., (Oct. 1, 1984) "Response of Resting Human Peripheral Blood Natural Killer Cells to Interleukin 2", Journal of Experimental Medicine, 160(4):1147-1169.
Uhlmann E., (Mar. 2000) "Recent Advances in Medicinal Chemistry of Antisense Oligonucleotides", Current Opinion in Drug Discovery & Development, 3(2):203-213.
Urlaub et al., (Jul. 1980) "Isolation of Chinese Hamster Cell Mutants Deficient in Dihydrofolate Reductase Activity", Proceedings of the National Academy of Sciences of the United States of America, 77(7):4216-4220.
Wagner et al., (Jun. 2017) "A Two-Phase Expansion Protocol Combining Interleukin (IL)-15 and IL-21 Improves Natural Killer Cell Proliferation and Cytotoxicity against Rhabdomyosarcoma", Frontier in Immunology, 8:16 pages.
Wahl et al., (1987) "Molecular Hybridization of Immobilized Nucleic Acids: Theoretical Concepts and Practical Considerations", Methods in Enzymology, 152:399-407.
Waldmann, (Aug. 2006) "The Biology of Interleukin-2 and Interleukin-15: Implications for Cancer Therapy and Vaccine Design", Nature Reviews Immunology, 6(8):595-601.
Wang, (2015) "T Cell-Based Targeted Immunotherapies for Patients with Multiple Myeloma", International Journal of Cancer, 136:1751-1768.
Weidle et al., (Jul.-Aug. 2013) "The Emerging Role of New Protein Scaffold-based Agents for Treatment of Cancer", Cancer Genomics and Proteomics, 10(4):155-168.
Whitlow et al., (Apr. 1991) "Single-Chain Fv Proteins and their Fusion Proteins", Methods: A Companion to Methods in Enzymology, 2(2):97-105.
Woll et al., (Jun. 11, 2009) "Human Embryonic Stem Cells Differentiate into a Homogeneous Population of Natural Killer Cells with Potent in Vivo Antitumor Activity", Blood, 113(24):6094-6101.

(56) References Cited

OTHER PUBLICATIONS

Wong et al., (Nov. 1, 2013) "The IL-15-based superagonist ALT-803 promotes the antigen-independent conversion of memory CD8+ T cells into innate-like effector cells with antitumor activity", Oncoimmunology, 2(11):e26442.
Xu et al., (Jun. 14, 2012) "Closely Related T-memory Stem Cells Correlate With in Vivo Expansion of CAR.CD19-T Cells and Are Preserved by IL-7 and IL-15", Blood, 123(24):3750-3759.
Xu et al., (May 15, 2013) "Efficacy and Mechanism-of-Action of a Novel Superagonist Interleukin-15: Interleukin-15 Receptor α/Fc Fusion Complex in Syngeneic Murine Models of Multiple Myeloma", Cancer Research, 73(10):3075-3086.
Zhang et al., (Mar. 2011) "Activating Signals Dominate Inhibitory Signals in CD137L/IL-15 Activated Natural Killer Cells", Journal of Immunotherapy, 34(2):187-195.
ZHU et al., (Sep. 15, 2009) "Novel Human Interleukin-15 Agonists", Journal of Immunology, 183(6):3598-3607.
International Preliminary Report on Patentability received for PCT International Application No. PCT/US18/48365, dated Mar. 12, 2020, 9 pages.
International Search Report and Written Opinion received for PCT Patent International Application No. PCT/US18/48365, dated Jan. 7, 2019, 13 pages.
Altschul et al., (1997) "Gapped BLAST and PSI-BLAST: A New Generation of Protein Database Search Programs", Nucleic Acids Research, 25(17):3389-3402.
Alvarez-Fernabdez et al., (2016) "A Short CD3/CD28 Costimulation Combined with IL-21 Enhance the Generation of Human Memory Stem T Cells for Adoptive Immunotherapy", Journal of Translational Medicine, 14:10 pages.
Baar et al., (Mar. 23, 2017) "Targeted Apoptosis of Senescent Cells Restores Tissue Homeostasis in Response to Chemotoxicity and Aging", Cell, 169(1):132-147.
Bachanova et al., (Jun. 19, 2014) "Clearance of Acute Myeloid Leukemia by Haploidentical Natural Killer Cells is Improved Using IL-2 Diphtheria Toxin Fusion Protein", Blood, 123(25):3855-3863.
Baker et al., (Feb. 11, 2016) "Naturally Occurring p16(Ink4a)-positive Cells Shorten Healthy Lifespan", Nature, 530(7589):184-189.
Baker et al., (May 30, 2008) "Opposing Roles for p16Ink4a and p19Arf in Senescence and Ageing Caused by BubR1 Insufficiency", Nature Cell Biology, 10(7):825-836.
Benton et al., (Apr. 8, 1977) "Screening Agt Recombinant Clones by Hybridization to Single Plaques in Situ", Science, 196(4286):180-182.
Berg et al., (2009) "Clinical Grade Ex Vivo-Expanded Human Natural Killer Cells Upregulate Activating Receptors and Death Receptor Ligands and Have Enhanced Cytolytic Activity against Tumor Cells", Cytotherapy, 11(3):341-355.
Capon et al., (Feb. 9, 1989) "Designing CD4 Immunoadhesins for AIDS Therapy", Nature, 337(6207):525-531.
Cerwenka et al., (Jan. 25, 2016) "Natural Killer Cell Memory in Infection, Inflammation and Cancer", Nature Reviews Immunology, 16(2):112-123.
Chamow et al., (Feb. 1996) "Immunoadhesins: Principles and Applications", Trends Biotechnology, 14:52-60.
Chang et al., (Jan. 2013) "Donor Lymphocyte Infusions for Relapse After Allogeneic Transplantation. When, If and for Whom?", Blood Reviews, 27(1):55-62.
Chirifu et al., (Jul. 22, 2007) "Crystal Structure of the IL-15-IL-15Rα Complex, a Cytokine-Receptor Unit Presented in Trans", Nature Immunology, 8:1001-1007.
Christensen et al., (1998) "A Novel Class of Oligonucleotide Analogues Containing 2'-O,3'-C-Linked [3.2.0] Bicycloarabinonucleoside Monomers: Synthesis, Thermal Affinity Studies, and Molecular Modeling", Journal of the American Chemical Society, 120(22):5458-5463.
Ciccone et al., (Mar. 1, 1992) "Evidence of a Natural Killer (NK) Cell Repertoire for (Allo) Antigen Recognition: Definition of Five Distinct NK-Determined Allospecificities in Humans", Journal of Experimental Medicine, 175(3):709-718.
Ciccone et al., (Jul. 1, 1990) "Specific Recognition of Human CD3-CD16+ Natural Killer Cells Requires the Expression of an Autosomic Recessive Gene on Target Cells", Journal of Experimental Medicine, 172(1):47-52.
Coppe et al., (Feb. 2, 2010) "The Senescence-Associated Secretory Phenotype: The Dark Side of Tumor Suppression", Annual Review of Pathology: Mechanisms of Disease, 5:99-118.
Database Genbank, (Sep. 21, 1994) "Human interleukin 15 (IL15) mRNA, complete cds", Genbank Accession No. U14407.1, 2 pages.
Database Genbank, (Dec. 19, 1995) "Human interleukin-15 receptor alpha chain precursor (IL15RA) mRNA, complete cds", Genbank Accession No. U31628.1, 2 pages.
Database Genbank, (Sep. 14, 1995) "Mus musculus interleukin 15 (IL15) mRNA, complete cds", Genbank Accession No. U14332.1, 2 pages.
Database Genbank, (May 20, 2005) "Mus musculus interleukin 15 receptor, alpha chain, mRNA (cDNA clone IMAGE:4457379), complete cds", Genbank Accession No. BC095982.1, 2 pages.
Davis Markm, (1985) "Molecular Genetics of the T Cell-receptor Beta Chain", Annual Review of Immunology, 3:537-560.
Demaria et al., (2014) "An Essential Role for Senescent Cells in Optimal Wound Healing through Secretion of PDGF-AA", Developmental Cell, 31(6):722-733.
Denman et al., (Jan. 18, 2012) "Membrane-Bound IL-21 Promotes Sustained Ex Vivo Proliferation of Human Natural Killer Cells", Plos One, 7(1):13 pages.
Dimri et al., (Sep. 26, 1995) "A Biomarker That Identifies Senescent Human Cells in Culture and in Aging Skin in Vivo", PNAS, 92(20):9363-9367.
Ellison et al., (Jul. 10, 1982) "The Nucleotide Sequence of a Human Immunoglobulin Cyl Gene", Nucleic Acids Research, 10(13):4071-4079.
Fehninger et al., (Dec. 2016) "Harnessing NK Cell Memory for Cancer Immunotherapy", Trends in Immunology, 37(12):877-888.
Ferrini et al., (Apr. 8, 1997) "Interleukin-15 [*Homo sapiens*]", GenBank Accession No. CAA71044.1, 01 page.
Fleer Reinhard, (Oct. 1992) "Engineering Yeast for High Level Expression", Current Opinion in Biotechnology, 3(5):486-496.
Frankel et al., (Oct. 2000) "Cell Surface Receptor-Targeted Therapy of Acute Myeloid Leukemia: A Review", Cancer Biotherapy & Radiopharmaceuticals, 15(5):459-476.
Freier et al., (1997) "The Ups and Downs of Nucleic Acid Duplex Stability: Structure-Stability Studies on Chemically-Modified DNA:RNA Duplexes", Nucleic Acids Research, 25(22):4429-4443.
Fujisaki et al., (Apr. 21, 2009) "Expansion of Highly Cytotoxic Human Natural Killer Cells for Cancer Cell Therapy", Cancer Research, 69(9):4010-4017.
Fujiyama et al., (2013) "*Homo sapiens* mRNA for IgG H chain, complete cds, clone: 231H5A11H", GenBank Accession No. AB776838.1, 02 pages.
Gao et al., (2015) "Mechanism of Action of IL-7 and Its Potential Applications and Limitations in Cancer Immunotherapy", International Journal of Molecular Sciences, 16(5):10267-10280.
Gattinoni et al., (Jan. 24, 2013) "Moving T Memory Stem Cells to the Clinic", Blood, 121(4):567-568.
Gerber et al., (2009) "Antibody drug-conjugates targeting the tumor vasculature—Current and future developments", mAbs, 1(3):247-253.
Giri et al., (Jun. 15, 1994) "Utilization of the Beta and Gamma Chains of the IL-2 Receptor by the Novel Cytokine IL-15", The EMBO Journal, 13(12):2822-2830.
Golubovskaya et al., (Mar. 15, 2016) "Different Subsets of T Cells, Memory, Effector Functions, and CAR-T Immunotherapy", Cancers (Basel), 8(3):36.
Gomez-Eerland et al., (Oct. 2014) "Manufacture of Gene-Modified Human T-cells With a Memory Stem/Central Memory Phenotype", Human Gene Therapy Methods, 25(5):277-287.
Gong et al., (Dec. 1, 2010) "Ex Vivo Expansion of Natural Killer Cells with High Cytotoxicity by K562 Cells Modified to Co-

(56) References Cited

OTHER PUBLICATIONS

Express Major Histocompatibility Complex Class I Chain-Related Protein A, 4-1BB Ligand, and Interleukin-15", Tissue Antigens, 76(6):467-475.

Graham et al., (Jul. 1977) "Characteristics of a Human Cell Line Transformed by DNA from Human Adenovirus Type 5", Journal of General Virology, 36(1):59-72.

Grunstein et al., (Oct. 1975) "Colony Hybridization: A Method for the Isolation of Cloned DNAs That Contain a Specific Gene", Proceedings of the National Academy of Sciences of the United States of America, 72(10):3961-3965.

Guillerey et al., (Aug. 19, 2016) "Targeting Natural Killer Cells in Cancer Immunotherapy", Nature Immunology, 17:1025-1036.

Guo et al., (2013) "Therapeutic Cancer Vaccines: Past, Present and Future", Advances in Cancer Research, 119:421-475.

Haller et al., (May 1, 1977) "Generation of Natural Killer Cells: An Autonomous Function of the Bone Marrow", Journal of Experimental Medicine, 145(5):1411-1416.

Han et al., (Dec. 2011) "IL-15:IL-15 Receptor Alpha Superagonist Complex: High-Level Co-Expression in Recombinant Mammalian Cells, Purification and Characterization", Cytokine, 56(3):804-810.

Hazeldine et al., (Sep. 2013) "The Impact of Ageing on Natural Killer Cell Function and Potential Consequences for Health in Older Adults", Ageing Research Reviews, 12(4):1069-1078.

Herdewin Piet, (Jul. 8, 2000) "Heterocyclic Modifications of Oligonucleotides and Antisense Technology", Antisense and Nucleic Acid Drug Development, 10(4):297-310.

(1997) "Interleukin-15 [*Homo sapiens*]", Database Nucleotide.

Extend European Search Report for European Patent Application No. 18851494.7, dated Apr. 7, 2021 8 pages.

Official Action for Canadian Patent Application No. 3074635, dated Aug. 13, 2021 7 pages.

\* cited by examiner

Donor A

FIG. 10B  Donor B

FIG. 14A
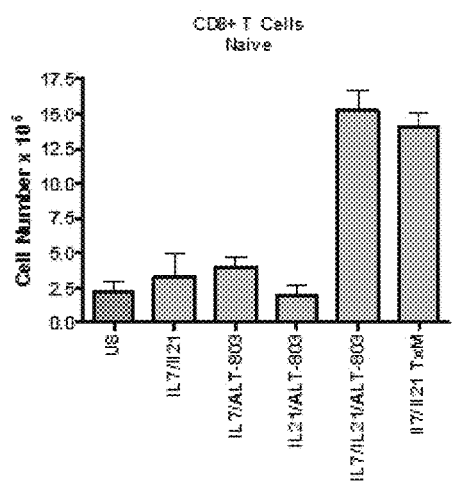
FIG. 14B
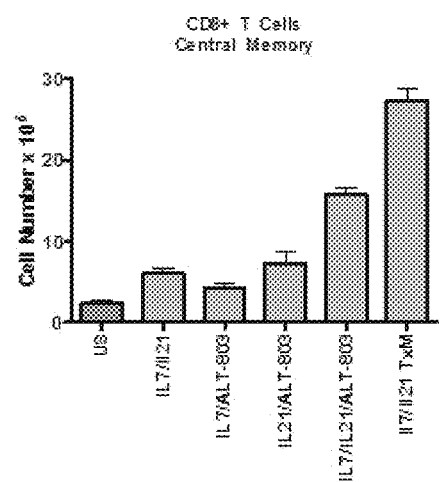
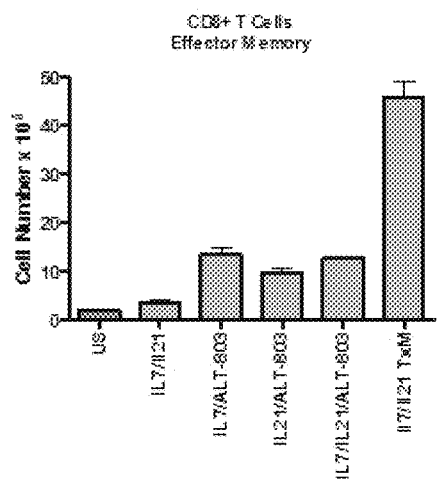
FIG. 14C
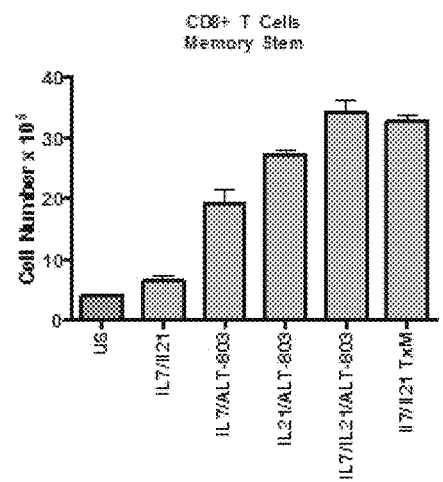
FIG. 14D

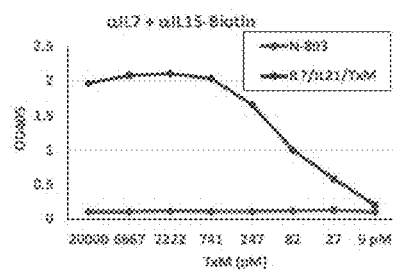
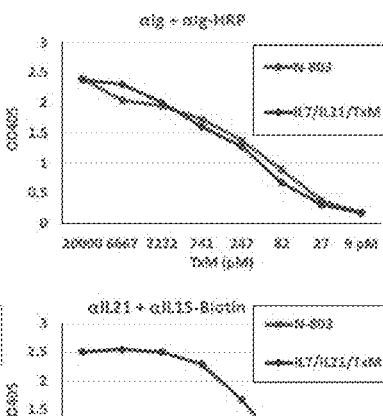
FIG. 22A
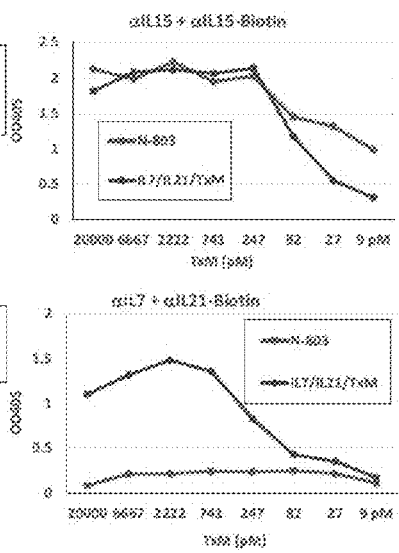
FIG. 22B
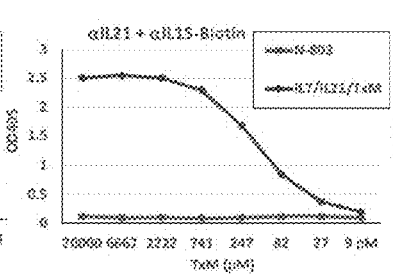
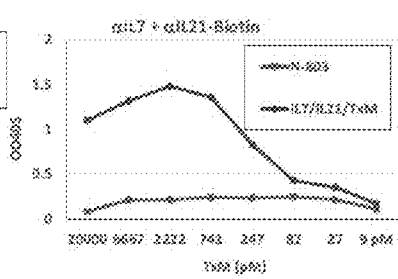
FIG. 22C FIG. 22D FIG. 22E FIG. 27A
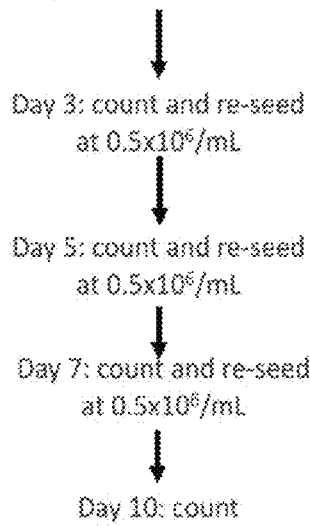
FIG. 27B
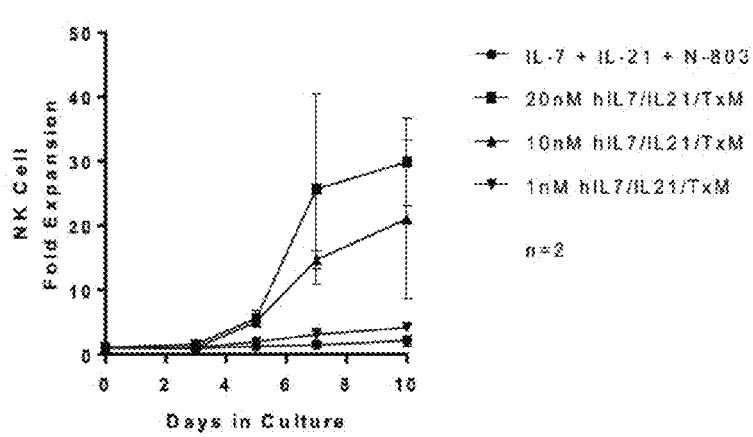
FIG. 28A
FIG. 28B
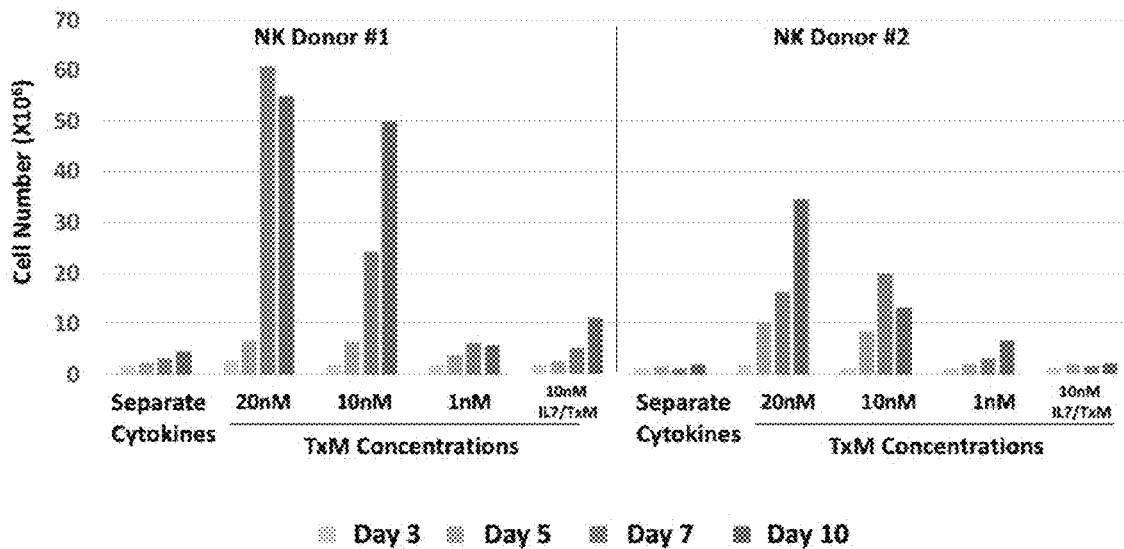

FIG. 33A
FIG. 33B
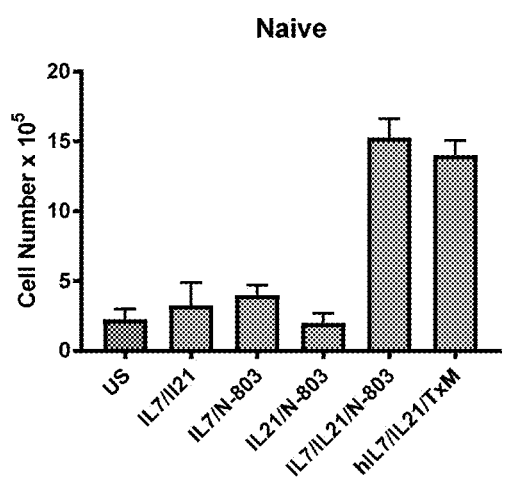
FIG. 33C
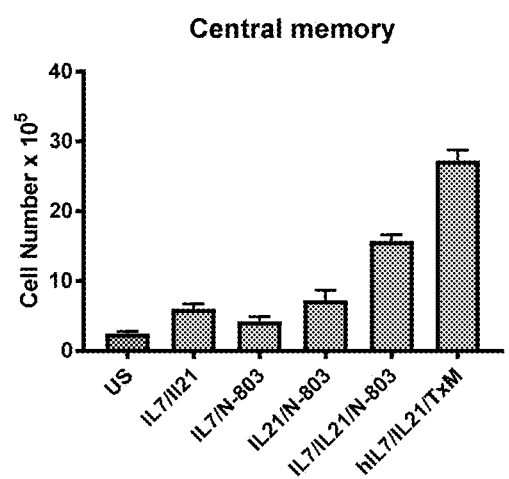
FIG. 33D
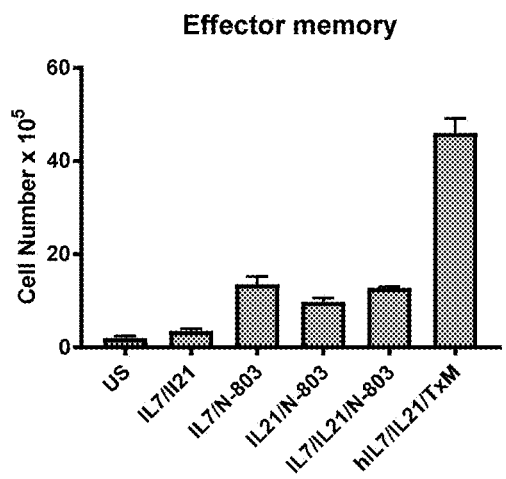
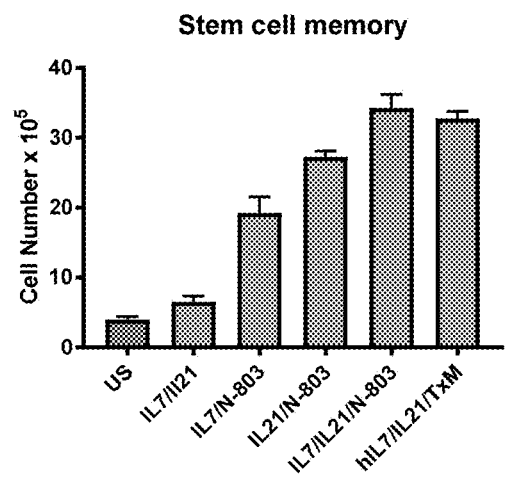

IL-15-BASED FUSIONS TO IL-7 AND IL-21

CROSS REFERENCE TO RELATED APPLICATIONS

This application claims the benefit of U.S. Provisional Application 62/551,218 filed on Aug. 28, 2017, the entire contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 18, 2018, is named 048277-533001US_SL.txt and is 9.51 bytes in size.

FIELD OF THE INVENTION

This invention relates generally to the field of multimeric fusion molecules.

BACKGROUND OF THE INVENTION

Prior to the invention described herein, there was a pressing need to develop new strategies to target various effector molecules to a disease site to provide therapeutic benefit without the side effects associated with non-specific immune activity.

SUMMARY OF THE INVENTION

The invention is based, at least in part, on the surprising discovery that multi-specific interleukin-15 (IL-15)-based protein complexes enhance the stimulation of immune cells and promote their activity against disease cells, thereby resulting in reduction or prevention of disease. These IL-15-based protein complexes also are capable of binding to disease and target antigens. Provided herein are multi-specific IL-15-based protein complexes comprising IL-7 and IL-21 binding domains (FIGS. 1A-1C). Specifically, described herein are protein complexes comprising an IL-15N72D:IL-15RαSu-Ig Fc scaffold fused to IL-7 and IL-21 binding domains.

As described in detail below, when characterized using human immune cells, these complexes exhibit binding and biological activity of each of the IL-15, IL-7 and IL-21 cytokines. Additionally, these complexes induce proliferation and activation of both T cells and natural killer (NK) cells with enhanced production of IFN-γ. Surprisingly, these complexes were capable of inducing immune responses to a greater degree than was observed by the individual cytokines alone or in combination.

As such, the complex as a single molecule binds to and signals via multiple cytokine receptors on NK and T cells to provide the responses previously observed only with a combination of multiple cytokines. Additionally, these complexes comprise the Fc region of Ig molecules, which can form a dimer to provide a soluble multi-polypeptide complex, bind Protein A for the purpose of purification and interact with Fcγ receptors on NK cells and macrophages, thereby providing advantages to the complex that are not present in the combination of individual cytokines. Mammalian cell expression-based methods for making these complexes suitable for large scale production of clinical grade material are described herein. Additional methods for making and using NK and T cells which proliferate following induction by the protein complex of the invention are also provided.

Accordingly, provided is an isolated soluble fusion protein complex comprising at least two soluble proteins. For example, the first protein comprises an IL-15 polypeptide, e.g., a variant IL-15 polypeptide comprising an N72D mutation (IL-15N72D). The second protein comprises a soluble IL-15 receptor alpha sushi-binding domain (IL-15RαSu) fused to an immunoglobulin Fc domain (IL-15RαSu/Fc). A third component of the isolated soluble fusion protein complex comprises a binding domain of IL-7, wherein the IL-7 binding domain is fused to the either the IL-15N72D or the IL-15RαSu/Fc protein. A fourth component of the isolated soluble fusion protein complex comprises a binding domain of IL-21, wherein the IL-21 binding domain is fused to the either the IL-15N72D or the IL-15RαSu/Fc protein. In some cases, the IL-7 and/or IL-21 binding domains are fused to both the IL-15N72D and IL-15RαSu/Fc proteins. In other cases, either the IL-7 or IL-21 binding domain is fused to the IL-15N72D or the IL-15RαSu/Fc proteins and another binding domain is fused to the other protein. An exemplary fusion protein complex comprises an IL-7 polypeptide covalently linked to an IL-15N72D and an IL-21 polypeptide covalently linked to an IL-15RαSu/Fc fusion protein (FIGS. 1A, 1B).

Exemplary first proteins comprise the amino acid sequences set forth in SEQ ID NO: 2 and SEQ ID NO: 4. Exemplary nucleic acid sequences encoding the first protein comprise the sequences set forth in SEQ ID NO: 1 and SEQ ID NO: 3. In one aspect, the nucleic acid sequence(s) further comprises a promoter, translation initiation signal, and leader sequence operably linked to the sequence encoding the fusion protein. Also provided are DNA vectors comprising the nucleic acid sequences described herein. For example, the nucleic acid sequence is in a vector for replication, expression, or both.

Also provided is a soluble fusion protein complex comprising a first soluble fusion protein complex covalently linked to a second soluble fusion protein complex. For example, the soluble fusion protein complexes of the invention are multimerized, e.g., dimerized, trimerized, or otherwise multimerized (e.g., 4 complexes, 5 complexes, etc.). For example, the multimers are homomultimers or heteromultimers. The soluble fusion protein complexes are joined by covalent bonds, e.g., disulfide bonds, chemical cross-linking agents. In some cases, one soluble fusion protein is covalently linked to another soluble fusion protein by a disulfide bond linking the Fc domain of the first soluble protein to the Fc domain of the second soluble protein.

The Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; mouse IgG2A domain, or any combination thereof. Optionally, the Fc domain includes an amino acid change that results in an Fc domain with altered complement or Fc receptor binding properties or altered dimerization or glycosylation profiles. Amino acid changes to produce an Fc domain with altered complement or Fc receptor binding properties or altered dimerization or glycosylation profiles are known in the art. For example, a substitution of leucine residues at positions 234 and 235 of the IgG1 CH2 (numbering based on antibody consensus sequence) (i.e., . . . P E L L G G . . . ) with alanine residues (i.e., . . . P E A A G G . . . ) results in a loss of Fc gamma receptor binding, whereas the substitution of the lysine residue at position 322 of the IgG1 CH2 (numbering based on antibody consensus sequence) (i.e., . . . K C K S L . . . ) with an alanine residue (i.e., . . . K C A S L . . . ) results in a loss of complement activation. In some examples, such mutations are combined.

In some aspects, the IL-7 or IL-21 binding domain is covalently linked to an IL-15 polypeptide (or functional fragment thereof) by a polypeptide linker sequence. Similarly, the IL-7 or IL-21 binding domain is covalently linked to an IL-15Rα polypeptide (or functional fragment thereof) by a polypeptide linker sequence. Optionally, the IL-15Rα polypeptide (or functional fragment thereof) is covalently linked to the Fc domain (or functional fragment thereof) by a polypeptide linker sequence. Each polypeptide linker sequence can be selected independently. Optionally, the polypeptide linker sequences are the same. Alternatively, they are different.

Optionally, the soluble fusion protein complexes of the invention are provided wherein at least one of the soluble fusion proteins comprise one or more binding domain or detectable labels. Such binding domains may comprise antibodies, soluble T cell receptors, ligands, soluble receptor domains or functional fragments thereof. IL-15-based fusion protein complexes comprising such binding domains have been previously described in U.S. Pat. No. 8,492,118, incorporated herein by reference. Detectable labels include, but are not limited to, biotin, streptavidin, an enzyme or catalytically active fragment thereof, a radionuclide, a nanoparticle, a paramagnetic metal ion, or a fluorescent, phosphorescent, or chemiluminescent molecule, or any combination thereof.

The invention provides methods for making the soluble fusion protein complexes of the invention. The method includes the steps of: a) introducing into a first host cell a DNA vector with appropriate control sequences encoding the first protein, b) culturing the first host cell in media under conditions sufficient to express the first protein in the cell or the media; c) purifying the first protein from the host cells or media, d) introducing into a second host cell a DNA vector with appropriate control sequences encoding the second protein, e) culturing the second host cell in media under conditions sufficient to express the second protein in the cell or the media; and f) purifying the second protein from the host cells or media, and g) mixing the first and second proteins under conditions sufficient to allow binding between IL-15 domain of a first protein and the soluble IL-15Rα domain of a second protein to form the soluble fusion protein complex.

In some cases, the method further includes mixing the first and second protein under conditions sufficient to allow formation of a disulfide bond between the polypeptides expressed from the expression vectors.

Alternatively, methods for making soluble fusion protein complexes of the invention are carried out by a) introducing into a host cell a DNA vector with appropriate control sequences encoding the first protein and a DNA vector with appropriate control sequences encoding the second protein, b) culturing the host cell in media under conditions sufficient to express the proteins in the cell or the media and allow association between IL-15 domain of a first protein and the soluble IL-15Rα domain of a second protein to form the soluble fusion protein complex; and c) purifying the soluble fusion protein complex from the host cells or media.

In one aspect, the method further includes mixing the first and second protein under conditions sufficient to allow formation of a disulfide bond between the polypeptides expressed from the expression vectors.

Also provided are methods for making soluble fusion protein complexes comprising a) introducing into a host cell a DNA vector with appropriate control sequences encoding the first and second proteins, b) culturing the host cell in media under conditions sufficient to express the proteins in the cell or the media and allow association between IL-15 domain of a first protein and the soluble IL-15Rα domain of a second protein to form the soluble fusion protein complex, and to allow formation of a disulfide bond between the polypeptides; and c) purifying the soluble fusion protein complex from the host cells or media.

Optionally, the method further includes mixing the first and second protein under conditions sufficient to allow formation of a disulfide bond between the polypeptides expressed from the expression vectors.

In some cases, the method further includes purification of the complex by Protein A affinity chromatography, size exclusion chromatography, ion exchange chromatography and/or other standard methods (including viral inactivation and/or filtration) sufficient to generate a sufficiently pure protein complex suitable for use as a clinical reagent or therapeutic.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15RβγC receptors compared to the native IL-15 polypeptide. Alternatively, the IL-15 variant functions as an IL-15 antagonist as demonstrated by e.g., decreased binding activity for the IL-15RβγC receptors compared to the native IL-15 polypeptide.

Methods of enhancing immune function are carried out by a) contacting a plurality of cells with a soluble fusion protein complex of the invention, wherein the plurality of cells further include immune cells bearing the IL-15R chains recognized by the IL-15 domain, the IL-7R chains recognized by the IL-7 domain or the IL-21R chains recognized by the IL-21 domain, and b) inducing proliferation and activation the immune cells via signaling of the IL-15R, IL-7R or IL-21R. In one aspect, the method of enhancing immune function further includes activation of the immune cells via signaling of a combination of at least two or all of the IL-15R, IL-7R and IL-21R by the soluble fusion protein complex. Exemplary methods for enhancing immune function include inducing proliferation and activation of NK and T cells via signaling of the IL-15R, IL-12R and IL-18R by the soluble fusion protein complex. Such methods include proliferation and activation of NK and T cells resulting in increased interferon gamma (IFN-γ) production.

Methods for killing a target cell are carried out by a) contacting a plurality of cells with a soluble fusion protein complex of the invention, wherein the plurality of cells further include immune cells bearing the IL-15R chains recognized by the IL-15 domain, the IL-7R chains recognized by the IL-7 domain or the IL-21R chains recognized by the IL-21 domain, and the target disease cells, b) inducing proliferation and activation of the immune cells via signaling of the IL-15R, IL-7R or IL-21R; and c) killing the target disease cells by the activated immune cells. In one aspect, the method includes inducing proliferation and activation the immune cells via signaling of a combination of at least two or all of the IL-15R, IL-7R and IL-21R by the soluble fusion protein complex. Exemplary methods include inducing proliferation and activation of NK and T cells via signaling of the IL-15R, IL-7R and IL-21R by the soluble fusion protein complex. Such methods include proliferation and activation of NK and T cells resulting in increased IFN-γ production.

The invention also provides methods for preventing or treating disease in a patient, the method including the steps of: a) mixing immune cells bearing IL-15R chains or checkpoint or signaling molecules with a soluble fusion protein complex of the invention, b) inducing proliferation and activation of the immune cells, c) administering (or adoptively transfer) to the patient the activated immune cells; and d) damaging or killing the disease cells via the activated immune cells sufficient to prevent or treat the disease in the patient. In one aspect, the method includes proliferation and activation the immune cells via signaling of a combination of at least two or all of the IL-15R, IL-7R and IL-21R by the soluble fusion protein complex. Exemplary methods include inducing proliferation and activation of NK and T cells via signaling of the IL-15R, IL-7R and IL-21R by the soluble fusion protein complex. Some aspects of the method include use of NK and T cells expressing chimeric antigen receptors (CAR NK and CAR T cells). In some embodiments of the invention, the patient is pretreated or preconditioned to facilitate engraftment or survival of the adoptively transferred cells. Examples of preconditioning include treatment with cyclophosphamide and fludarabine. Additionally, the patient may be treated with agents that promote activation, survival or persistence of the adoptively transferred cells pre- and/or post-cell transfer. Examples of such treatment include use of IL-2, IL-15, ALT-803 (also interchangeably referred to herein as "N-803") or other immunostimulatory agents. Other therapeutic approaches of known in the field of adoptive cell therapy (i.e., including but not limited to allogeneic, autologous, haploidentical, DLI, stem cell, NK92-based and CAR NK therapies) may also be used in the methods herein.

Also provided are methods for preventing or treating disease in a patient, the method including the steps of: a) administering to the patient a soluble fusion protein complex of the invention; b) inducing proliferation and activation of the immune cells in the patient; and c) damaging or killing the disease cells via the activated immune cells sufficient to prevent or treat the disease in the patient.

Administration of the fusion protein complexes of the invention induces an immune response in a subject. For example, administration of the fusion protein complexes of the invention induces an immune response against cells associated with neoplasia, infectious disease, senescent cell- or age-related diseases or autoimmune disease. In one aspect, the fusion protein complex of the invention increases immune cell proliferation, activation markers, cytotoxicity against target cells, and/or production of pro-inflammatory cytokines.

The invention provides methods of stimulating immune responses in a mammal by administering to the mammal an effective amount of the soluble fusion protein complex of the invention. The invention also provides methods of suppressing immune responses in a mammal by administering to the mammal an effective amount of the soluble fusion protein complex of any one of the invention.

Methods for treating a neoplasia, infectious disease, senescent cell- or age-related diseases or autoimmune disease in a subject in need thereof are carried out by administering to a subject an effective amount of expanded and activated immune cells or a pharmaceutical composition comprising a soluble fusion protein complex described herein. For example, methods for treating solid or hematological malignancies in a subject in need thereof are carried out by administering to a subject an effective amount of NK cells and T cells, and/or CAR NK and CAR T cells expanded ex vivo by the soluble fusion protein complex of the invention, thereby treating the malignancy. Exemplary soluble fusion protein complexes comprise the amino acid sequences set forth in SEQ ID NO: 2 and SEQ ID NO: 4.

Suitable neoplasias for treatment with the methods described herein include a glioblastoma, prostate cancer, acute myeloid leukemia, B-cell neoplasm, multiple myeloma, B-cell lymphoma, B cell non-Hodgkin's lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, prostate cancer, pancreatic cancer, colorectal cancer, ovarian cancer, non-small cell lung carcinoma, and squamous cell head and neck carcinoma.

An exemplary infection for treatment using the methods described herein includes infections with human immunodeficiency virus (HIV) or cytomegalovirus (CMV). The methods described herein are also useful to treat bacterial infections (e.g., gram positive or gram negative bacteria) (See, e.g., Oleksiewicz et al. 2012. Arch Biochem Biophys. 526:124-31, incorporated herein by reference).

Cell therapies of the invention comprise administration of an effective amount of expanded and activated immune cells. For example, an effective amount of expanded and activated NK or T cells is between $1\times10^4$ cells/kg and $1\times10^{10}$ cells/kg, e.g., $1\times10^4$, $1\times10^5$, $1\times10^6$, $1\times10^7$, $1\times10^8$, $1\times10^9$, and $1\times10^{10}$ cells/kg, or such amounts that can be isolated by leukapheresis. Alternatively, expanded immune cells are administered as a fixed dose or based on body surface area (i.e., per $m^2$). Cells can be administered after ex vivo expansion or cryogenically preserved and administered after thawing (and washing as needed).

The pharmaceutical composition comprising a fusion protein complex is administered in an effective amount. For example, an effective amount of the pharmaceutical composition is between about 1 µg/kg and 100 µg/kg, e.g., 1, 5, 10, 15, 20, 25, 30, 35, 40, 45, 50, 55, 60, 65, 70, 75, 80, 85, 90, 95, or 100 µg/kg. Alternatively, TxM complex is administered as a fixed dose or based on body surface area (i.e., per $m^2$).

The adoptively transferred immune cells or pharmaceutical composition comprising the fusion protein complex is administered at least one time per month, e.g., twice per month, once per week, twice per week, once per day, twice per day, every 8 hours, every 4 hours, every 2 hours, or every hour. Suitable modes of administration for the adoptively transferred immune cells include systemic administration, intravenous administration, or local administration. Suitable modes of administration for the pharmaceutical composition include systemic administration, intravenous administration, local administration, subcutaneous administration, intramuscular administration, intratumoral administration, inhalation, and intraperitoneal administration.

In an aspect, the present disclosure provides an isolated soluble fusion protein complex comprising at least two soluble proteins, where the first soluble protein comprises an interleukin-15 (IL-15) polypeptide domain and the second soluble protein comprises a soluble IL-15 receptor alpha sushi-binding domain (IL-15RαSu) fused to an immunoglobulin Fc domain, where one of the first or second soluble protein further comprises an IL-7 binding domain or functional fragment thereof, where one of the first or second soluble protein further comprises an IL-21 binding domain or functional fragment thereof and wherein the IL-15 domain of the first soluble protein binds to the IL-15RαSu domain of the second soluble protein to form a soluble fusion protein complex.

In an embodiment, the IL-15 polypeptide is an IL-15 variant comprising an N72D mutation (IL-15N72D).

In an embodiment, the first soluble protein comprises the amino acid sequence set forth in SEQ ID NO: 2.

In an embodiment, the second soluble protein comprises the amino acid sequence set forth in SEQ ID NO: 4.

In an embodiment, a first soluble fusion protein complex may be covalently linked to a second soluble fusion protein complex.

In an embodiment, the first soluble fusion protein complex is covalently linked to the second soluble fusion protein complex by a disulfide bond linking the Fc domain of the first soluble fusion protein complex to the Fc domain of the second soluble fusion protein complex.

In an embodiment, the first or second soluble protein further comprises a binding domain that recognizes a disease antigen.

In an embodiment, the first or second soluble protein further comprises a binding domain that recognizes an immune checkpoint or signaling molecule.

In an embodiment, the disease antigen is associated with a neoplasia, infectious disease or senescent cell- or age-related disease.

In an embodiment, the first soluble protein is encoded by the nucleic acid sequence set forth in SEQ ID NO: 1.

In an embodiment, the nucleic acid sequence further comprises a promoter, translation initiation signal, and leader sequence operably linked to the sequence encoding the soluble protein.

In an embodiment, the second soluble protein may be encoded by the nucleic acid sequence set forth in SEQ ID NO: 3.

In an embodiment, the nucleic acid sequence further comprises a promoter, translation initiation signal, and leader sequence operably linked to the sequence encoding the soluble protein.

In an embodiment, a DNA vector may comprise any of the above enumerated nucleic acid sequences.

In an embodiment, a method for enhancing immune function, the method comprising: a) contacting a plurality of cells with any of the above soluble fusion protein complexes, where the plurality of cells further comprises immune cells bearing the IL-15R chains recognized by the IL-15 domain, the IL-7R chains recognized by the IL-7 domain and/or the IL-21R chains recognized by the IL-21 domain, and b) inducing proliferation and activation of the immune cells via signaling of the IL-15R, IL-7R and/or IL-21R.

In an aspect, the present disclosure provides a method for killing a target cell, comprising: a) contacting a plurality of cells with any of the above soluble fusion protein complexes, where the plurality of cells further include immune cells bearing the IL-15R chains recognized by the IL-15 domain, the IL-7R chains recognized by the IL-7 domain and/or the IL-21R chains recognized by the IL-21 domain, and the target disease cells, b) inducing proliferation and activation of the immune cells via signaling of the IL-15R, IL-7R and/or IL-21R, and c) killing the target disease cells by the expanded and activated immune cells.

In an embodiment, the target cells are tumor cells or infected cells.

In an aspect, the present disclosure provides a method of enhancing immune responses in a subject, comprising: a) contacting a plurality of cells with any of the above soluble fusion protein complexes, where the plurality of cells further include immune cells bearing the IL-15R chains recognized by the IL-15 domain, the IL-7R chains recognized by the IL-7 domain and/or the IL-21R chains recognized by the IL-21 domain, b) inducing proliferation and activation of the immune cells via signaling of the IL-15R, IL-7R and/or IL-21R, c) administering (or adoptively transfer) to the patient the expanded and activated immune cells; and d) enhancing immune responses in the patient.

In an aspect, the present disclosure provides a method of preventing or treating disease in a patient, comprising: a) contacting a plurality of cells with a soluble fusion protein complex embodied herein, wherein the plurality of cells further includes immune cells bearing the IL-15R chains recognized by the IL-15 domain, the IL-7R chains recognized by the IL-7 domain and/or the IL-21R chains recognized by the IL-21 domain, b) inducing proliferation and activation of the immune cells via signaling of the IL-15R, IL-7R and/or IL-21R, c) administering (or adoptively transfer) an effective amount of the expanded and activated immune cells to the patient, and d) damaging or killing the disease cells via the expanded immune cells sufficient to prevent or treat the disease in the patient.

In certain embodiments, a method of stimulating an immune response in a subject comprises isolating immune cells; contacting the immune cells with a soluble fusion protein complex embodied herein; reinfusing the immune cells into the subject; thereby, stimulating the immune response in a subject. In certain embodiments, the immune cells comprise autologous, haplo-identical, haplotype matched or combinations thereof. In certain embodiments, the immune cells are derived from autologous or allogeneic stem cells. In certain embodiments, the immune cells comprise NK cells, T cells, stem cell memory T cells, activated NK (aNK) cells, chimeric antigen receptor-NK (CAR-NK) cells, chimeric antigen receptor-T (CAR-T) cells, or combinations thereof. In certain embodiments, one or more adjuvants are optionally administered with the soluble fusion protein complexes embodied herein.

In an embodiment, the disease is a neoplasia, infectious disease or senescent cell- or age-related disease.

In an aspect, the present disclosure provides a method of enhancing immune responses in a subject comprising administering to the subject an effective amount of any of the above soluble fusion protein complexes.

In an aspect, the present disclosure provides a method for treating a neoplasia, infectious disease or senescent cell- or age-related disease in a subject in need thereof comprising administering to said subject an effective amount of a pharmaceutical composition comprising any of the above soluble fusion protein complexes, thereby treating said neoplasia, infectious disease or senescent cell- or age-related disease.

In other aspects, a method of treating a subject having a neoplasia, infectious disease or senescent cell- or age-related disease, comprises a) contacting immune cells with any of the above soluble fusion protein complexes, to induce proliferation and activation of the immune cell; b) administering (or adoptively transfer) an effective amount of the activated immune cells to the subject, and c) damaging or killing the disease cells via the activated immune cells sufficient to prevent or treat the disease in the subject.

In an embodiment, the neoplasia is selected from the group consisting of a glioblastoma, prostate cancer, hematological cancer, B-cell neoplasms, multiple myeloma, B-cell lymphoma, B cell non-Hodgkin lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, prostate cancer, pancreatic cancer, colorectal cancer, ovarian cancer, non-small cell lung carcinoma, and squamous cell head and neck carcinoma.

In another embodiment, the senescent cell- or age-related disease is selected from the group consisting of metabolic (obesity, diabetes), neurological (Alzheimer's and Parkinson's diseases), muscle, bone, and cartilage related (sarcopenia, osteoarthritis, kyphosis, herniated discs) or tissue dysfunction related (lung emphysema, cardiovascular and renal diseases, and atherosclerosis) diseases.

In an embodiment, the immune cells are NK cells or cytokine induced memory like (CIML) NK cells.

In another embodiment, the immune cells are T cells or memory stem T cells ($T_{SCM}$).

In an embodiment, the effective amounts of the expanded and activated immune cells are between $1\times10^4$ cells/kg and $1\times10^{10}$ cells/kg.

In an embodiment, the immune cells are administered at least one time per week.

In an embodiment, the effective amount is between about 1 and 100 µg/kg said fusion protein complex.

In an embodiment, the fusion protein complex is administered at least one time per week.

In an embodiment, the fusion protein complex increases immune cell proliferation, activation markers, cytotoxicity against target cells, and/or production of pro-inflammatory cytokines, including IFN-γ.

Preferably, the fusion protein complex increases serum levels of interferon gamma (IFN-γ), and/or stimulates $CD4^+$ and $CD8^+$ T cells and NK cells to kill diseased cells or tumor cells in a subject.

Definitions

Unless defined otherwise, all technical and scientific terms used herein have the meaning commonly understood by a person skilled in the art to which this invention belongs. The terminology used herein is for the purpose of describing particular embodiments only and is not intended to be limiting of the invention.

The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless specifically stated or obvious from context, as used herein, the terms "a", "an", and "the" are understood to be singular or plural. As used in this specification and the appended claims, the term "or" is generally employed in its sense including "and/or" unless the content clearly dictates otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By "agent" is meant a peptide, nucleic acid molecule, or small compound.

By "ALT-803" or "N-803" is meant a complex comprising IL-15N72D noncovalently associated with a dimeric IL-15RαSu/Fc fusion protein and having immune stimulating activity. This complex is also referred to as IL-15 SA. In one embodiment, the IL-15N72D and/or IL-15RαSu/Fc fusion protein comprises one, two, three, four or more amino acid variations relative to a reference sequence.

By "TxM" is meant a complex comprising an IL-15N72D:IL-15RαSu/Fc scaffold linked to a binding domain (FIGS. 1A, 1B). An exemplary TxM is an IL-15N72D:IL-15RαSu complex comprising fusions to IL-7 and IL-21 cytokines.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. "Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, Nucl. Acid. Res., 1997, 25(22), 4429-4443, Toulmé, J. J., Nature Biotechnology 19:17-18 (2001); Manoharan M., Biochemica et Biophysica Acta 1489:117-139(1999); Freier S. M., Nucleic Acid Research, 25:4429-4443 (1997), Uhlman, E., Drug Discovery & Development, 3: 203-213 (2000), Herdewin P., Antisense & Nucleic Acid Drug Dev., 10:297-310 (2000)); 2'-O, 3'-C-linked [3.2.0]bicycloarabinonucleosides (see e.g. N. K Christiensen., et al., J. Am. Chem. Soc., 120: 5458-5463 (1998). Such analogs include synthetic nucleosides designed to enhance binding properties, e.g., duplex or triplex stability, specificity, or the like.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. $F(ab')_2$, Fab', Fab, Fv) capable of binding the epitope, antigen, or antigenic fragment of interest.

As used herein, the terms "associated with," "conjugated," "linked," "attached," and "tethered," when used with respect to two or more moieties, means that the moieties are physically associated or connected with one another, either directly (e.g. covalent bonding) or via one or more additional moieties that serves as a linking agent, to form a structure that is sufficiently stable so that the moieties remain physically associated under the conditions in which the structure is used, e.g., physiological conditions. In some embodiments, a sufficient number of weaker interactions can provide sufficient stability for moieties to remain physically associated under a variety of different conditions.

By "binding to" a molecule is meant having a physicochemical affinity for that molecule.

The term "binding domain" is intended to encompass an antibody, single chain antibody, Fab, Fv, T-cell receptor binding domain, ligand binding domain, receptor binding domain, or other antigen-specific polypeptides known in the art.

As used herein, the term "biologically active moiety" or "effector molecule" is meant a nucleic acid sequence, an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptide or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a fusion complex of the invention and then evaluating whether the fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.

The term "chimeric antigen receptor" or "CAR" as used herein refers to an antigen-binding domain that is fused to an intracellular signaling domain capable of activating or stimulating an immune cell, and in certain embodiments, the CAR also comprises a transmembrane domain. In certain embodiments the CAR's extracellular antigen-binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, the scFv is fused to the transmembrane domain and then to the intracellular signaling domain. "First-generation" CARs include those that solely provide CD3 signals upon antigen binding, "Second-generation" CARs include those that provide both co-stimulation (e.g., CD28 or CD137) and activation (CD3). "Third-generation" CARs include those that provide multiple co-stimulation (e.g. CD28 and CD137) and activation (CD3). A fourth generation of CARs have been described, CAR T cells redirected for cytokine killing (TRUCKS) where the vector containing the CAR construct possesses a cytokine cassette. When the CAR is ligated, the CAR T cell deposits a pro-inflammatory cytokine into the tumor lesion. A CAR-T cell is a T cell that expresses a chimeric antigen receptor. A CAR-NK cell is an NK cell expressing a chimeric antigen receptor. The chimeric antigen receptors (CARs), have an antigen-specific extracellular domain coupled to an intracellular domain that directs the cell to perform a specialized function upon binding of an antigen to the extracellular domain. The terms "artificial T-cell receptor," "chimeric T-cell receptor," and "chimeric immunoreceptor" may each be used interchangeably herein with the term "chimeric antigen receptor." Chimeric antigen receptors are distinguished from other antigen binding agents by their ability to both bind MHC-independent antigen and transduce activation signals via their intracellular domain.

"Detect" refers to identifying the presence, absence or amount of the analyte to be detected.

By "disease" is meant any condition or disorder that damages or interferes with the normal function of a cell, tissue, or organ. Examples of diseases include neoplasia, autoimmune diseases, viral infections, and senescent cell- and age-related disease.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

The term "immune effector cell," as used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, mast cells, and myeloid-derived phagocytes. "Immune effector function or immune effector response," as that term is used herein, refers to a function or response, e.g., of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and co-stimulation are examples of immune effector function or response.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma. As used herein, "obtaining" as in "obtaining an agent" includes synthesizing, purchasing, or otherwise acquiring the agent.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M., and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1%

SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

By "senescent cell-related disease" or age-related disease" is meant a disease or disorder selected from the group consisting of metabolic (obesity, diabetes), neurological (Alzheimer's and Parkinson's diseases), muscle, bone, and cartilage related (sarcopenia, osteoarthritis, kyphosis, herniated discs) or tissue dysfunction related (lung emphysema, cardiovascular and renal diseases, and atherosclerosis) diseases.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "substantially identical" is meant a polypeptide exhibiting at least 85% identity to a reference amino acid sequence (for example, any one of the amino acid sequences described herein). Preferably, such a sequence is at least 90%, more preferably 95% or even 99% identical at the amino acid level to the sequence used for comparison.

Sequence identity is typically measured using sequence analysis software (for example, Sequencher, Gene Codes Corporation, 775 Technology Drive, Ann Arbor, Mich.; Vector NTI, Life Technologies, 3175 Staley Rd. Grand Island, N.Y.). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated. Agents or formulations used in treatment may comprise cells or tissues.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Any genes, gene names, gene products or peptides disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes, nucleic acid sequences or peptides are human.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 10A and 10B are bar graphs showing proliferation of purified human naïve T cells from two donors (donor A, FIG. 10A; donor B, FIG. 10B) following stimulation for various times with hIL7/IL21/TxM fusion protein complex or a combination of recombinant IL-7, IL-21 and ALT-803 (IL-7+IL-21+ALT-803), compared to media control. Proliferation was measured using Presto Blue Assay.

FIGS. 14A-14D depict bar graphs showing the expansion of purified human CD8$^+$ T cell subsets following incubation in media containing hIL7/IL21/TxM fusion protein complex; compared to control media (US), IL-7+IL-21, IL-7+ALT-803, IL-21+ALT-803, or IL-7+IL-21+ALT-803 combinations. Incubation with hIL7/IL21/TxM resulted in expansion of naïve (FIG. 14A), central memory (FIG. 14B), effector memory (FIG. 14C) and memory stem CD8$^+$ (FIG. 14D) T cell subsets compared to media controls and better expansion of central memory and effector memory CD8$^+$ T cell subsets than any other combination of individual cytokines.

FIGS. 22A-22E shows a series of graphs demonstrating the capture and detection of IL-15, IL-7 and IL-21 components in hIL7/IL21/TxM.

FIG. 23A: IL-7 dependent 2E8 cells ($10^5$) were stimulated for 2 days with hIL7/IL21/TxM or IL-7 and cell proliferation was assessed using PrestoBlue. The $EC_{50}$ of IL-7 in hIL7/IL21/TxM is 14 pM. n=4 from 2 experiments. FIG. 23B: Activated natural killer (aNK) cells aNK cells ($2\times10^5$) were stimulated for 40 hours with hIL7/IL21/TxM or N-803 and production of IFNγ was measured by ELISA. n=2 from 1 experiment. FIG. 23C: IL-2/15 dependent 32D-IL2/15Rβ cells ($10^4$) were stimulated for 3 days with hIL7/IL21/TxM or N-803 and cell proliferation was assessed using PrestoBlue. The $EC_{50}$ of IL-15 in hIL7/IL21/TxM is 530 pM. n=4 from 2 experiments.

FIG. 25A: NK cell cytotoxicity. FIG. 25B: NK cell cytotoxicity-associated IFNγ.

FIG. 27A is a schematic representation of an embodiment of the method used to demonstrate that hIL7/IL21/TxM is superior to individual cytokines in expanding purified NK cells. The results obtained are shown as a graph (FIG. 27B).

FIGS. 28A-28B is a series of graphs demonstrating that hIL7/IL21/TxM is superior to individual cytokines in expanding NK cells from human donors. (FIG. 28A—Donor 1; FIG. 28B—Donor 2.) FIG. 29A: Irradiated EBV lymphoblast feeder cells +IL-2 NK expansion.

FIG. 29B: K562-based activated antigen presenting cells (aAPCs) with membrane-bound IL-21 (mbIL21). FIG. 29C: hIL7/IL21/TxM mediated NK cell expansion.

FIGS. 33A-33D depicts a series of graphs demonstrating the expansion of sorted T cell populations following hIL7/IL21/TxM treatment. Sorted $CD8^+$ naïve (FIG. 33A), central memory (FIG. 33B), effector memory (FIG. 33C) and stem cell memory (FIG. 33D) T cells were labeled with CFSE and stimulated with media alone (US) or IL-7/IL-21 (25 ng), IL-7/N-803 (25 ng/144 ng), IL-21/N-803 (25 ng/144 ng), IL-7/IL-21/N-803 (25 ng/25 ng/144 ng), TxM (1.4 mg) in 200 ml total volume in 96 well flat bottom plate in 37° C., 5% $CO_2$.

(FIG. 34A—Naïve; FIG. 34B—Central Memory; FIG. 34C—Effector Memory; FIG. 34D—Stem Cell Memory.)

FIG. 36A: aNK cells ($2\times10^5$) were stimulated for 40 hours with h2*IL21/TxM or N-803 and production of IFNγ was measured by ELISA. n=2 from 1 experiment. FIG. 36B: IL-2/15 dependent 32D-IL2/15Rβ cells ($10^4$) were stimulated for 3 days with h2*IL21/TxM or N-803 and cell proliferation was assessed using PrestoBlue. The $EC_{50}$ of IL-15 in h2*IL21/TxM is 56 pM. n=4 from 2 experiments.

FIG. 38A: IL-7 dependent 2E8 cells ($10^5$) were stimulated for 2 days with h2*IL7(IL15)/TxM or IL-7 and cell proliferation was assessed using PrestoBlue. The $EC_{50}$ of IL-7 in h2*IL7(IL15)/TxM is 13.3 pM. n=4 from 2 experiments.

FIG. 38B: aNK cells ($2\times10^5$) were stimulated for 40 hours with h2*IL7(IL15)/TxM or N-803 and production of IFNγ was measured by ELISA. n=2 from 1 experiment. FIG. 38C: IL-2/15 dependent 32D-IL2/15Rβ cells ($10^4$) were stimulated for 3 days with h2*IL7(IL15)/TxM or N-803 and cell proliferation was assessed using PrestoBlue. The $EC_{50}$ of IL-15 in h2*IL7(IL15)/TxM is 81.3 pM. n=4 from 2 experiments.

DETAILED DESCRIPTION

Figure 1A:
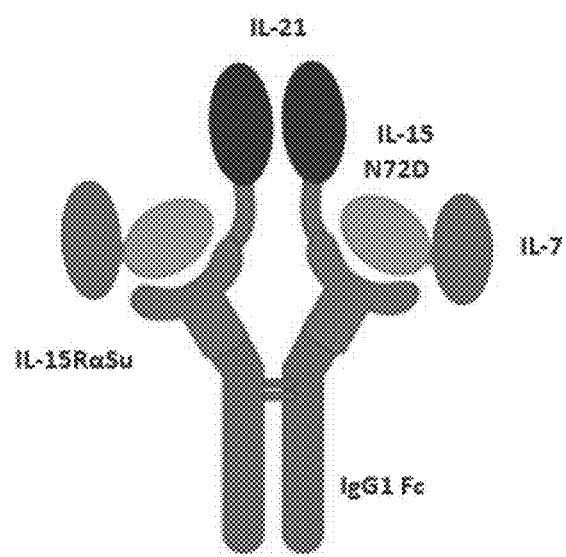
FIG. 1A is a schematic diagram illustrating a TxM fusion protein complex comprising the IL-15N72D:IL-15RαSu/Fc scaffold fused to IL-7 (FIG. 1B) and IL-21 (FIG. 1C) binding domains (IL7-IL15N72D:IL21-IL15RαSuFc). In some cases, the dimeric IL-15RαSu/Fc fusion complexes comprise one or two IL-15N72D fusion protein proteins.

Therapies employing natural killer (NK) cells and T cells have emerged as potential treatments for cancer and viral infections due to the ability of these cells to kill diseased cells and release pro-inflammatory cytokines (See, e.g., Fehniger T A and Cooper M A. Trends Immunol. 2016; 37:877-888; and Cerwenka A and Lanier L L. Nat Rev Immunol. 2016 16:112-23). Of particular interest is adoptive transfer of T cells genetically engineered to express chimeric antigen receptors (CARs) for the induction of tumor-specific immune responses. The effect of cytokines on the phenotype of CAR T cells has been previously described. Stimulation with IL-2, IL-7, and IL-15 led to ex vivo expansion of CAR T cells better than other cytokines or no cytokine presence. (Nayar S., et al., OncoImmunology, 2014; 4:e1002720; Golubovskaya V. and Wu, L. Cancers 2016; 8:236; Sabatino M. et al. Blood. 2016; 128:519-528; Xu Y, et al. Blood. 2014:123:3750-3759; and Gomez-Eerland R, et al. Hum Gene Ther Methods. 2014; 25:277-287).

Recent clinical data suggest that adoptive transfer of less-differentiated T cells, in particular memory stem T cells ($T_{SCM}$), can trigger profound and durable tumor eradication (See, e.g. Klebanoff C A et al. PNAS. 2005; 102(27):9571-9576; and Sommermeyer D, et al. Leukemia. 2016:30(2): 492-500). Due to the low numbers of $T_{SCM}$ cells in circulation, it has been a challenge isolating and producing relevant numbers of clinical grade $T_{SCM}$ cells for adoptive cell therapy (See, e.g. Gattinoni L, et al. Blood. 2013; 121(4):567-568). New reports have shown that generation and expansion of $T_{SCM}$ cells could be achieved ex vivo using CD3/CD28 costimulation and the addition of IL-7, IL-21, and IL-15 throughout the entire culture period (See, e.g. Alvarez-Fernabdez C, et al. J Trans Med. 2016; 14; 214; and Sabatino M et al. Blood. 2016; 128(4):519-528). IL-7 was shown to most effective at increasing proliferation of CAR $T_{SCM}$ cells, and IL-21 supported the expansion of CAR T cells with more stem cell-like phenotype, while IL-2 induced more differentiated CAR T cells. IL-2 and IL-15-treated CAR T cells produced more pro-inflammatory cytokines and exhibited increased antitumor activity in vitro. Additionally, treatment with IL-15 and IL-21 with CAR T cells in vivo increased their tumor cell lysis ability.

IL-7, IL-15, and IL-21, members of the four-helix common gamma chain cytokines, are pivotal in the differentiation, development, maturation, proliferation, and activation of Natural Killers (NK) cells (Waldman T Nature Rev. Immunology 2006; 6:595-601; Leonard W. J. and Wan C.-K. F1000Research 2016; 5:244; Lin J. et al. Anticancer Research 2017; 37:936-968). Adoptive transfer of NK cell is a promising immune therapy against cancer and infectious agents. The major challenge in NK cell therapy is the requirement of a large numbers of highly cytotoxic NK cells. Thus, ex vivo NK cell expansion approaches are being developed and majority of these culturing strategies are based on the use of feeder or accessory cells which need to be removed prior to the clinical application of the final NK cell product (Tong A. A. et al. OncoImmunology 2017; 6:e1303586; Denman C J PLos One 7:e30264; Fujisaki H. et al. Cancer Research 2009; 69:4010-4017). Recently, approaches of using common gamma chain cytokines, particularly IL-15 and IL-21, in the absence of feeder cells for expansion and activation were explored (Wagner J. et al., Frontier in Immunology 2017; 8:676).

Prior to the invention described herein, optimal methods for generating and expanding $T_{SCM}$ cells were not fully elucidated. Strategies employed recombinant human IL-7, human IL-21, and human IL-15, which differ in glycosylation and potentially other post-transcriptional modifications compared to mammalian cell-produced cytokines. The recombinant cytokines may also have different purity and stability and are not generally available as clinical grade material. Additionally, each cytokine is expected to have unique receptor binding, internalization and recycling properties.

Figure 1B:
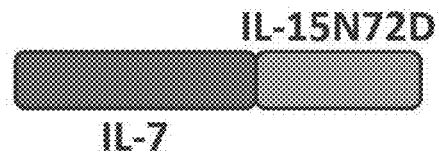
Figure 1C:
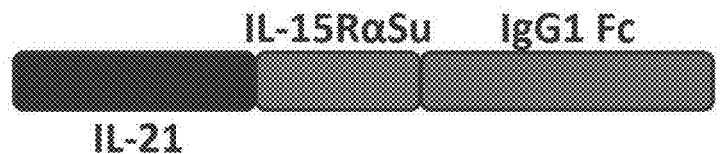

Accordingly, described herein are multi-specific IL-15-based protein complexes comprising IL-7 and IL-21 binding domains (FIGS. 1A, 1B). Specifically, described herein are protein complexes comprising an IL-15N72D:IL-15RαSu-Ig Fc scaffold fused to IL-7 and IL-21 binding domains. When characterized using human immune cells, these complexes exhibit binding and biological activity of each of the IL-15, IL-7 and IL-21 cytokines. Additionally, these complexes act to induce proliferation and activation of T cells with elevated $T_{SCM}$ cell markers, and enhanced production of IFN-γ. These complexes also expand the NK cells ex vivo and the expanded NK cells exhibit augmented cytotoxicity. Thus, the complex as a single molecule binds to and signals via multiple cytokine receptors on T and NK cells to provide the synergistic responses previously only observed with a combination of multiple cytokines. Additionally, these complexes comprise the Fc region of Ig molecules, which can form a dimer to provide a soluble multi-polypeptide complex, bind Protein A for the purpose of purification and interact with Fcγ receptors on NK cells and macrophages for transpresentation, thus providing advantages to the complex that are not present in the combination of individual cytokines. Mammalian cell expression-based methods produce these complexes as glycosylated proteins which may have better activity and/or stability. These methods are also suitable for production of clinical grade material as described herein. Additional methods for inducing proliferation and activation of NK and T cells and generating $T_{SCM}$ cells and CIML NK cells induced by the protein complex of the invention are also provided.

Interleukin-15

Interleukin-15 (IL-15) is an important cytokine for the development, proliferation, and activation of effector NK cells and CD8+ memory T cells. IL-15 binds to the IL-15 receptor α (IL-15Rα) and is presented in trans to the IL-2/IL-15 receptor β-common γ chain (IL-15Rβγ$_c$) complex on effector cells. IL-15 and IL-2 share binding to the IL-15Rβγ$_c$, and signal through STAT3 and STAT5 pathways. However, unlike IL-2, IL-15 does not support maintenance of CD4+CD25+FoxP3+ regulatory T (Treg) cells or induce cell death of activated CD8+ T cells, effects that may have limited the therapeutic activity of IL-2 against multiple myeloma. Additionally, IL-15 is the only cytokine known to provide anti-apoptotic signaling to effector CD8+ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer.

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 superagonist (IL-15N72D) was further improved by the creation of IL-15N72D:IL-15Rα/Fc fusion complex (ALT-803), such that the super agonist complex has at least 25-times the activity of the native cytokine in vivo (Han et al., Cytokine, 56: 804-810, 2011).

IL-15:IL-15Rα Complex

As described above, an IL-15:IL-15Rα fusion protein complex can refer to a complex having IL-15 non-covalently bound to the soluble IL-15Rα domain of the native IL-15Rα. In some cases, the soluble IL-15Rα is covalently linked to a biologically active polypeptide and/or to an IgG Fc domain. The IL-15 can be either IL-15 or IL-15 covalently linked to a second biologically active polypeptide. The crystal structure of the IL-15:IL-15Rα complex is shown in Chirifu et al., 2007 Nat Immunol 8, 1001-1007, incorporated herein by reference.

In various embodiments of the above aspects or any other aspect of the invention delineated herein, the IL-15Rα fusion protein comprises soluble IL-15Rα, e.g., IL-15Rα covalently linked to a biologically active polypeptide (e.g., the heavy chain constant domain of IgG, an Fc domain of the heavy chain constant domain of IgG, or a cytokine). In other embodiments of the invention of the above aspects, IL-15 comprises IL-15, e.g., IL-15 covalently linked to a second biologically active polypeptide, e.g., a cytokine. In other embodiments, purifying the IL-15:IL-15Rα complex from the host cell or media involves capturing the IL-15:IL-15Rα complex on an affinity reagent that specifically binds the IL-15:IL-15Rα fusion protein complex. In other embodiments, the IL-15Rα fusion protein contains an IL-15Rα/Fc fusion protein and the affinity reagent specifically binds the Fc domain. In other embodiments, the affinity reagent is Protein A or Protein G. In other embodiments, the affinity reagent is an antibody. In other embodiments, purifying the IL-15:IL-15Rα complex from the host cell or media comprises ion exchange chromatography. In other embodiments, purifying the IL-15:IL-15Rα complex from the host cell or media comprises size exclusion chromatography.

In other embodiments, the IL-15Rα comprises IL-15RαSushi (IL-15RαSu). In other embodiments, the IL-15 is a variant IL-15 (e.g., IL-15N72D). In other embodiments, the IL-15 binding sites of the IL-15:IL-15Rα complex are fully occupied. In other embodiments, both IL-15 binding sites of the IL-15:IL-15RαSu/Fc complex are fully occupied. In other embodiments, the IL-15:IL-15Rα complex is purified based on the complex charge or size properties. In other embodiments, the fully occupied IL-15N72D:IL-15RαSu/Fc fusion protein complex is purified by anion exchange chromatography based on the complex charge properties. In other embodiments, the fully occupied IL-15N72D:IL-15RαSu/Fc fusion protein complex is purified using a quaternary amine-based resin with binding conditions employing low ionic strength neutral pH buffers and elution conditions employing buffers of increasing ionic strength.

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RβγC receptors compared to the native IL-15 polypeptide. In certain embodiments, the IL-15 variant functions as an IL-15 antagonist as demonstrated by e.g., decreased binding activity for the IL-15RβγC receptors compared to the native IL-15 polypeptide. In certain embodiments, the IL-15 variant has increased binding affinity or a decreased binding activity for the IL-15RβγC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15Rβ and/or IL-15RγC. In certain embodiments, the amino acid change is one or more amino acid substitutions or deletions at position 8, 61, 65, 72, 92, 101, 108, or 111 of the mature human IL-15 sequence. For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

ALT-803 (N-803)

ALT-803 comprises an IL-15 mutant with increased ability to bind IL-2Rβγ and enhanced biological activity (U.S. Pat. No. 8,507,222, incorporated herein by reference). This super-agonist mutant of IL-15 was described in a publication (Zu et al., 2009 J Immunol, 183: 3598-3607, incorporated herein by reference). This IL-15 super-agonist in combination with a soluble IL-15a receptor fusion protein (IL-15RαSu/Fc) results in a protein complex with highly potent IL-15 activity in vitro and in vivo (Han et al., 2011, Cytokine, 56: 804-810; Xu, et al., 2013 Cancer Res. 73:3075-86, Wong, et al., 2013, OncoImmunology 2:e26442). The IL-15 super agonist complex (IL-15N72D: IL-15RαSu/Fc) is referred to as "ALT-803."

Pharmacokinetic analysis indicated that the complex has a half-life of 25 hours following i.v. administration in mice. ALT-803 exhibits impressive anti-tumor activity against aggressive solid and hematological tumor models in immunocompetent mice. It can be administered as a monotherapy using a twice weekly or weekly i.v. dose regimen or as combinatorial therapy with an antibody. The ALT-803 anti-tumor response is also durable. Tumor-bearing mice that were cured after ALT-803 treatment were also highly resistant to re-challenge with the same tumor cells indicating that ALT-803 induces effective immunological memory responses against the re-introduced tumor cells.

IL-7

IL-7 is a cytokine essential for adaptive immune cells development, survival and proliferation. While IL-7 is secreted mainly by stromal cells in the bone marrow and thymus, other immune cells, such as dendritic cells (DCs) can also produce IL-7. The IL-7 receptor is a heterodimer consisting of two chains: IL-7Rα (CD127), which is shared with thymic stromal lymphopoietin (TSLP), and the common γ chain (CD132) which is shared with IL-2, IL-4, IL-9, IL-15 and IL-21. The γ chain is expressed on all hematopoietic cell types, while IL-7Rα is expressed mostly on lymphocytes. IL-7Rα is also found in innate lymphoid cells (ILCs), such as NK cells and gut-associated lymphoid tissue (GALT)-derived LTi cells which are critical in lymphoid organ development and innate immune responses to pathogens. IL-7 can also regulate lymphoid organogenesis by controlling the pool of LTi cells. Another type of IL-7 receptor is a soluble IL-7R, which competes with cell-associated IL-7R to reduce excessive IL-7 consumption by IL-7R-expressing cells and enhances the bioactivity of IL-7 when the cytokine is limited (Gao J et al. Int J Mol Sci. 2015; 16(10267-10280)).

Two main signaling pathways are responsible for the action of IL-7: Jak-Stat and PI3K-Akt. IL-7Rα is associated with the protein tyrosine kinase Janus kinase 1 (Jak1), and the cytosolic tail of the γ chain is associated with Jak3. Binding of IL-7 to its receptor leads to the activation of Jak in the cytosol, phosphorylating Stat proteins. The dimeric phosphorylated Stat proteins subsequently translocate into the nucleus and induce gene expression. Via the Jak3-Stat5 pathway, IL-7 activates the anti-apoptotic genes, Bcl-2 and Mcl-1, and suppresses pro-apoptotic proteins, such as Bax and Bak, which in turn leads to naïve and memory T cells survival. This function is dose-dependent, such that a higher concentration of IL-7 induces thymic emigrant T cell proliferation, while lower concentrations sustain cell survival. By activating the PI3K-Akt pathway, IL-7 downregulates the cell cycle inhibitor p27kip1 to induce the expression of cyclin D1 for cell cycle progression. Moreover, it promotes glucose transporter 1 expression, glucose uptake and mitochondrial integrity to positively regulate cell metabolism and size (Gao J et al. Int J Mol Sci. 2015; 16(10267-10280); and Jatiani S S et al. Genes Cancer. 2010; 1(10):979-993).

IL-21

IL-21 is a pleiotropic cytokine that has both pro- and anti-inflammatory activities and is mainly produced by activated CD4$^+$ and NK T cells. It belongs to the common γ-chain cytokine family and is involved in lymphocyte activation, proliferation, differentiation, and survival. IL-21 functions via heterodimer receptor signaling consisting of specific IL-21R and the common γ-chain receptor. IL-21 signals through the Jak-Stat, PI3K, and MAPK pathways. IL-21 induces strong and continued activation of Stat3, which is critical for T-cell differentiation (Ouyang W, et al. Immunity. 2012; 28(4)454-467).

Together with IL-15 and IL-7, IL-21 promotes expansion of antigen-specific CD8$^+$ T-cell numbers and their effector function, resulting in tumor regression. IL-21 has also been shown to play an important role in the development and survival of both naïve and central memory T cells by the induction of an early differentiation phenotype. Importantly, T cells generated with IL-21 showed a superior antitumor effect in vivo in experimental models.

IL-21 has also been shown to synergize with IL-2, IL-15, and Flt-3L in generating NK cells. It was recently reported that while IL-15 has a role in expanding NK cells, IL-21 induces cytotoxic activity by increased degranulation and secretion of inflammatory cytokines (Wagner J et al. *Front Immunol.* 2017; 8:676).

Antigen-Specific Binding Domains

Antigen-specific binding domains consist of polypeptides that specifically bind to targets on diseased cells. Alternatively, these domains may bind to targets on other cells that support the diseased state, such as targets on stromal cells that support tumor growth or targets on immune cells that support disease-mediated immunosuppression. Antigen-specific binding domains include antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain based proteins, avimers, knottins, fynomers, darpins, affibodies, affilins, monobodies and armadillo repeat protein-based proteins (Weidle, U H, et al. 2013. Cancer Genomics & Proteomics 10: 155-168)) known in the art.

In certain embodiments, the antigen for the antigen-specific binding domain comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the antigen-specific binding domain is capable of binding to an antigen on a tumor cell. Tumor-specific binding domain may be derived from antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, binding domains from approved antibody effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) (Sliwkowski M X, Mellman I. 2013 Science 341:1192) could be used.

Additionally, preferred binding domains of the invention may include various other tumor-specific antibody domains known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch. 14.18 (anti-GD2), ch-TNT (anti-DNA associated antigens), citatuzumab bogatox (anti-EpCAM), cixutumumab (anti-IGF-1 receptor), ivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HERβ), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (antiintegrin av-3), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1 (glycoprotein 75)), fresolimumab (anti-TGF ~), futuximab (anti-EGFR), galiximab (anti-CD80), ganitumab (anti-IGF-1), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGF-RII), imgatuzumab (anti-EGFR), inclacumab (anti-selectin P), indatuximab ravtansine (anti-SDC1), inotuzumab ozogamicin (anti-CD22), intetumumab antiCD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (antiPDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor a-chain), milatuzumab (anti-CD74), minretumomab (anti-TAG-72), mitumomab (anti-GD3 ganglioside), mogamulizumab (antiCCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R a), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MU C1), parsatuzumab (anti-EGFL7), pascolizumab (anti-IL-4), patritumab (anti-HERβ), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-PAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (antiintegrin a5(31), vorsetuzumab mafodotin (anti-CD70), votumumab (antitumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

Other antibody domains or tumor target binding proteins useful in the invention (e.g. TCR domains) include, but are not limited to, those that bind the following antigens (note, the cancer indications indicated represent non-limiting examples): aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), pro static acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like-4), EGFR (various cancers), CTLA4 (melanoma), CXCR4 (CD184, heme-oncology, solid tumors), Endoglin (CD105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR1O (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v\beta 3$, $\alpha p\beta 51$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumor associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178: 1975-9). Examples of these antigens include Cluster of Differentiations (CD4, CDS, CD6, CD7, CDS, CD9, CD1O, CDI 1a, CDI 1b, CDI 1e, CD12w, CD14, CD15, CD16, CDwl7, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvlll, HER-2/neu, idiotype, MAGE A3, p53 nonmutant, NY-ESO-1, GD2, CEA, MelanA/MART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B1, polysialic acid, MYCN, RhoC, TRP-2, GD3, fucosyl GMI, mesothelin, PSCA, MAGE A1, sLe(a), CYPIB I, PLACI, GM3, BORIS, Tn, GloboH, ETV6-AML, NY-BR-1, RGS5, SART3, STn, carbonic anhydrase IX, PAX5, OY-TES 1, sperm protein 17, LCK, HMWMAA, AKAP-4, SSX2, XAGE 1, B7H3, legumain, Tie 2, Page4, VEGFR2, MAD-CT-1, FAP, PDGFR-13, MAD-CT-2, and Fas-related antigen 1.

Additionally, preferred binding domains of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, -influenzae* B, *Treponema pallidum*, Lyme disease spirochetes, *Pseudomonas aeruginosa, Mycobacterium leprae, Brucella abortus,* rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocyticchoriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M. salivarium* and *M. pneumoniae.*

Immune Checkpoint Inhibitor and Immune Agonist Domains

In other embodiments, the binding domain is specific to an immune checkpoint or signaling molecule or its ligand and acts as an inhibitor of immune checkpoint suppressive activity or as an agonist of immune stimulatory activity. Such immune checkpoint and signaling molecules and ligands include PD-1, PD-L1 PD-L2, CTLA-4, CD28, CD80, CD86, B7-H3, B7-H4, B7-H5, ICOS-L, ICOS, BTLA, CD137L, CD137, HVEM, KIR, 4-1BB, OX40L, CD70, CD27, CD47, CIS, OX40, GITR, IDO, TIM3, GAL9, VISTA, CD155, TIGIT, LIGHT, LAIR-1, Siglecs and A2aR (Pardall D M. 2012. Nature Rev Cancer 12:252-264, Thaventhiran T, et al. 2012. J Clin Cell Immunol S 12:004). Additionally, preferred antibody domains of the invention may include ipilimumab and/or tremelimumab (anti-CTLA4), nivolumab, pembrolizumab, pidilizumab, TSR-042, ANBO11, AMP-514 and AMP-224 (a ligand-Fe fusion) (anti-PD1), atezolizumab (MPDL3280A), avelumab (MSB0010718C), durvalumab (MEDI4736), MEDI0680, and BMS-9365569 (anti-PDL1), MEDI6469 (anti-OX40 agonist), BMS-986016, IMP701, IMP731, IMP321 (anti-LAG3) and GITR ligand.

T-Cell Receptors (TCRs)

T cells are a subgroup of cells which together with other immune cell types (polymorphonuclear cells, eosinophils, basophils, mast cells, B-cells, NK cells), constitute the cellular component of the immune system. Under physiological conditions, T cells function in immune surveillance and in the elimination of foreign antigen. However, under pathological conditions, there is compelling evidence that T cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\varepsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain—presumably alpha-helical. Second, all TCR chains have the unusual feature of possessing a charged amino acid within the predicted transmembrane domain. The invariant chains have a single negative charge, conserved between the mouse and human, and the variant chains possess one (TCR-β) or two (TCR-α) positive charges. The transmembrane sequence of TCR-α is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an α and β chain resembling an immunoglobulin variable (V) and constant (C) region. The TCR α chain includes a covalently linked V-α and C-α chain, whereas the β chain includes a V-β chain covalently linked to a C-β chain. The V-α and V-β chains form a pocket or cleft that can bind a superantigen or antigen in the context of a major histocompatibility complex (MHC) (known in humans as an HLA complex). See, Davis *Ann. Rev. of Immunology* 3: 537 (1985); *Fundamental Immunology* 3rd Ed., *W.* Paul Ed. Rsen Press LTD. New York (1993).

The extracellular domains of the TCR chains (αβ or γδ) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of αβ or γδ chains. Such TCRs may include the TCR variable domains or function fragments thereof with or without the TCR constant domains. Soluble TCRs may be heterodimeric or single-chain molecules.

Fc Domain

Protein complexes of the invention may contain an Fc domain. For example, hIL7/IL21/TxM comprises an IL-7/IL-15N72D:IL-21/IL-15RαSu/huIgG1 Fc fusion complex. Fusion proteins that combine the Fc regions of IgG with the domains of another protein, such as various cytokines and soluble receptors have been reported (see, for example, Capon et al., *Nature*, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15Rα covalently linked to the Fc portion of the human heavy chain IgG protein are described herein.

The term "Fc" refers to the fragment crystallizable region which is the constant region of an antibody that interacts with cell surface receptors called Fc receptors and some proteins of the complement system. Such an "Fc" is in dimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins. In some embodiments, Fc domain of the complex is capable of interacting with Fc receptors to mediate antibody-dependent cell-mediated cytotoxicity (ADCC) and/or antibody dependent cellular phagocytosis (ADCP). In other applications, the complex comprises an Fc domain (e.g., IgG4 Fc) that is incapable of effectively mediating ADCC or ADCP.

In some embodiments, the term "Fc variant" refers to a molecule or sequence that is modified from a native Fc, but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that alters one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC) or (8) antibody-dependent cellular phagocytosis (ADCP). Such alterations can increase or decrease any one or more of these Fc properties. Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Linkers

In some cases, the fusion complexes of the invention also include a flexible linker sequence interposed between the IL-15 or IL-15Rα domains and the IL-12 and/or IL-18 binding domain. The linker sequence should allow effective positioning of the polypeptide with respect to the IL-15 or IL-15Rα domains to allow functional activity of both domains.

In certain cases, the soluble fusion protein complex has a linker wherein the first polypeptide is covalently linked to IL-15 (or functional fragment thereof) by polypeptide linker sequence. In other aspects, the soluble fusion protein complex as described herein has a linker wherein the second polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably, about 80 or 90 percent or greater of the linker sequence comprises glycine, alanine or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

Adoptive Cell Therapy

Adoptive cell therapy (ACT) (including allogeneic and autologous hematopoietic stem cell transplantation (HSCT) and recombinant cell (i.e., CAR T) therapies) is the treatment of choice for many malignant disorders (for reviews of HSCT and adoptive cell therapy approaches, see, Rager & Porter, Ther Adv Hematol (2011) 2(6) 409-428; Roddie & Peggs, Expert Opin. Biol. Ther. (2011) 11(4):473-487; Wang et al. Int. J. Cancer: (2015)136, 1751-1768; and Chang, Y. J. and X. J. Huang, Blood Rev, 2013. 27(1): 55-62). Such adoptive cell therapies include, but are not limited to, allogeneic and autologous hematopoietic stem cell transplantation, donor leukocyte (or lymphocyte) infusion (DLI), adoptive transfer of tumor infiltrating lymphocytes, or adoptive transfer of T cells or NK cells (including recombinant cells, i.e., CAR T, CAR NK). Beyond the necessity for donor-derived cells to reconstitute hematopoiesis after radiation and chemotherapy, immunologic reconstitution from transferred cells is important for the elimination of residual tumor cells. The efficacy of ACT as a curative option for malignancies is influenced by a number of factors including the origin, composition and phenotype (lymphocyte subset, activation status) of the donor cells, the underlying disease, the pre-transplant conditioning regimen and post-transplant immune support (i.e., IL-2 therapy) and the graft-versus-tumor (GVT) effect mediated by donor cells within the graft. Additionally, these factors must be balanced against transplant-related mortality, typically arising from the conditioning regimen and/or excessive immune activity of donor cells within the host (i.e., graft-versus-host disease, cytokine release syndrome, etc.).

Approaches utilizing adoptive NK cell therapy have become of significant interest. In patients receiving autologous HSCT, blood NK cell numbers recover very early after the transplant and the levels of NK cells correlate with a positive outcome (Rueff et al., 2014, Biol. Blood Marrow Transplant. 20, 896-899). Although therapeutic strategies with autologous NK cell transfer have had limited success due to a number of factors, adoptive transfer of ex vivo activated allogeneic (or haplo-identical) NK cells has emerged as a promising immunotherapeutic strategy for cancer (Guillerey et al. 2016. Nature Immunol. 17: 1025-1036). The activity of these cells is less likely to be suppressed by self-MHC molecules compared to autologous NK cells. A number of studies have shown that adoptive therapy with haploidentical NK cells to exploit alloreactivity against tumor cells is safe and can mediate significant clinical activity in AML patients. Taking these findings further, recent studies have focused on optimizing ex vivo activation/expansion methods for NK cells or NK precursors (i.e., stem cells) and pre-transplant conditioning and post-transplant immune support strategies; use of NK cell lines or recombinant tumor-targeting NK cells; evaluation of combination therapies with other agents such as therapeutic Ab, immunomodulatory agents (lenalidomide), and anti-KIR and checkpoint Abs. In each case, these strategies could be complemented by the fusion protein complex of the invention, which has the capacity to augment NK cell proliferation and activation. As indicated herein, ex vivo incubation of NK cells with the fusion protein complex of the invention result in induction of CIML NK cell exhibiting elevated activation markers, increased cytotoxicity against tumor cells and enhanced production of IFN-γ. Additionally, the fusion protein complex of the invention is capable of activating human NK cell lines. Moreover, methods are provided for augmenting immune responses and treating neoplasia and infection disease by direct administration of the fusion protein complex of the invention or administration of immune cells activated by the fusion protein complex of the invention.

Natural Killer Cells: One of the major types of circulating mononuclear cells is that of the natural killer, or NK, cell (M. Manoussaka et al., *Journal of Immunology* 158:112-119, 1997). Originally defined based on their ability to kill certain tumors and virus-infected cells, NK cells are now known as one of the components of the early, innate immune system. In addition to their cytotoxic capabilities, NK cells serve as regulators of the immune response by releasing a variety of cytokines. In addition, the generation of complex immune responses is facilitated by the direct interaction of NK cells with other cells via various surface molecules expressed on the NK cells.

NK cells are derived from bone marrow precursors (O. Haller et al., *Journal of Experimental Medicine* 145:1411-1420, 1977). NK cells appear to be closely related to T cells, and the two cell types share many cell surface markers (M. Manoussaka et al., 1997). As noted above, these cell surface markers play a significant role in NK cell activity. For example, murine NK cells express specific antigens on their surfaces, such as asialo GM1, NK1, and NK2 antigens (D. See et al., *Scand. J. Immunol.* 46:217-224, 1997), and the administration of antibodies against these antigens results in depletion of NK cells in vivo (Id.).

Similarly to cytotoxic T lymphocytes (CTL), NK cells exert a cytotoxic effect by lysing a variety of cell types (Srivastava, S., Lundqvist, A. & Childs, R. W. Natural killer cell immunotherapy for cancer: a new hope. *Cytotherapy* 10, 775-783; 2008). These include normal stem cells, infected cells, and transformed cells. The lysis of cells occurs through the action of cytoplasmic granules containing proteases, nucleases, and perforin. Cells that lack MHC class I are also susceptible to NK cell-mediated lysis (H. Reyburn et al., *Immunol. Rev.* 155:119-125, 1997). In addition, NK cells exert cytotoxicity in a non-MHC restricted fashion (E. Ciccione et al., *J. Exp. Med.* 172:47, 1990; A. Moretta et al., *J. Exp. Med.* 172:1589, 1990; and E. Ciccione et al., *J. Exp. Med.* 175:709). NK cells can also lyse cells by antibody-dependent cellular cytotoxicity.

As noted above, NK cells mediate some of their functions through the secretion of cytokines, such as interferon γ (IFN-γ), granulocyte-macrophage colony-stimulating factors (GM-CSFs), tumor necrosis factor α (TNF-α), macrophage colony-stimulating factor (M-CSF), interleukin-3 (IL-3), and IL-8. NK cell cytotoxic activity is regulated through a balance of activating and inhibitory receptors that enables fine-tuned control of cytotoxic activity, preventing cytotoxicity against healthy cells, while maintaining effective cytotoxic capacity against tumor cells. Indeed, multiple studies have demonstrated the safety of adoptive NK cell transfer and clinical anti-cancer effects, highlighting the potential for NK cells as an effective cancer immunotherapy ((Parkhurst, M. R., et al. *Clin Cancer Res* 17, 6287-6297 (2011); Ruggeri, L. et al. *Science* 295, 2097-2100, (2002); Miller, J. S. et al. *Blood* 105, 3051-3057, (2005; Bachanova, V. et al. Blood 123, 3855-3863, (2014); Rubnitz, J. E. et al. *J Clin Oncol* 28, 955-959, (2010)). For example, cytokines including IL-2, IL-12, TNF-α, and IL-1 can induce NK cells to produce cytokines. IFN-α and IL-2 are strong inducers of NK cell cytotoxic activity (G. Trinichieri et al., *Journal of Experimental Medicine* 160:1147-1169, 1984; G. Trinichieri and D. Santoli, *Journal of Experimental Medicine* 147: 1314-1333, 1977). The presence of IL-2 both stimulates and expands NK cells (K. Oshimi, International *Journal of Hematology* 63:279-290, 1996). IL-12 has been shown to induce cytokine production from T and NK cells, and augment NK cell-mediated cytotoxicity (M. Kobayashi et al., *Journal of Experimental Medicine* 170:827-846, 1989).

NK cells are involved in both the resistance to and control of cancer spread. Since the advent of the cancer immune surveillance concept, the adoptive transfer of immune cells, particularly T cells and natural killer (NK) cells, has emerged as a targeted method of harnessing the immune system against cancer (Kroemer, G., Senovilla, L., Galluzzi, L., Andre, F. & Zitvogel, L. Natural and therapy-induced immunosurveillance in breast cancer. *Nat Med* 21, 1128-1138, (2015)). NK cells have garnered immense attention as a promising immunotherapeutic agent for treating cancers. NK cells are critical to the body's first line of defense against cancer due to their natural cytotoxicity against malignant cells (Srivastava, S., et al., *Cytoherapy* 10, 775-783; 2008).

NK cells have been expanded from multiple sources, including peripheral blood and umbilical cord blood (CB) ((Denman, C. J. et al. Membrane-bound IL-21 promotes sustained ex vivo proliferation of human natural killer cells. *PLoS One* 7, e30264, (2012); Knorr, D. A. et al. Clinical-scale derivation of natural killer cells from human pluripotent stem cells for cancer therapy. *Stem Cells Transl Med* 2, 274-283, (2013); Shah, N. et al. Antigen presenting cell-mediated expansion of human umbilical cord blood yields log-scale expansion of natural killer cells with anti-myeloma activity. *PLoS One* 8, e76781, (2013); Wol, P. S. et al. Human embryonic stem cells differentiate into a homogeneous population of natural killer cells with potent in vivo antitumor activity. *Blood* 113, 6094-6101, (2009)). Ex vivo NK cell expansion methods have been developed using cytokines in combination with artificial antigen-presenting cells (aAPCs) as feeder cells ((Denman, C. J. et al. *PLoS One* 7, e30264, (2012); Berg, M. et al. Cytotherapy 11, 341-355, (2009); Gong, W. et al. Tissue Antigens 76, 467-475, (2010); Zhang, H. et al., *J Immunother* 34, 187-195, (2011)).

Cytokine-Based Therapies in Senescent Cell- and Aging-Related Pathologies

Damaged cells undergo either apoptosis or senescence. Senescent cells prevent their own proliferation and secrete signaling molecules—a phenomenon known as the senescence-associated secretory phenotype (SASP) (Coppe J. P. et al., 2010 Annu Rev Pathol 5:99-118). It is proposed that the SASP is to restore tissue function by stimulating less-damaged neighboring cells to engage tissue repair by attracting immune cells (Demaria M., et al., 2014 Dev. Cell 31:722-733). These immune cells eliminate the senescent cells to turn off SASP-mediated signals. When damage exceeds repair capacity or immune cells become unresponsive to effects of the SASP, the aberrant accumulation of senescent cells occurs. As a result, senescent cells accumulate in aged and/or damaged organs and aggravate tissue dysfunction (Ovadya Y. and Krizhanovsky V. et al., 2014 Biogerontology 15:627-642). The elimination of senescent cells has been shown to increase healthy lifespan and reduce the severity of age-related diseases in mice (Baar M. P. et al., 2017 Cell 169:132-147; Baker D J 2016 530:184-189).

Thus, physiological aging is associated with the appearance of senescent cells. Evidence suggests that senescent cells compromise tissue homeostasis and function, and their accumulation contributes to the development of age-associated pathologies (Baker D J et al., 2008 Nat Cell Biol 10:825-836; Baker D J et al., 2016, 530:184-189). In addition to a shorten life span, senescent cells are associated with pathologies include metabolic (obesity, diabetes), neurological (Alzheimer's and Parkinson's diseases), muscle, bone, and cartilage related (sarcopenia, osteoarthritis, kyphosis, herniated discs) or tissue dysfunction related (lung emphysema, cardiovascular and renal diseases, and atherosclerosis) diseases. Studies have shown that the innate and adaptive immune systems are involved in the recognition and elimination of senescent cells (Soto-Gamez A. and Demaria M., 2017 Drug Discovery Today 22:786-795; Hazeldine J. and Lord, J. M., 2013 Aging Research Reviews 12:1069-1078). For instance, NK cells were demonstrated to eliminate senescent cells via the granule exocytosis pathway. Therefore, augmenting these responses may increase natural mechanisms of senescence surveillance and reduce senescent cell-associated pathologies. It has also been suggested that the age-related decline in perforin-mediated NK cell cytotoxicity is responsible in part for the increased frequency of senescent cells in aged tissue (Rukavina D. et al., *Blood* 92:2410-2420; Sagiv A. et al. 2012 Oncogene 1-7). In liver fibrosis, the accumulated of senescent activated stellate cells is increased in mice lacking NKG2D receptor, the major activating receptor of NK cells, leading to increased fibrosis (Sagiv A. et al., 2016 Aging 8:328-344).

The IL-7/IL-21/TxM complexes of the invention have been demonstrated to have potent activity to enhance the cytotoxicity of both the innate and adaptive immune cells including NK and T cells. As disclosed herein, the IL-7/IL-21/TxM complexes are expected to activate and/or maintain immune responses against senescent cells and to have potential applications as anti-aging therapeutic agents. As indicated, the IL-7/IL-21/TxM complexes have advantages over individual cytokines in providing more potent immune stimulation to both NK and T cells. In addition, immune cells stimulated ex vivo by IL-7/IL-21/TxM complexes could be used in adoptive cell transplant for treatment of senescent cell- and/or age-related diseases. Such therapies could be adoptive NK or T cell therapies. Administration of IL-7/IL-21/TxM complexes following adoptive cell transplant could also be conducted to support proliferation, activation, and persistence of the transferred cells.

Pharmaceutical Therapeutics

The invention provides pharmaceutical compositions comprising fusion protein complexes for use as a therapeutic. In one aspect, fusion protein complex of the invention is administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, autoimmune or infectious diseases, although in certain instances lower amounts will be needed because of the increased specificity of the compound. A compound is administered at a dosage that enhances an immune response of a subject, or that reduces the proliferation, survival, or invasiveness of a neoplastic, infected, autoimmune or senescent cell as determined by a method known to one skilled in the art.

Formulation of Pharmaceutical Compositions

The administration of the fusion protein complex of the invention for the treatment of a neoplasia, infectious, senescent cell- or age-related or autoimmune disease is by any suitable means that results in a concentration of the therapeutic that, combined with other components, is effective in ameliorating, reducing, or stabilizing said neoplasia, infectious, senescent cell- or age-related or autoimmune disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 µg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. Preferably, the fusion protein complex is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, the fusion protein complex is formulated in an excipient suitable for parenteral administration.

Parenteral Compositions

The pharmaceutical composition comprising a fusion protein complex of the invention are administered parenterally by injection, infusion or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or it is presented as a dry powder to be reconstituted with water or another suitable vehicle before use. Apart from the active agent that reduces or ameliorates a neoplasia, infectious, senescent cell- or age-related or autoimmune disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating neoplasia, infectious diseases, senescent cell- or age-related diseases or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplasia, infectious disease, senescent cell- or age-related diseases or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, senescent cell- or age-related diseases, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, the fusion protein complex of the invention is administered in combination with any other standard therapy; such methods are known to the skilled artisan and described in Remington's Pharmaceutical Sciences by E. W. Martin. If desired, fusion protein complexes of the invention is administered in combination with any conventional anti-neoplastic therapy, including but not limited to, immunotherapy, therapeutic antibodies, targeted therapy, surgery, radiation therapy, or chemotherapy.

Kits or Pharmaceutical Systems

Pharmaceutical compositions comprising the fusion protein complex of the invention may be assembled into kits or pharmaceutical systems for use in ameliorating a neoplasia, infectious disease or senescent cell- or age-related diseases. Kits or pharmaceutical systems according to this aspect of the invention comprise a carrier means, such as a box, carton, tube, having in close confinement therein one or more container means, such as vials, tubes, ampoules, bottles and the like. The kits or pharmaceutical systems of the invention may also comprise associated instructions for using the fusion protein complex of the invention.

Recombinant Protein Expression

In general, preparation of the fusion protein complexes of the invention (e.g., components of a TxM complex) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques in Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also, biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-12, IL-18, IL-1, IL-17, TGF and TNF cytokine families, and to IL-1 through IL-35, IFN-α, IFN-β, IFN-γ, TGF-β, TNF-α, and TNF-β.

In an aspect of the invention, the first protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, Nature Rev. Immunol. 6:595-601).

In another aspect of the invention, the first protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. The IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some cases, the sequence of the IL-15 variant has at least one amino acid change, e.g. substitution or deletion, compared to the native IL-15 sequence, such changes resulting in IL-15 agonist or antagonist activity. Preferably, the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, like cytokines, are defined as any chemical factor or molecule which when exposed to other cells are responsible for many effects of cellular immunity. Suitable chemokines may include but are not limited to the CXC, CC, C, and CX$_3$C chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, *pseudomonas* exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd—or paramagnetic metal ion-based contrast agents. See e.g., Moskaug, et al. *J. Biol. Chem.* 264, 15709 (1989); Pastan, I. et al. Cell 47, 641, 1986; Pastan et al., Recombinant Toxins as Novel Therapeutic Agents, *Ann. Rev. Biochem.* 61, 331, (1992); "Chimeric Toxins" Olsnes and Phil, *Pharmac. Ther.*, 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA—GenBank: U14407.1 (incorporated herein by reference), *Mus musculus* interleukin 15 (IL15) mRNA—GenBank: U14332.1 (incorporated herein by reference), human interleukin-15 receptor alpha chain precursor (IL15RA) mRNA—GenBank: U31628.1 (incorporated herein by reference), *Mus musculus* interleukin 15 receptor, alpha chain—GenBank: BC095982.1 (incorporated herein by reference).

In some settings, it can be useful to make the protein fusion or conjugate complexes of the present invention polyvalent, e.g., to increase the valency of the sc-antibody. In particular, interactions between the IL-15 and IL-15Rα domains of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cysteine residues. Exemplary nanoparticles include liposomes, core-shell particles or PLGA-based particles.

In another aspect, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of TxM). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al. supra.

Included in the invention are methods for making a soluble fusion protein complex, the method comprising introducing into a host cell a DNA vector as described herein encoding the first and second proteins, culturing the host cell in media under conditions sufficient to express the fusion proteins in the cell or the media and allow association between IL-15 domain of a first protein and the soluble IL-15Rα domain of a second protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm.nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express the components of fusion protein complex of the invention (e.g., TxM). For example, a construct encoding one or more components of fusion protein complex of the invention can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immunoblotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein complexes encompass non-mammalian eukaryotic cells as well, including insect (e.g., Sp. *frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1,000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermenter.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (huIL-15) is trans-presented to immune effector cells by the human IL-15 receptor α chain (huIL-15Rα) expressed on antigen presenting cells. IL-15Rα binds huIL-15 with high affinity (38 pM) primarily through the extracellular sushi domain (huIL-15RαSu). As described herein, the huIL-15 and huIL-15RαSu domains can be used as a scaffold to construct multi-domain fusion complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcome for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop human-derived immunostimulatory multimeric scaffold, human IL-15 (huIL-15) and IL-15 receptor domains were used. huIL-15 is a member of the small four α-helix bundle family of cytokines that associates with the huIL-15 receptor α-chain (huIL-15Rα) with a high binding affinity (equilibrium dissociation constant (KD) ~$10^{-11}$ M). The resulting complex is then trans-presented to the human IL-2/15 receptor β/common γ chain (huIL-15RβγC) complexes displayed on the surface of T cells and NK cells. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIL-15Rα interactions suggest that these inter chain binding domains could serve as a human-derived immunostimulatory scaffold to make soluble dimeric molecules capable of target-specific binding.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Generation and Characterization of Fusion Protein Complexes Comprising IL-15, IL-7 and IL-21 Domains An important therapeutic approach for treating cancer or infectious disease relies on augmenting immune cell activity against the diseased cells. This strategy includes stimulating immune cells ex vivo followed by adoptive transfer and/or directly increasing immune cell levels or activity in vivo in the patient. Immune cells involved in these approaches may be those of the innate (i.e., NK cells) or adaptive (i.e., T cells) immune system.

One approach for augmenting immune activity is to provide immunostimulatory cytokines to the immune cells. Such cytokines are known in the art and can be used alone or in combination with other cytokines or agents. As described in detail below, fusion protein complexes comprising an IL-15N72D:IL-15RαSu/Fc scaffold fused to IL-7 and IL-21 binding domains were generated (FIGS. 1A, 1B). These fusion protein complexes have advantages in binding to NK and T cells and signaling cell responses via each of the cytokine receptors. The Fc region of Ig molecules forms a dimer to provide a soluble multi-polypeptide complex, can bind Protein A for the purpose of purification and can interact with Fcγ receptors on NK cells and macrophages, thus providing advantages to the fusion protein complex that are not present in the combination of individual cytokines. Additionally, interactions between the IL-15N72D and IL-15RαSu domains provide a means to link the IL-15N72D, IL-7 and IL-21 (and possibly other protein domains or agents) into a single immunostimulatory fusion protein complex.

Specifically, constructs were made linking IL-7 and IL-21 domains to the IL-15N72D and IL-15RαSu/Fc chains. In some cases, either IL-7 or IL-21 polypeptide is linked to the N-terminus of the IL-15N72D and/or IL-15RαSu/Fc chains. In other cases, the IL-7 or IL-21 polypeptide is linked to the N-terminus of IL-15N72D and/or IL-15RαSu/Fc chains. Specific fusion protein complexes comprising an IL-15N72D:IL-15RαSu/Fc scaffold fused to IL-7 and IL-21 binding domains are described below.

1) A fusion protein complex was generated comprising IL-21/IL-15RαSu/Fc and IL-7/IL-15N72D fusion proteins. The human IL-7 and human IL-21 sequences were obtained from the UniProt website and DNA for these sequences was synthesized by Genewiz. Specifically, constructs were made directly linking the synthesized IL-21 sequence to the N-terminal coding region of IL-15RαSu/Fc via overlapping PCR. The nucleic acid and protein sequences of a construct comprising IL-21 linked to the N-terminus of IL-15RαSu/Fc are shown below.

The nucleic acid sequence of the IL-21/IL-15RαSu/Fc construct (including signal peptide sequence) is as follows (SEQ ID NO: 1):

```
(Signal peptide)
atgaagtgggtgaccttcatcagcctgctgttcctgttctccagcgccta ctcc (Human IL-21)
cagggccaggacaggcacatgatccggatgaggcagctcatcgacatcgt cgaccagctgaagaactacgtgaacgacctggtgcccgagtttctgcctg cccccgaggacgtggagaccaactgcgagtggtccgccttctcctgcttt cagaaggcccagctgaagtccgccaacaccggcaacaacgagcggatcat caacgtgagcatcaagaagctgaagcggaagcctcctccacaaacgccg gcaggaggcagaagcacaggctgacctgccccagctgtgactcctacgag aagaagcccccaaggagttcctggagaggttcaagtccctgctgcagaa gatgatccatcagcacctgtcctccaggacccacggctccgaggactcc (Human IL-15R a sushi domain)
atcacgtgtcctcctcctatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgcattaga (Human IgG1 CH2-CH3 (Fc) domain)
gagccgaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagccctcccagcccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg actccgacggctccttcttcctctacagcaagctcaccgtggacaagagc aggtggcagcaggggaacgtcttctcatgctccgtgatgcatgaggctct gcacaaccactacacgcagaagagcctctccctgtctccggtaaa
```

The amino acid sequence of the IL-21/IL-15RαSu/Fc construct (including signal peptide sequence) is as follows (SEQ ID NO: 2):

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R a sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK

In some cases, the leader peptide is cleaved from the intact polypeptide to generate the mature form that may be soluble or secreted.

Constructs were also made linking the synthesized IL-7 sequence to the N-terminus coding region of IL-15N72D via overlapping PCR. The nucleic acid and protein sequences of a construct comprising IL-7 linked to the N-terminus of IL-15N72D are shown below.

The nucleic acid sequence of the IL-7/IL-15N72D construct (including leader sequence) is as follows (SEQ ID NO: 3):

(Signal peptide)
atgaagtgggtgaccttcatcagcctgctgttcctgttctccagcgcta ctcc (Human IL-7)
gattgcgacatcgagggcaaggacggcaagcagtacgagagcgtgctgat ggtgtccatcgaccagctgctggacagcatgaaggagatcggctccaact gcctcaacaacgagttcaacttcttcaagcggcacatctgcgacgccaac aaggagggcatgttcctgttcagggccgccaggaaactgcggcagttcct gaagatgaactccaccggcgacttcgacctgcacctgctgaaggtgtccg agggcaccaccatcctgctgaactgcaccggacaggtgaagggccggaaa cctgctgctctgggagaggcccaacccaccaagagcctggaggagaacaa gtccctgaaggagcagaagaagctgaacgacctgtgcttcctgaagaggc tgctgcaggagatcaagacctgctggaacaagatcctgatgggcaccaag gagcat (Human IL-15N72D)
aactgggttaacgtaataagtgatttgaaaaaaattgaagatcttattca atctatgcatattgatgctactttatatacggaaagtgatgttcacccca gttgcaaagtaacagcaatgaagtgctttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct The amino acid sequence of the mature IL-7/IL-15N72D fusion protein (including leader sequence) is as follows (SEQ ID NO: 4):

(Signal peptide)
MKWVTFISLLFLFSSAYS (Human IL-7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the intact polypeptide to generate the mature form that may be soluble or secreted.

Figure 2A:
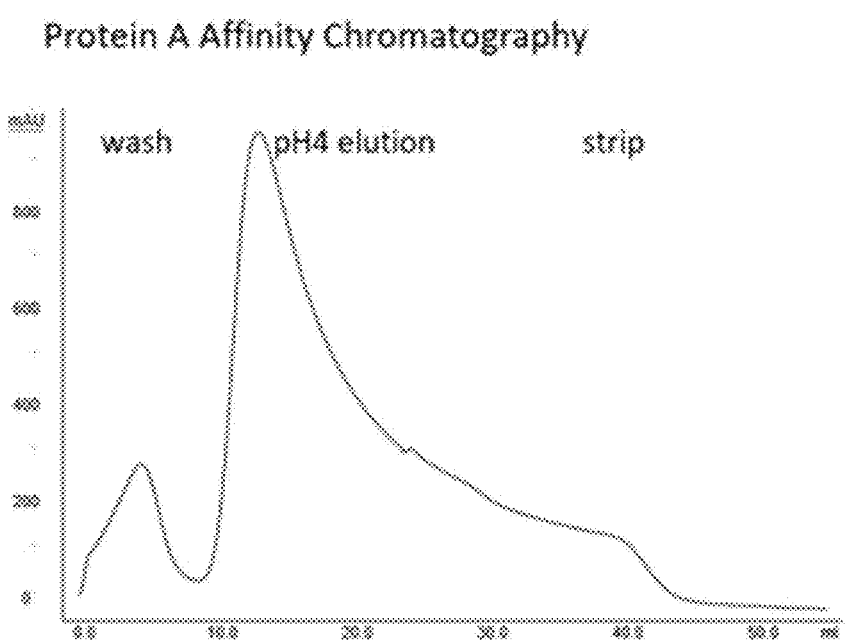
FIG. 2A is a line graph showing the chromatographic profile of hIL7/IL21/TxM protein-containing cell culture supernatant following binding and elution on a Protein A resin.
Figure 2B:
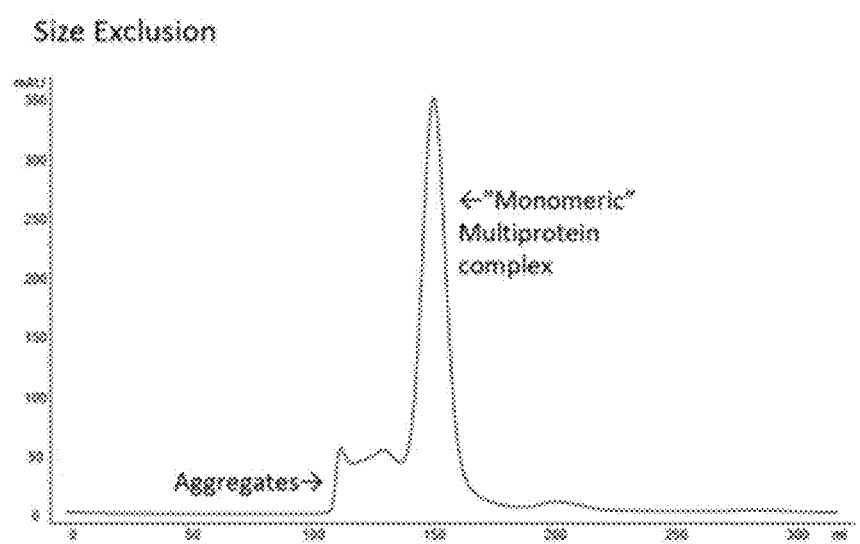
FIG. 2B is a line graph showing the chromatographic profile of Protein A-purified hIL7/IL21/TxM fusion protein complex following elution on a preparative size exclusion column.
Figure 2C:
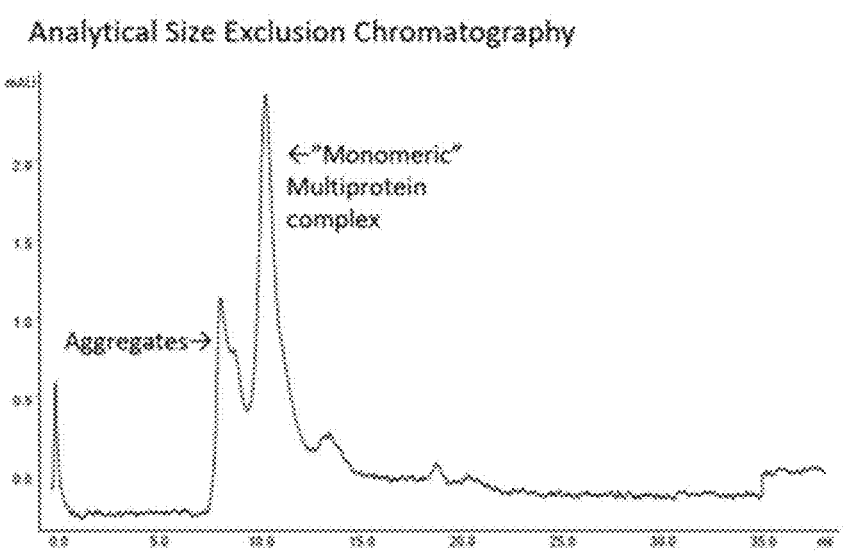
FIG. 2C is a line graph showing the chromatographic profile of Protein A/SEC-purified hIL7/IL21/TxM fusion protein complex following elution on an analytical size exclusion column, demonstrating separation of monomeric multiprotein hIL7/IL21/TxM fusion protein complexes from protein aggregates.

The IL-21/IL-15RαSu/Fc and IL-7/IL-15N72D constructs were cloned into expression vectors as described previously (U.S. Pat. No. 8,507,222, at Example 1, incorporated herein by reference), and the expression vectors transfected into CHO cells. Co-expression of the two constructs in CHO cells allowed for formation and secretion of a soluble IL-7/IL-15N72D:IL-21/IL-15RαSu/Fc fusion protein complex (referred to as hIL7/IL21/TxM). The hIL7/IL21/TxM protein was purified from CHO cell culture supernatant by Protein A affinity chromatography and size exclusion chromatography resulting in soluble (non-aggregated) fusion protein complexes consisting of IL-21/IL-15RαSu/Fc dimers and IL-7/IL-15N72D fusion proteins (FIG. 2).

Figure 3A:
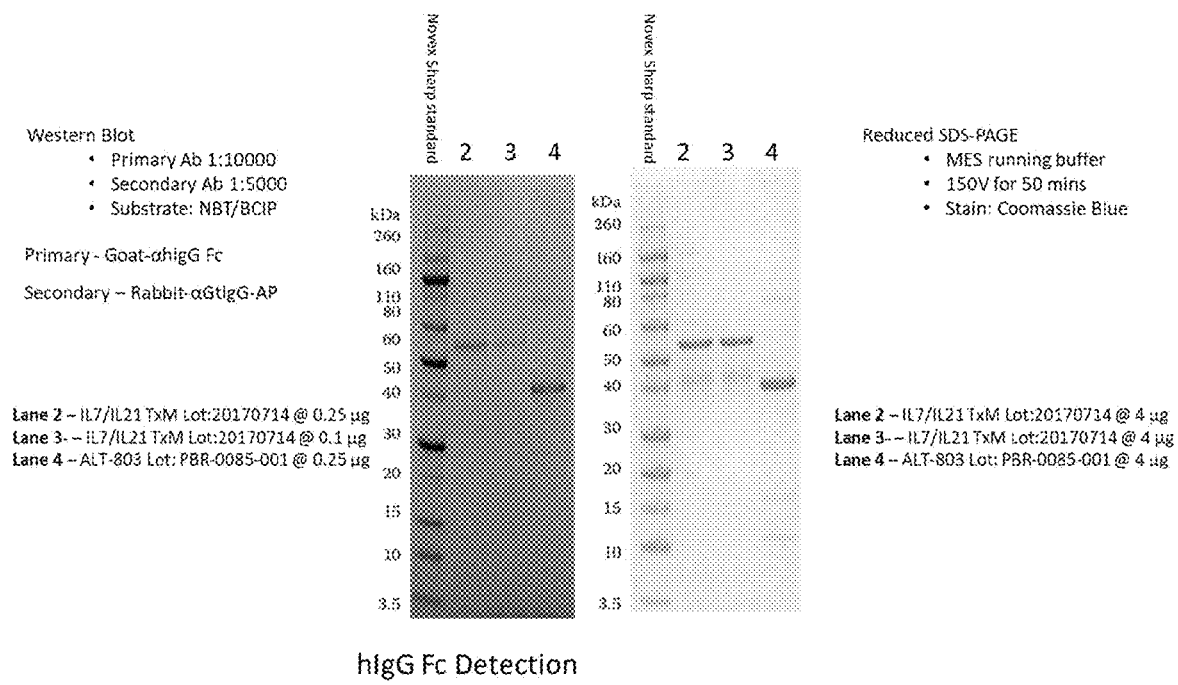
FIG. 3A shows photographs of 1) a Western blot to detect protein bands containing human IgG Fc domains (left panel) and 2) Coomassie Blue-stained sodium dodecyl sulfate polyacrylamide gel (4-12%) electrophoresis (SDS-PAGE) analysis (right panel) of the hIL7/IL21/TxM fusion protein complex following disulfide bond reduction.
Figure 3B:
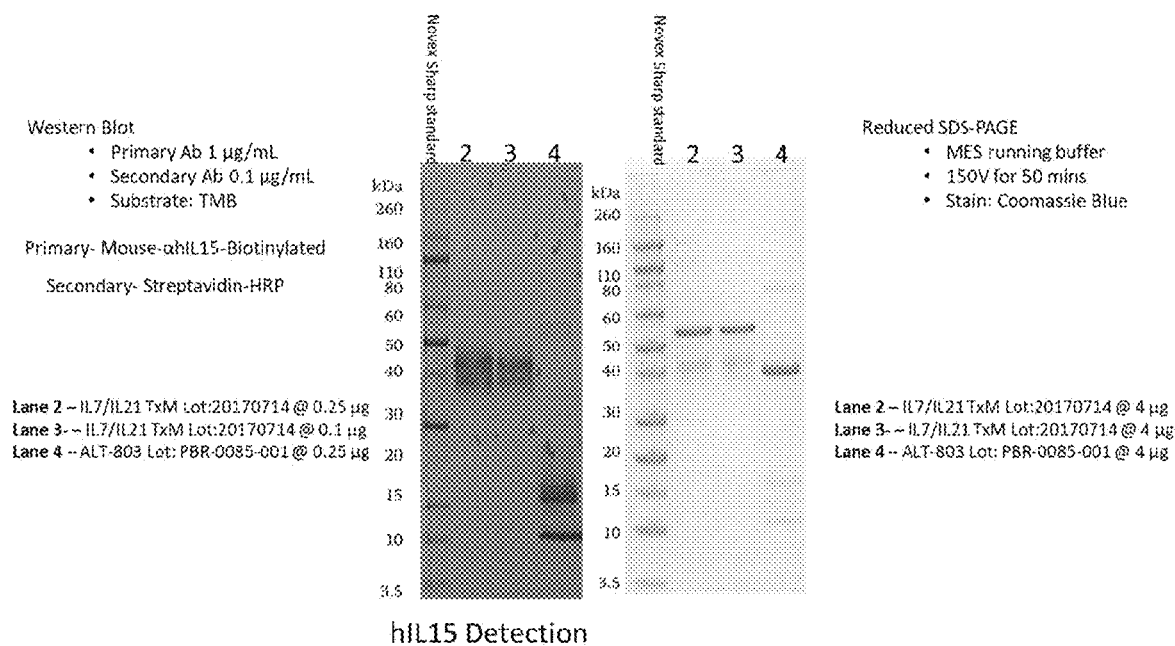
FIG. 3B shows photographs of 1) a Western blot to detect protein bands containing human IL-15 domains (left panel) and 2) Coomassie Blue—sodium dodecyl sulfate polyacrylamide gel (4-12%) electrophoresis (SDS-PAGE) analysis (right panel) of the hIL7/IL21/TxM fusion protein complex following disulfide bond reduction. For each type of analysis, lane 1 is the Novex Sharp protein standard, lanes 2 & 3: purified hIL7/IL21/TxM Lot 20170714, and lane 4: ALT-803 (IL-15N72D:IL-15RαSu/Fc complex) control.

Reduced SDS-PAGE and Western blot analyses of the Protein A-purified IL-7/IL-15N72D:IL-21/IL-15RαSu/Fc fusion protein complexes are shown in FIG. 3. For the Western blot analysis, purified proteins were separated by reduced SDS-PAGE on 4-12% Bis-Tris gel. The resolved protein bands were transferred from the gel to membrane using the Invitrogen iBlot2 system. The membrane was probed with 1) goat anti-hIgG Fc Ab (primary) and rabbit anti-goat IgG-AP (secondary) for detection of protein bands containing the human Fc domain and 2) biotinylated mouse anti-hIL15 Ab (primary) and streptavidin-HRP (secondary) for detection of protein bands containing the human IL-15 domain. Binding of the probe reagents was detected following incubation with appropriate substrates (NBT/BCIP or TMB) using the Millipore SNAP i.d. 2.0 protein detection system. Bands in the SDS-PA gels and Western blots corresponding to the soluble IL-21/IL-15RαSu/Fc and IL-7/IL-15N72D proteins migrate at about 54 kDa and ~38-45 kDa, respectively, were observed (FIGS. 3A and B).

Figure 4:
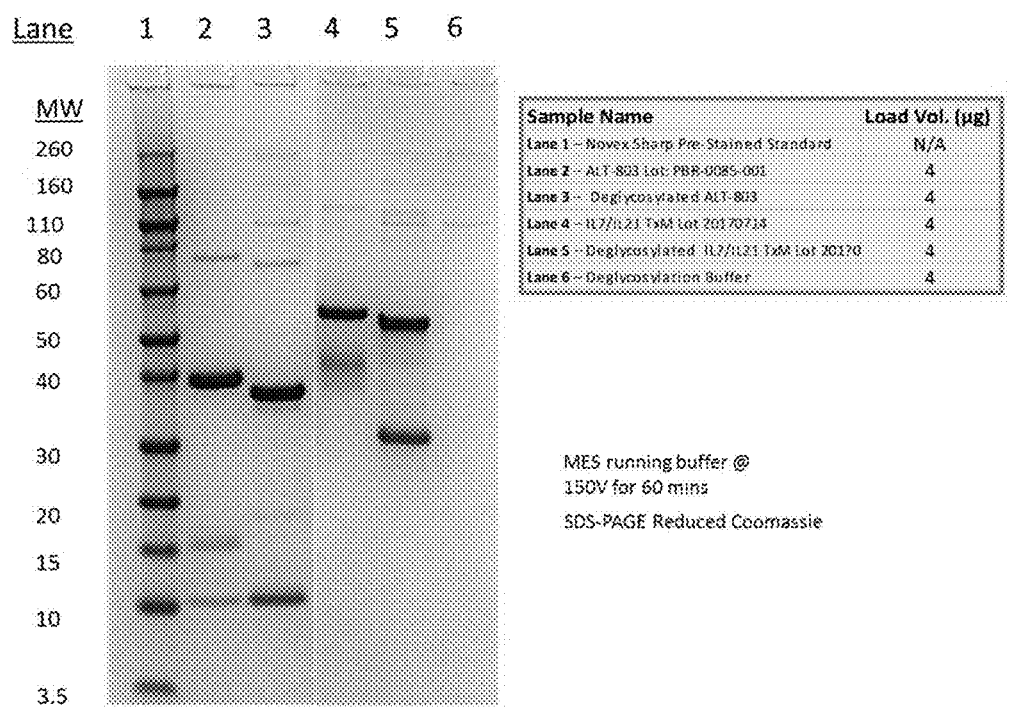
FIG. 4 shows a photograph of Coomassie Blue-stained SDS-PAGE analysis of ALT-803 (control) (lanes 2 & 3) and hIL7/IL21/TxM fusion protein complex (lanes 4 & 5) following disulfide bond reduction. The protein samples in lanes 3 & 5 had been deglycosylated with the Protein Deglycosylation Mix II (New England BioLabs) according to manufacturer's instructions. Lane 1 is the Novex Sharp protein standard, lane 2: ALT-803, lane 3: deglycosylated ALT-803, lane 4: hIL7/IL21/TxM Lot 20170714, lane 5: deglycosylated hIL7/IL21/TxM Lot 20170714, and lane 6: deglycosylation reaction buffer (containing deglycosylase enzymes).
Figure 5:
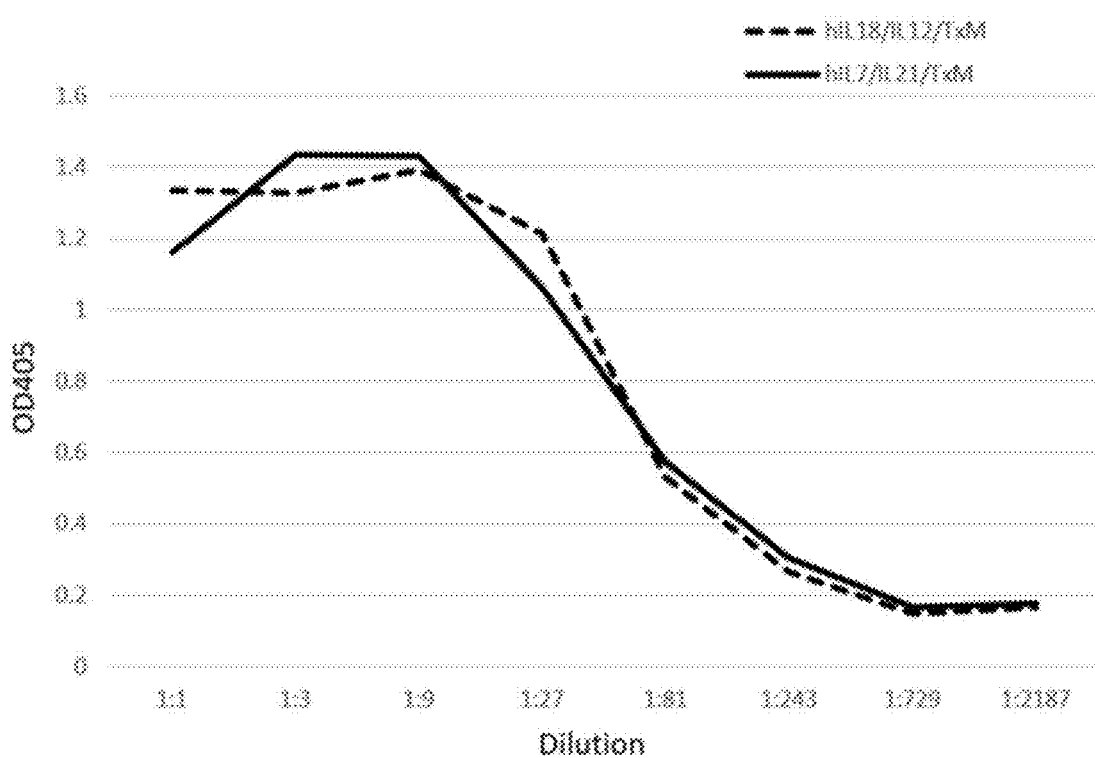
FIG. 5 is a line graph showing the binding activity of the hIL7/IL21/TxM fusion protein complex to antibodies specific to human IL-15 and human IgG.
Figure 6A:
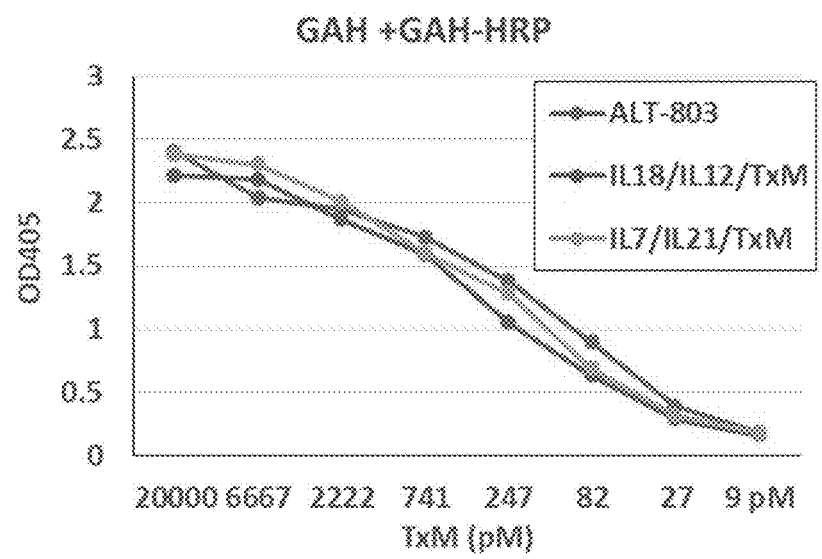
FIGS. 6A-6E are a series of line graphs depicting the binding activity of the hIL7/IL21/TxM fusion protein complex to antibodies specific to human IgG (GAH) (FIG. 6A), IL15 (FIG. 6B), IL7 and IL15 (FIG. 6C), IL21 and IL15 (FIG. 6D) and IL7 and IL21 (FIG. 6E).
Figure 6B:
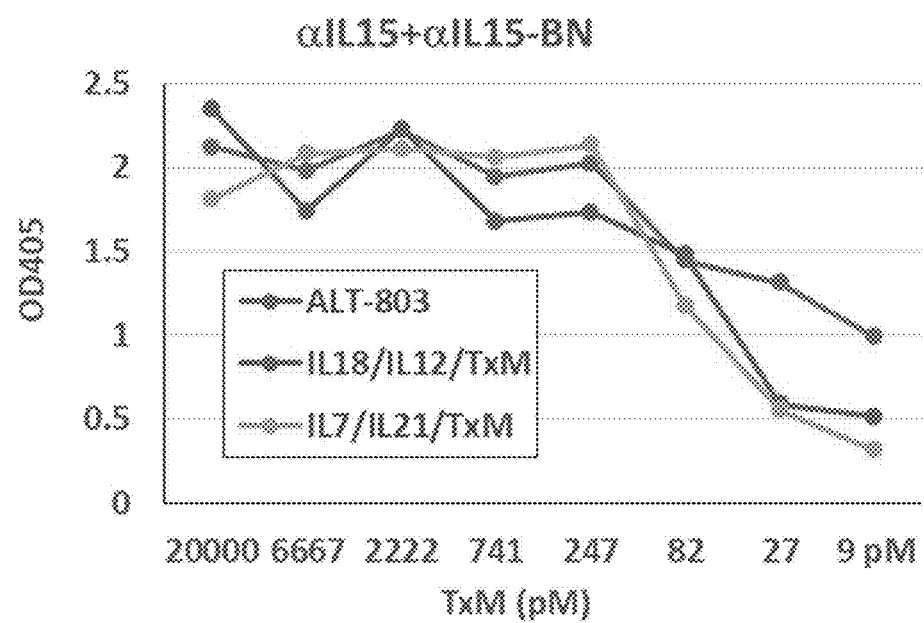
Figure 6C:
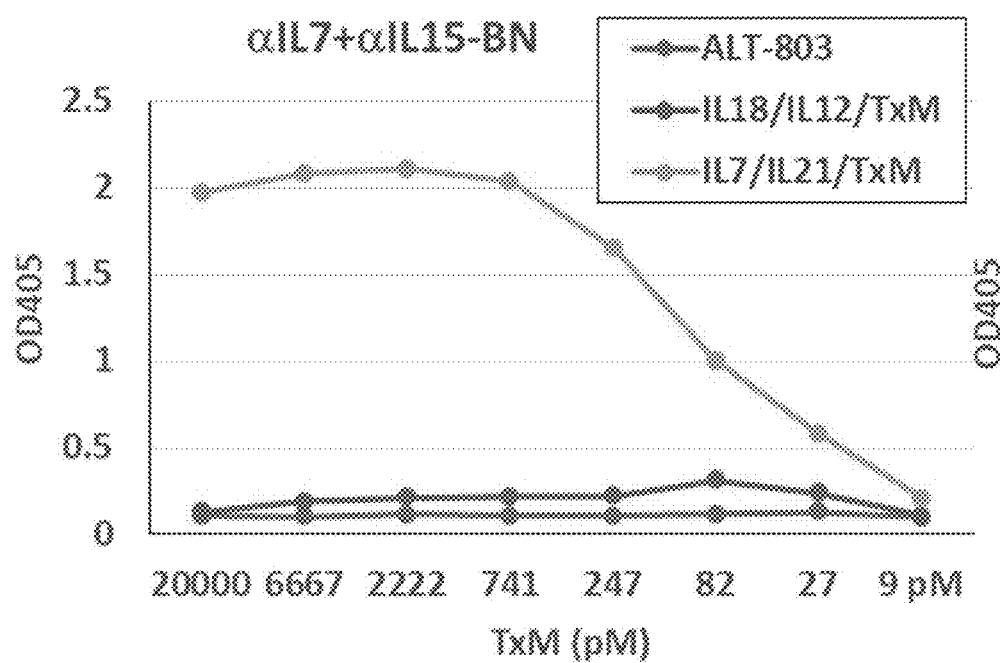
Figure 6D:
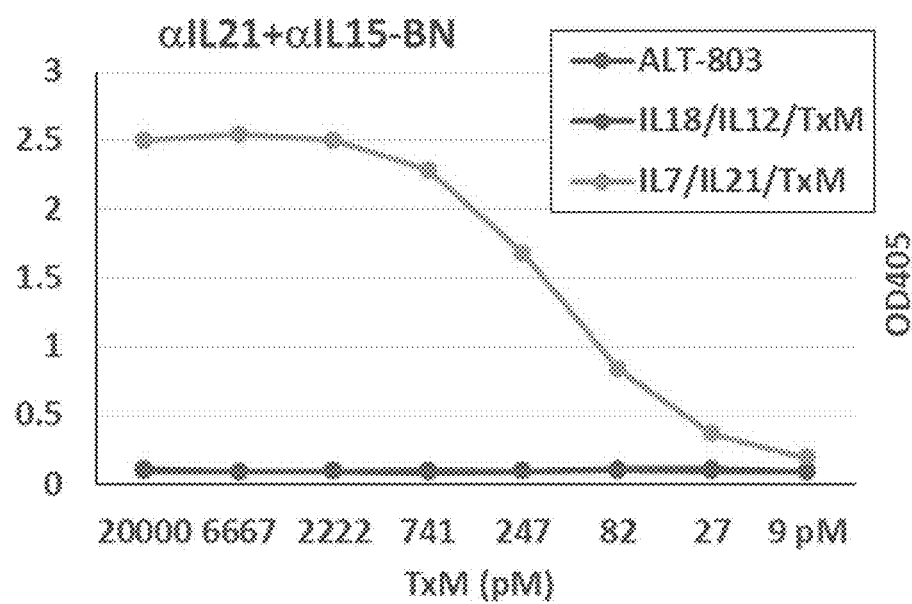
Figure 6E:
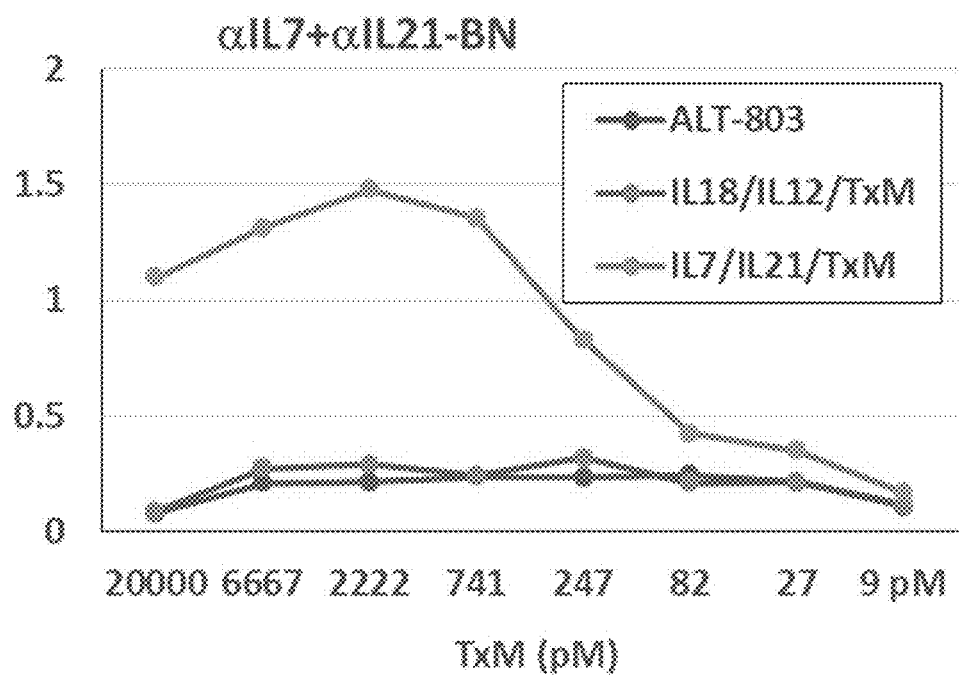

The calculated molecular masses of the IL-21/IL-15RαSu/Fc and IL-7/IL-15N72D proteins are about 49 kDa and 30 kDa, respectively. To assess the differences between the calculated and observed molecular masses, deglycosylation studies were conducted on the purified protein complexes using the Protein Deglycosylation Mix II (New England BioLabs). Briefly, 100 µg of protein complex in 1× Deglycosylation Mix Buffer 2 was denatured at 75° C. for 10 minutes. After cooling down to room temperature, 5 µl of Protein Deglycosylation Mix II was added to the protein mixture. Following incubation at room temperature for 30 minutes, the proteins were deglycosylated overnight at 37° C. After the deglycosylation reaction, the samples are ready to be analyzed on reduced Coomassie-stained SDS-PAGE. ALT-803, hIL7/IL21/TxM protein that was not deglycosylated, and the Protein Deglycosylation Mix (containing the deglycosylase enzyme) were also analyzed as controls. The results indicate that bands corresponding to the deglycosylated IL-21/IL-15RαSu/Fc and IL-7/IL-15N72D proteins migrate at about 51 kDa and 30 kDa, respectively, consistent with the calculated molecular masses (FIG. 4). These findings confirm that the mammalian cell produced proteins of the hIL7/IL21/TxM complex are glycosylated. ELISA-based methods confirmed the formation of the hIL7/IL21/TxM fusion protein complex. In FIG. 5, the IL-7/IL-15N72D:IL-21/IL-15RαSu/Fc fusion protein complexes in the culture supernatant from transfected CHO cells were detected using a huIgG1/IL15-specific ELISA with a capture antibody, anti-human IL-15 antibody (MAB647, R&D Systems) and a detection antibody, horseradish peroxidase conjugated anti-human IgG antibody. This is compared to a similar cytokine TxM fusion protein complex (hIL18/IL12/TxM) with a known concentration. The signal from the hIL7/IL21/TxM fusion protein complex can be compared to that of the hIL18/IL12/TxM control to estimate the fusion protein concentration.

Similar ELISAs were conducted on purified hIL7/IL21/TxM using capture and probe antibodies to human IgG (GAH) and IL-15 and combinations of antibodies to IL7 and IL15, IL21 and IL15 and IL7 and IL21 (FIGS. 6A-6E). In these assays, hIL18/IL12/TxM and ALT-803 were used as controls. The results from these assays demonstrate that soluble IL-7/IL-15N72D, IL-21/IL-15RαSu/Fc proteins can be produced in CHO cells and the hIL7/IL21/TxM fusion protein complexes can form and be secreted into the culture media. The secreted protein can be purified and the fusion protein complex remains intact.

Figure 7:
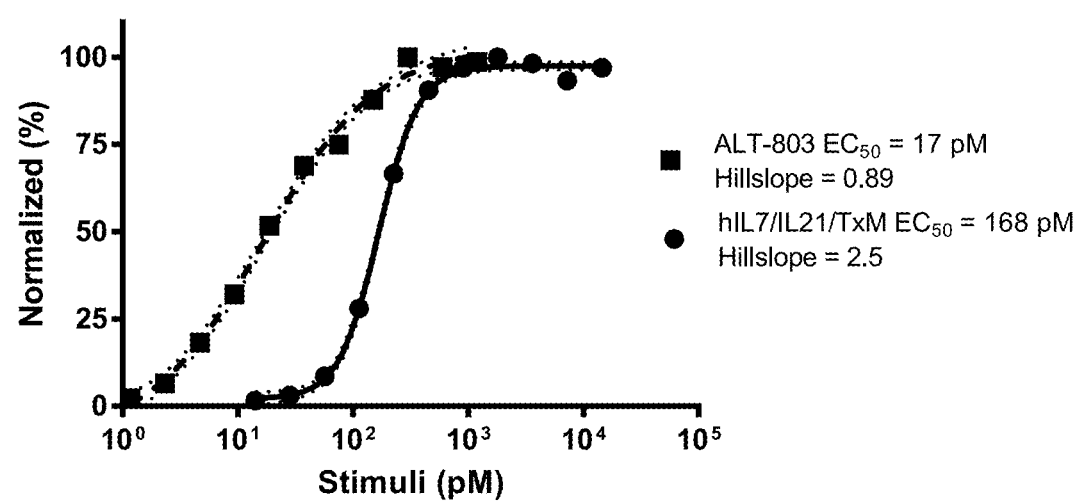
FIG. 7 is a line graph illustrating the proliferation of IL-15-dependent 32D13 cells mediated by hIL7/IL21/TxM fusion protein complex compared to ALT-803.
Figure 8A:
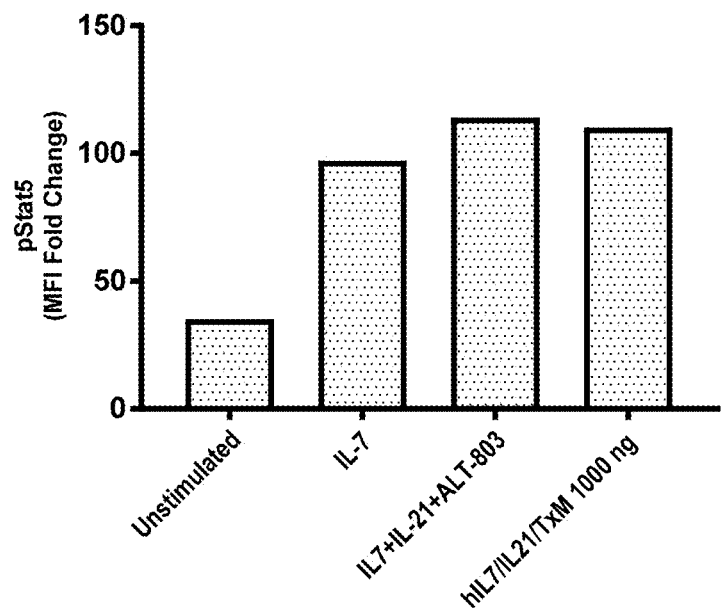
FIG. 8A is a bar graph showing IL-7 biological activity of hIL7/IL21/TxM fusion protein complex, a combination of recombinant IL-7, IL-21 and ALT-803 (IL-7+IL-21+ALT-803), and recombinant IL-7 alone by measuring phosphorylation of Stat5 in mouse 2E8 cells by flow cytometry. Data represent the mean fluorescence intensity (MFI) fold change.
Figure 8B:
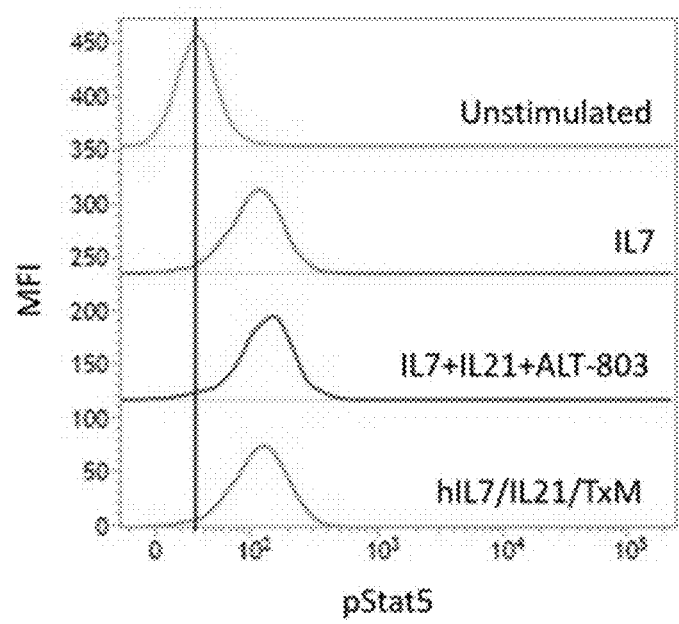
FIG. 8B is a histogram showing IL-7 biological activity of hIL7/IL21/TxM fusion protein complex, a combination of recombinant IL-17, IL-21 and ALT-803 (IL-7+IL-21+ALT-803), and recombinant IL-7 alone compared to media control by measuring phosphorylation of Stat5 in mouse 2E8 cells by flow cytometry.
Figure 8C:
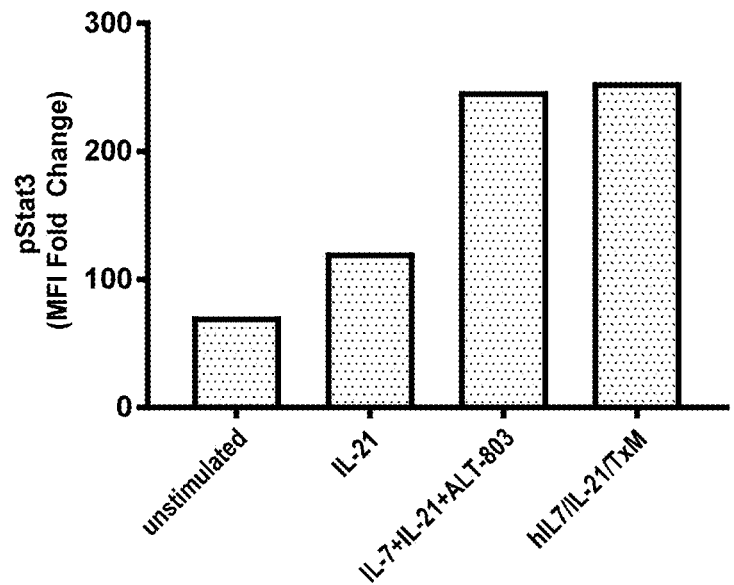
FIG. 8C is a bar graph showing IL-21 biological activity of hIL7/IL21/TxM fusion protein complex, a combination of recombinant IL-7, IL-21 and ALT-803 (IL-7+IL-21+ALT-803), and recombinant IL-21 alone by measuring phosphorylation of Stat3 in purified human T cells by flow cytometry. Data represent the MFI fold change.
Figure 8D:
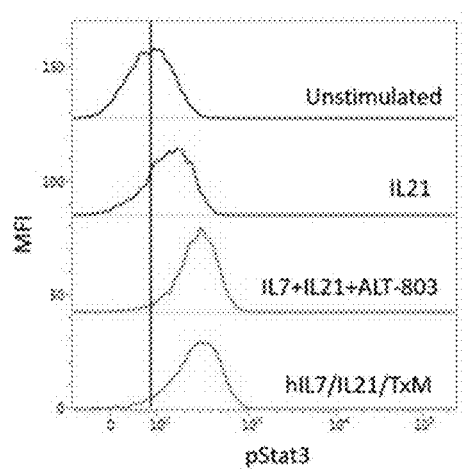
FIG. 8D is a histogram showing IL-21 biological activity of hIL7/IL21/TxM fusion protein complex, a combination of recombinant IL-17, IL-21 and ALT-803 (IL-7+IL-21+ALT-803), and recombinant IL-21 alone compared to media control by measuring phosphorylation of Stat3 in purified human T cells by flow cytometry.
Figure 8E:
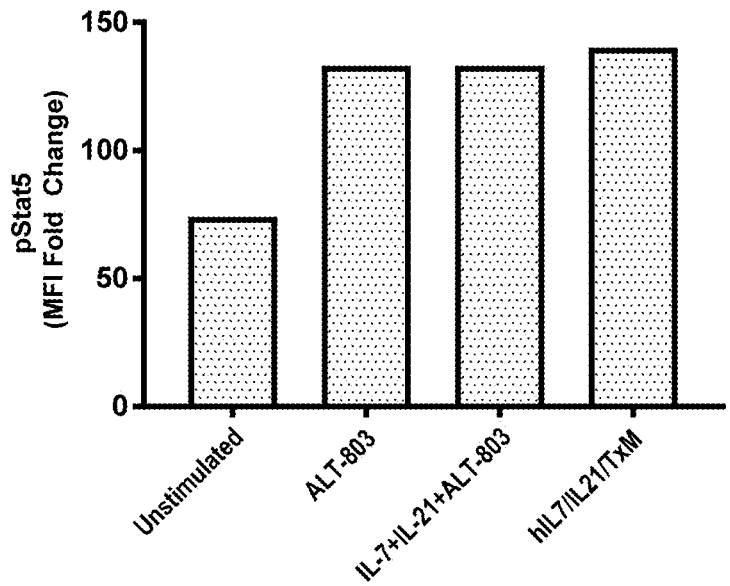
FIG. 8E is a bar graph showing IL-15 biological activity of hIL7/IL21/TxM fusion protein complex, a combination of recombinant IL-7, IL-21 and ALT-803 (IL-7+IL-21+ALT-803), and ALT-803 alone by measuring phosphorylation of Stat5 in 32D3 cells by flow cytometry. Data represent the MFI fold changes.
Figure 8F:
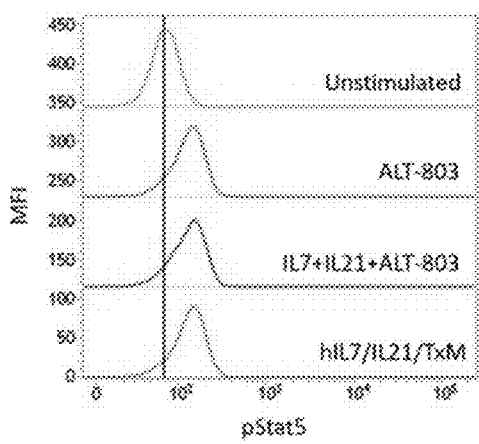
FIG. 8F is a histogram showing IL-15 biological activity of hIL7/IL21/TxM fusion protein complex, a combination of recombinant IL-17, IL-21 and ALT-803 (IL-7+IL-21+ALT-803), and ALT-803 alone compared to media control by phosphorylation of Stat5 in 32D3 cells by flow cytometry.

Example 2: In Vitro Characterization of the Activities of hIL7/IL21/TxM Fusion Protein Complexes To assess the IL-15 immunostimulatory activity of the hIL7/IL21/TxM fusion protein complexes, proliferation of IL-15-dependent 32D13 cells, a mouse hematopoietic cell line, was assessed. Increasing levels of hIL7/IL21/TxM were added to 32D13 cells ($10^4$ cells/well) in 200 µL IMDM: 10% FBS media and cells were incubated for 3 days at 37° C. PrestoBlue cell viability reagent (20 µL/well) then was added. After 4 hours, absorbance was measured at 570 nm (with a 600 nm reference wavelength for normalization) to determine cell proliferation based on reduction of PrestoBlue, a resazurin-based solution, by metabolically active cells. The bioactivity of the IL-15N72D:IL-15RαSu/Fc complex (ALT-803) was assessed as a positive control. As shown in FIG. 7, hIL7/IL21/TxM was able to promote cell proliferation of 32D13 cells, thereby demonstrating IL-15 activity. The activity of hIL7/IL21/TxM was reduced compared to that of ALT-803, possibly due to the linkage of IL-7 to the IL-15N72D domain.

In order to demonstrate the individual activity of each cytokine (IL-7, IL-21, and IL-15), flow cytometry-based intracellular phosphoprotein assays were developed by utilizing proteins that are uniquely phosphorylated in response to receptor signaling by each cytokine (IL-7: Stat5, IL-21: Stat3, and IL-15: Stat5). To test IL-7 activity, mouse 2E8 cell lines were cultured in Iscove's modified Dulbecco's medium (IMDM) with 4 mM L-glutamine, 1.5 g/L sodium bicarbonate, 0.05 mM 2-mercaptoethanol, 1 ng/ml mouse interleukin-7 and 20% FBS. For the phospho-flow cytometry-based Stat5 assay, cells were washed twice in IMDM and cultured at $0.5 \times 10^6$/ml overnight in complete media without IL-7 in a 37° C., 5% $CO_2$ incubator. The next day, the cells were washed in IMDM and counted.

IL-15 activity was measured in 32D13 cell lines by measuring phospho-Stat5 by flow cytometer. 32D13 cell lines were cultured in IMDM with 2 ng/ml human IL-2 and 10% FBS. For the phospho-flow cytometry based Stat5 assay, cell were washed twice in IMDM and cultured at $0.5 \times 10^6$/ml overnight in complete media without IL-7 in a 37° C., 5% $CO_2$ incubator. The next day, the cells were washed in IMDM and counted.

IL-21 activity was measured in purified human T cells by measuring phospho-Stat3 (727) by flow cytometer. Fresh human leukocytes were obtained from the blood bank and $CD3^+$ T cells were isolated with the RosetteSep/human $CD3^+$ T cell reagent (StemCell Technologies). The purity of $CD3^+$ T cells was >95%. Cells were cultured in RPMI 1640 supplemented with 2 mM L-glutamine, penicillin, streptomycin, and 10% FBS.

Cells ($0.25 \times 10^6$/tube) were seeded in FACS tube to test activity of each cytokine. Cells were stimulated with IL-7 (100 ng), IL-21 (100 ng) and ALT-803 (100 ng) alone or in combination at the same concentrations or with hIL7/IL21/TxM (1000-62.5 ng/mL) for 15 minutes in a 37° C., 5% $CO_2$ incubator. Final volume of media and cytokine were adjusted to 100 µL. After a 15 min incubation, paraformaldehyde (Sigma) was added at a final concentration of 1.6% and the cells were incubated in room temperature in the dark for an additional 10 min. The cells were then washed with 1 mL of FACS buffer (PBS, 0.5% BSA, 0.1% $NaN_3$) by centrifugation at 1500 rpm for 5 min at room temperature. The cell pellet was resuspended in 100 µl of chilled 100% methanol by gently vortexing. Cells were further incubated for 30 min at 4° C. and then washed with 1 mL of FACS buffer. The cell pellets were then resuspended in 50 µl of FACs buffer containing Phospho-Stat5 Alexa-Fluro-488 antibody (BD Bioscience) to test IL-7 and IL-15 activities or Phospho-Stat3 Alexa-Fluro-488 antibody (BD Bioscience) to test IL-21 activity. After a 30 min incubation at room temperature in the dark, the cells were washed with 1 mL of FACS buffer, resuspended in 300 µL of FACS buffer and analyzed by flow cytometry.

Following short term stimulation of mouse 2E8 cells or purified human T cells (>95% $CD3^+$) or 32D13 cells with 1 µg/mL (6.3 nM) hIL7/IL21/TxM resulted in similar responses to that seen with the combination of recombinant IL-7 (107 ng/mL; 6.3 nM), IL-21 (112 ng/mL; 6.3 nM) and ALT-803 (15.12 ng/mL; 6.3 nM) (FIG. 8A-F). These results demonstrate that each of the cytokine domains of the hIL7/IL21/TxM fusion protein complex retains its specific immunostimulatory biological activity.

It is known that the combination of IL-7, IL-21 and IL-15 activity is more effective at inducing IFN-γ production by naïve T cells than any of these cytokines alone. In order to evaluate the combined cytokine activity of the hIL7/IL21/TxM complex, purified T cells were incubated with hIL7/

Figure 9:
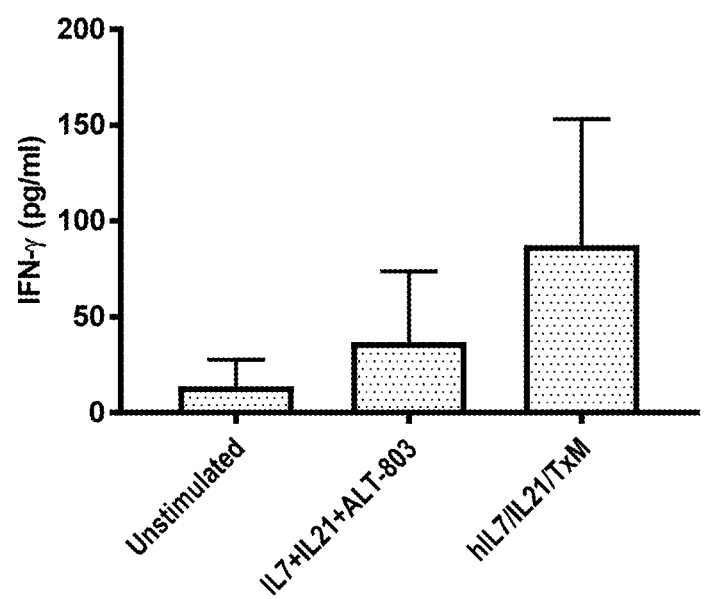
FIG. 9 is a bar graph showing IFN-γ production by purified human naïve T cells following stimulation with hIL7/IL21/TxM fusion protein complex compared to stimulation with combination of recombinant IL-7, IL-21 and ALT-803 (IL-7+IL-21+ALT-803). IFN-γ production was measured by ELISA.

IL21/TxM complex (6.3 nM), combinations of IL-7 (6.3 nM), IL-21 (6.3 nM), and ALT-803 (6.3 nM) or each cytokine alone. After 3 days, IFN-γ levels in the culture supernatants were determined by ELISA methods. As shown in FIG. 9, purified T cells in the presence of combined individual cytokines, IL-7+IL-21+ALT-803, induced IFN-γ production. However, when cultured in the presence of hIL7/IL21/TxM complex naïve T cells produced a high level of IFN-γ. These results verify that hIL7/IL21/TxM fusion protein complex exhibits the expected immunostimulatory activity of the combined IL-7, IL-21 and IL-15 cytokines.

Figure 10A:
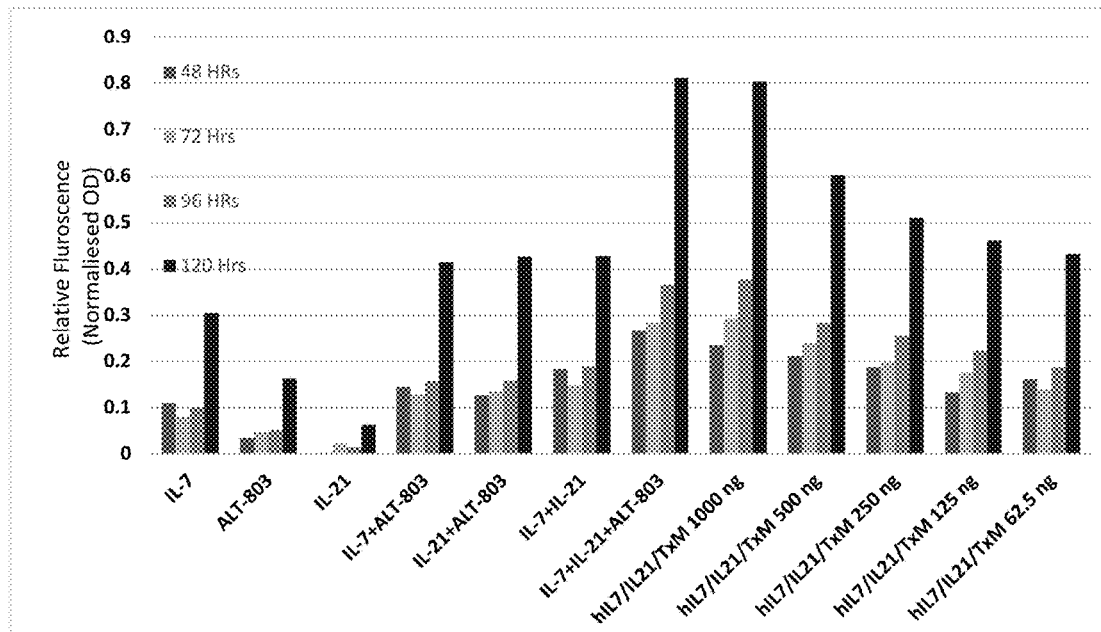
Figure 10A:
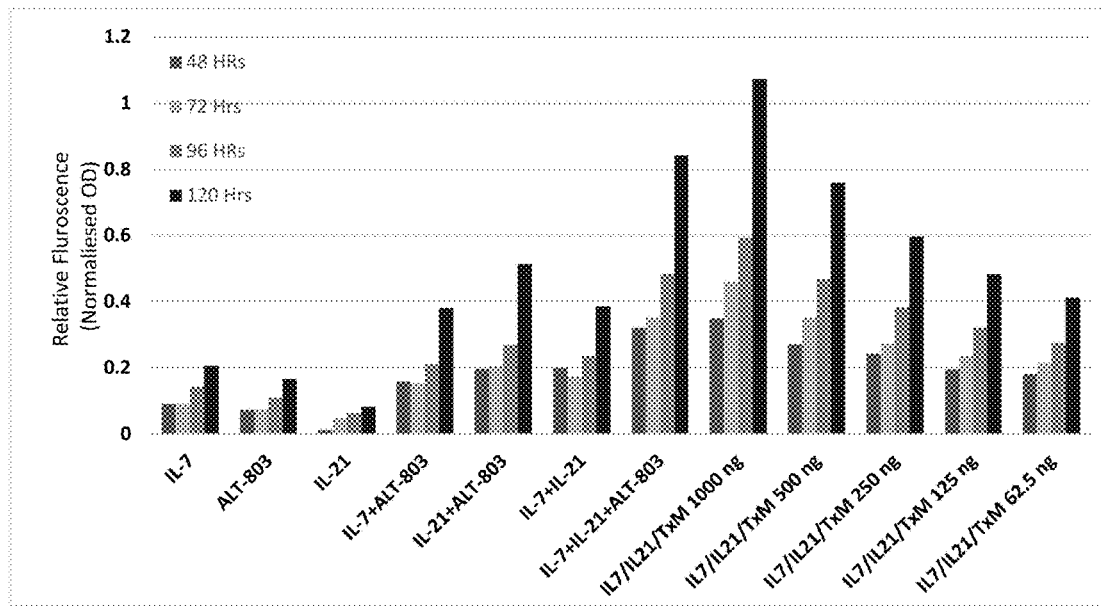
Figure 10C:
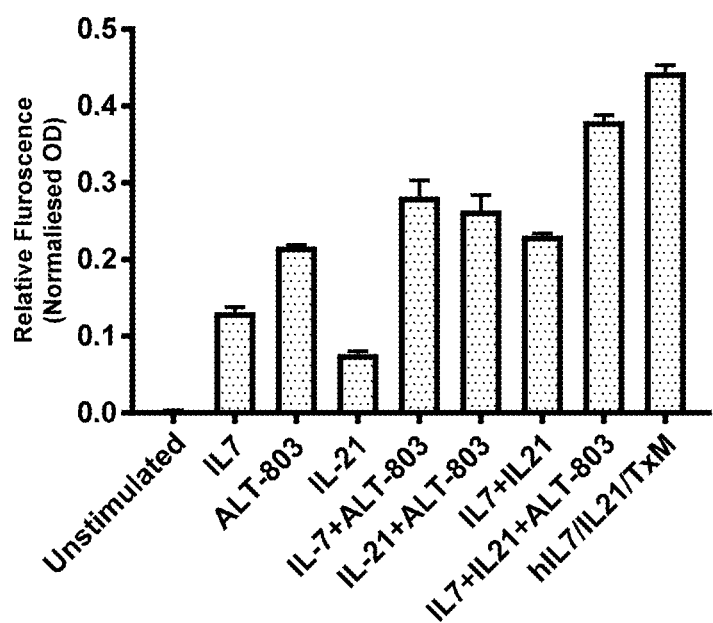
FIG. 10C is a bar graph showing average human T cell proliferation at the 72 hr time-point for the data shown in FIGS. 10A and 10B.

Example 3: Proliferation of Purified Naïve T Cells, CD3+ T Cells and CD8+ T Cells Following Stimulation with hIL7/IL21/TxM Fusion Protein Complexes Previous studies have shown that T cell proliferation can be efficiently induced in the presence of IL-7, IL-15, and IL-21. To evaluate the ability of hIL7/IL21/TxM fusion protein complex to promote proliferation of T cells, human naïve T cells were purified using RosetteSep human naïve CD8+ T cells kit (STEMCELL Technology) from blood from two healthy donors ($1 \times 10^5$ cells/ml). These cells (>85% CD3+) were cultured with hIL7/IL21/TxM or the combination of individual recombinant IL-7, IL-21, and ALT-803 for 2-5 days. Proliferation of cytokine-stimulated naïve T cells was assessed by Presto-Blue and analyzed by flow cytometry. The results indicate that hIL7/IL21/TxM fusion protein complex is capable of inducing proliferation of purified naïve T cells to a similar or greater extent than the combination of IL-7, IL-21 and IL-15 (FIGS. 10A and B show results from 2 different donors, FIG. 10C shows the averaged results for the 72 hr time-point). Thus, stimulation with the hIL7/IL21/TxM fusion protein complex can induce proliferation of purified naïve T cells.

Figure 11:
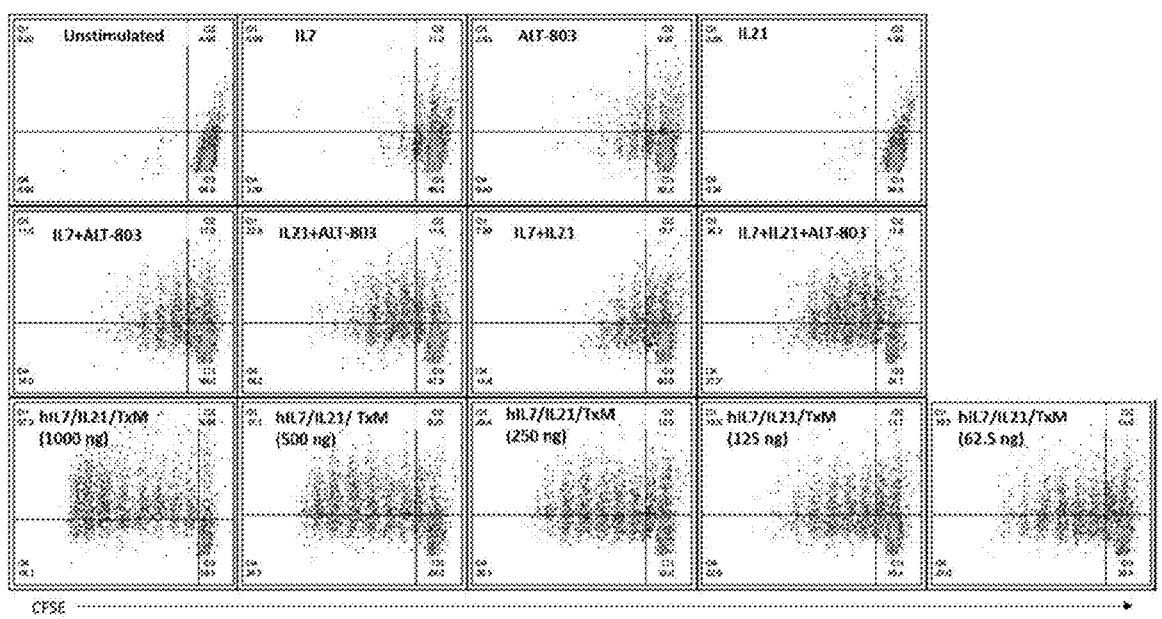
FIG. 11 are dot-plots showing proliferation of purified CSFE-labeled human T cells following stimulation with hIL7/IL21/TxM fusion protein complex or a combination of recombinant IL-7, IL-21 and ALT-803 (IL-7+IL-21+ALT-803), compared to media control. Proliferation was assessed by dilution of CFSE signal following cell division.

Similarly, enhanced proliferation of T cells was induced ex-vivo by stimulation of purified T cells with IL-7, IL-15, and IL-21. To evaluate the ability of hIL7/IL21/TxM to promote proliferation of T cells, purified CFSE-labelled human T cells (>90% CD3+, purified via RosetteSep™ Human CD8+ T Cell Enrichment Cocktail) ($1 \times 10^5$ cells/ml) were stimulated for 7 days with hIL7/IL21/TxM or the combination of separate recombinant IL-7, IL-21, and ALT-803 and cytokine-induced T cells proliferation was assessed by flow cytometer. The results indicate that hIL7/IL21/TxM complex was capable of inducing proliferation of purified T cells better than the combination of IL-7, IL-21 and IL-15 (FIG. 11).

Figure 12:
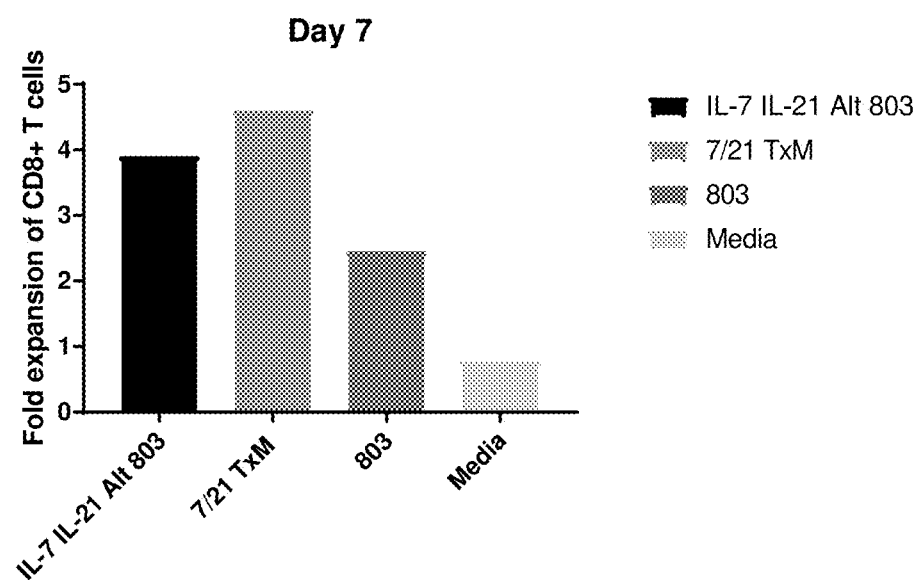
FIG. 12 is a bar graph showing the expansion of purified human CD8$^+$ T cells following incubation in media containing hIL7/IL21/TxM fusion protein complex; compared to IL-7+IL-21+ALT-803, ALT-803 alone or control media. Incubation with hIL7/IL21/TxM resulted in better expansion of CD8$^+$ T cells than was observed with IL-7+IL-21+ALT-803 combination treatment.

In further studies, Cell Trace violet-labelled human CD8+ T cells (>90% CD8+, purified via RosetteSep™ Human CD8+ T Cell Enrichment Cocktail) ($2.5 \times 10^5$ cells/ml) were stimulated with hIL7/IL21/TxM or the combination of separate recombinant IL-7, IL-21, and ALT-803. After 7 days, cells were collected for counting and staining with antibodies to determine T cell phenotype. Expansion of human CD8+ T cells was greatest following 7-day incubation with 10 nM hIL7/IL21/TxM (4.6 fold) compared to a mixture of ALT-803 (10 nM), IL-7 (25 ng/mL), and IL-21 (25 ng/mL) (3.9 fold) or ALT-803 alone (10 nM) (2.5 fold) (FIG. 12). Cells grown in media alone did not show expansion.

Figure 13:
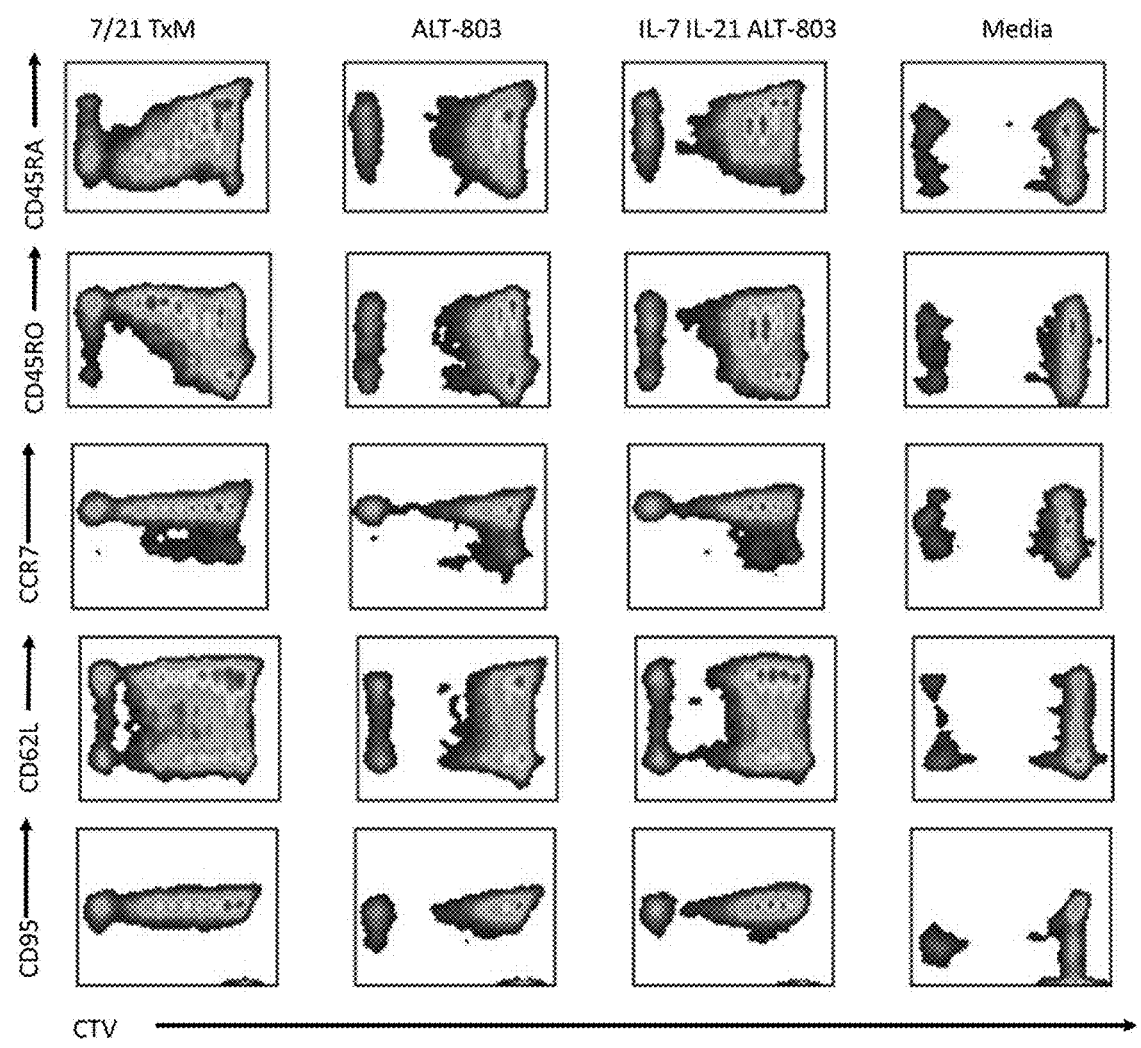
FIG. 13 are density plots showing the proliferation and phenotype of purified human CD8$^+$ T cells following incubation in media containing hIL7/IL21/TxM fusion protein complex; compared to IL-7+IL-21+ALT-803, ALT-803 alone or control media. Incubation with hIL7/IL21/TxM resulted in greater proliferation of CD8$^+$ T cells, particular m than was observed with IL-7+IL-21+ALT-803 combination treatment.

Flow cytometry was used to assess the phenotype of CD8 T cells undergoing cell proliferation as determined by Cell Trace violet dilution (i.e. decreased signal per cell with each division) (FIG. 13). The results confirm the fold expansion data such that the higher levels of cell proliferation were seen in human CD8+ T cells incubated with hIL7/IL21/TxM compared to cells grown in a mixture of ALT-803, IL-7, and IL-21 or ALT-803 alone. No proliferation was observed in cells grown in media alone. CD8+ T cells expressing CD45RO, CCR7, and CD95 show significant proliferation following incubation with hIL7/IL21/TxM. Proliferation was also observed in CD8+ T cells with low CCR7 and CD62L whereas cells with elevated CD45RA proliferated but to a lesser extent or were converted to the CD45RO phenotype following activation with hIL7/IL21/TxM. The results indicate that proliferation of CD8+ central memory T cells as well as CD8+ effector memory T cells is induced by hIL7/IL21/TxM and to a greater level than was seen with the ALT-803+IL-7+IL-21 combination.

Example 4: In Vitro Expansion of Different Subsets of Human CD8+ T Cells by hIL7/IL21/TxM Fusion Protein Complexes To assess the in vitro expansion of different subsets of human CD8+ T cells, buffy coat was received from the blood bank. Total CD8 T cells were isolated with the RosetteSep™ Human CD8 Negative-Selection Kit (STEMCELL Technologies). After enrichment of CD8 T cells, the naïve, central memory, effector memory and memory stem CD8 T cell subsets were sorted by flow cytometry using the following markers. Naïve CD8+ T cells were phenotyped as live CD8+, CCR7+, CD45RO− and CD95− cells. CD8+ T effector memory cells were phenotyped as live CD8+, CCR7−, and CD45RO+ cells. CD8+ T central memory cells were phenotyped as live CD8+, CCR7+, and CD45RO+ cells. CD8+ T memory stem cells were phenotyped as live CD8+, CCR7+, CD45RO−, and CD95+ cells. Sorted cells were checked for purity (i.e., samples were considered pure if >95% of the cells had the desired phenotype).

Sorted different population cells were labelled with CFSE (Carboxyfluorescein succinimidyl ester) (Molecular Probes) as per manufacturer's instruction. The CFSE labelled CD8+ T cell subsets were stimulated with either media alone, IL-7+IL-21 (25 ng each), IL7 (25 ng)+ALT-803 (144 ng), IL21 (25 ng)+ALT-803 (144 ng), IL7 (25 ng)+IL21 (25 ng)+ALT-803 (144 ng) or hIL7/IL21/TxM (1.4 µg) in 200 µL of media in a 96-well flat bottom plate at 37° C., 5% $CO_2$. After day 7, the cells were harvested from the wells by washing the wells four times with 2% FBS-PBS and collecting the washes in a tube. The harvested cells were further washed once with 2% FBS-PBS by centrifugation at 1500 RPM for 5 mins. Cells were resuspended in 100 µL of % FBS-PBS and from that 10 µL was used for counting cells by hemocytometer following a 1:1 dilution with 0.4% Trypan Blue. Cell numbers were determined to assess expansion of the purified CD8+ T cell subsets following 7-day incubation with the cytokines or hIL7/IL21/TxM complex. The results indicate that treatment with hIL7/IL21/TxM fusion complexes was capable of increasing expansion of naïve, central memory, effector memory and memory stem CD8+ T cell subsets compared incubation to media alone or to combinations of two of the tested cytokines. Moreover, hIL7/IL21/TxM complex was more effective than the combination of IL-7, IL-21 and ALT-803 at expanding the populations of CD8+ T cell central memory and effector memory subsets (FIGS. 14A-14D), consistent to the results seen with unsorted human CD8+ T cells.

Figure 15:
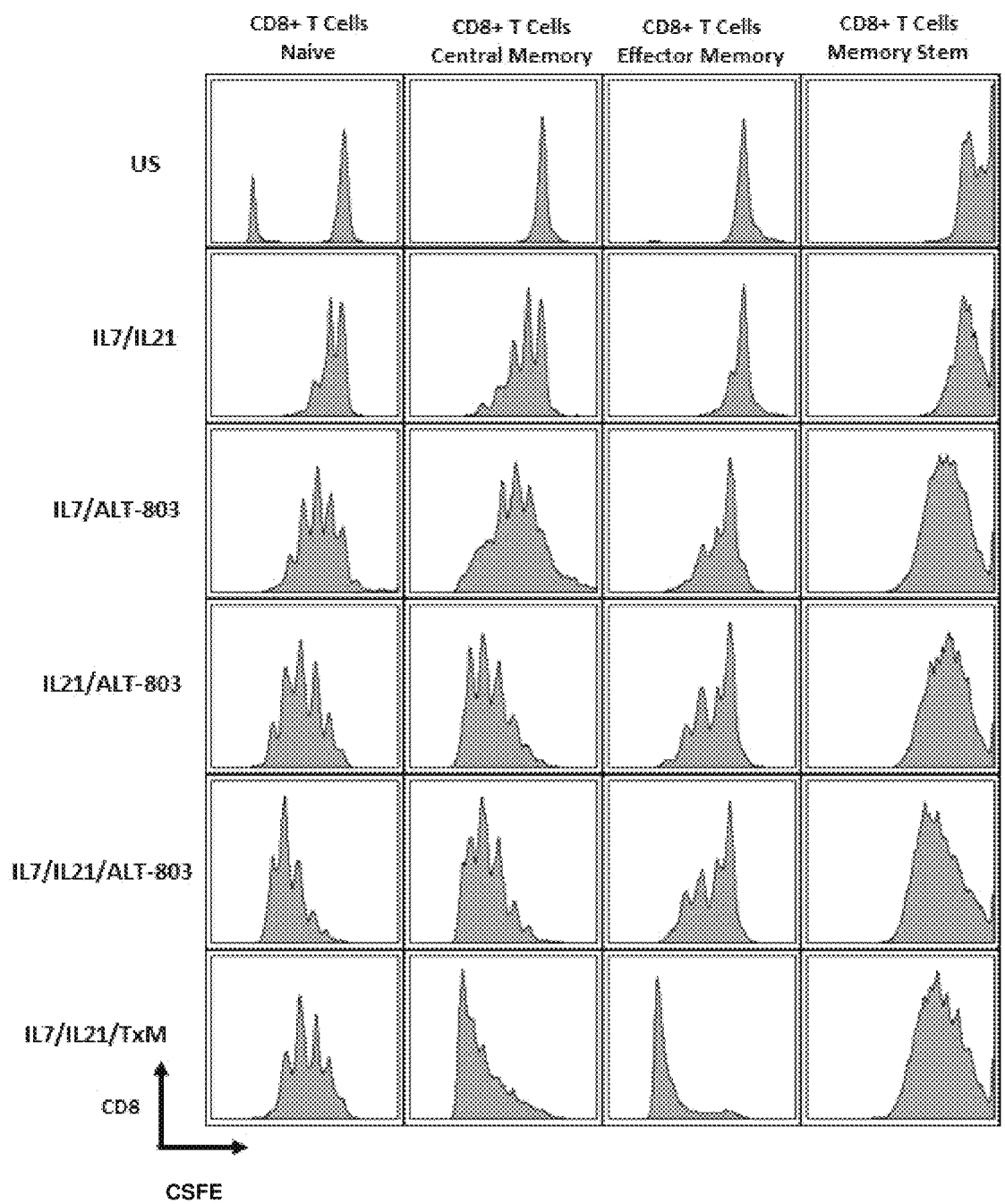
FIG. 15 shows line graphs (flow cytometry histograms) showing the proliferation of purified human CD8$^+$ T cell subsets following incubation in media containing hIL7/IL21/TxM fusion protein complex, compared to control media (US), IL-7+IL-21, IL-7+ALT-803, IL-21+ALT-803, or IL-7+IL-21+ALT-803 combinations. Incubation with hIL7/IL21/TxM resulted in proliferation of naïve, central memory, effector memory and memory stem CD8$^+$ T cell subsets compared to media controls. Greater proliferation of central memory and effector memory CD8$^+$ T cell subsets was seen with hIL7/IL21/TxM than any other combination of individual cytokines.

In addition to expansion, proliferation of the human CD8+ T cell subsets was assessed based on CSFE dilution by flow cytometry. For this analysis, the remaining cells were washed once with 1 ml FACS buffer and cells were stained with anti-CD45RO, CD95, CCR7 and CD8 antibodies (2 µL per sample for 30 minutes in FACS buffer). After 30 minutes at room temperature in the dark, the cells were washed with 1 mL FACS buffer and resuspended in 300 µL FACS buffer. Cells were analyzed by flow cytometry gated for different subsets of population. Naïve CD8+ T cells were phenotyped as live CD8+, CCR7+, CD45RO− and CD95− cells. CD8+ T effector memory cells were phenotyped as live CD8+, CCR7−, and CD45RO+ cells. CD8+ T central memory cells were phenotyped as live CD8+, CCR7+, and CD45RO+ cells. CD8+ T memory stem cells were phenotyped as live CD8+, CCR7+, CD45RO−, and CD95+ cells. Each population was evaluated for proliferation based on CSFE dilution. See FIG. 15. This study verified that proliferation of each human CD8 T cell subset was induced by hIL7/IL21/TxM compared to little or no proliferation observed in the media control cells. Highest levels of cell proliferation were seen in the CD8+ T cell central memory and effector memory subsets following incubation with hIL7/IL21/TxM compared to all other conditions including the ALT-803+IL-7+IL-21 combination.

Example 5: Enhanced Proliferation, Cytotoxicity and Activation of Purified NK Cells Following Stimulation with hIL7/IL21/TxM Fusion Protein Complexes The ability of hIL7/IL21/TxM to affect proliferation and activation of human NK cells was also evaluated. NK cells were purified human leukocytes using the StemCell RosetteSep™ Human NK Cell Enrichment Cocktail. Purified NK cells (>90% purity) were seeded at $2 \times 10^6$ cells/mL in 24 well plate in media containing 50 nM hIL7/IL21/TxM, 50 nM hIL18/IL12/TxM (control) or 10 nM ALT-803 (control). After 3 days, cells were counted and reseeded at $0.5 \times 10^6$ cells/mL with media containing either 10 nM hIL7/IL21/TxM or 10 nM ALT-803 (control). After an additional 3 days, cells were again reseeded at $0.5 \times 10^6$ cells/mL with media containing either 10 nM hIL7/IL21/TxM or 10 nM ALT-803 (control). On day 10, cells were harvested, assessed for proliferation and cell phenotype and tested for cytotoxicity against K562 target cells.

Figure 16:
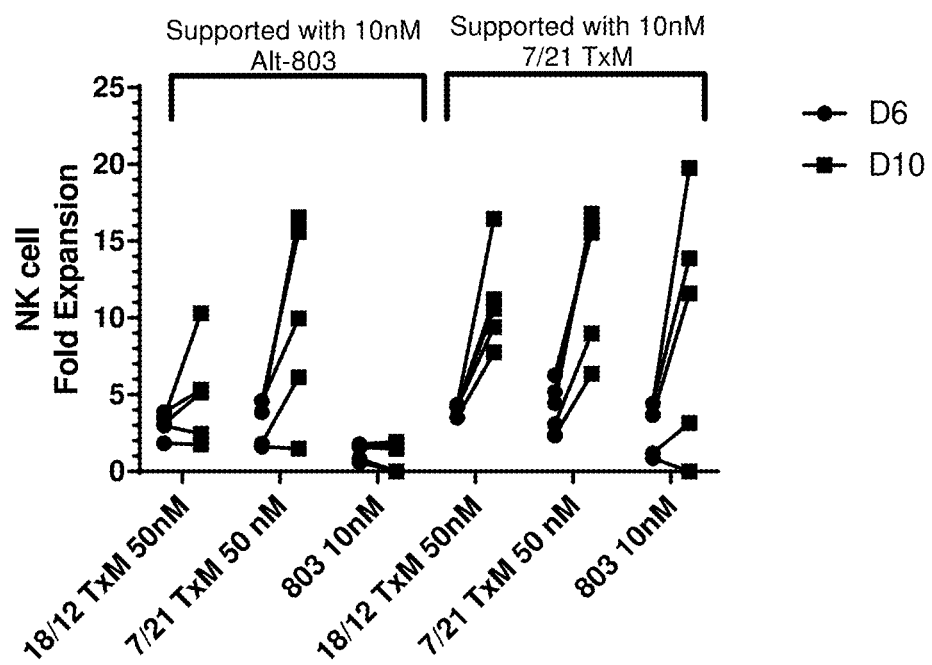
FIG. 16 is a line graph illustrating the proliferation of purified human NK cells mediated by hIL7/IL21/TxM fusion protein complex compared to ALT-803. The lines represent NK cells isolated from different donors.
Figure 17:
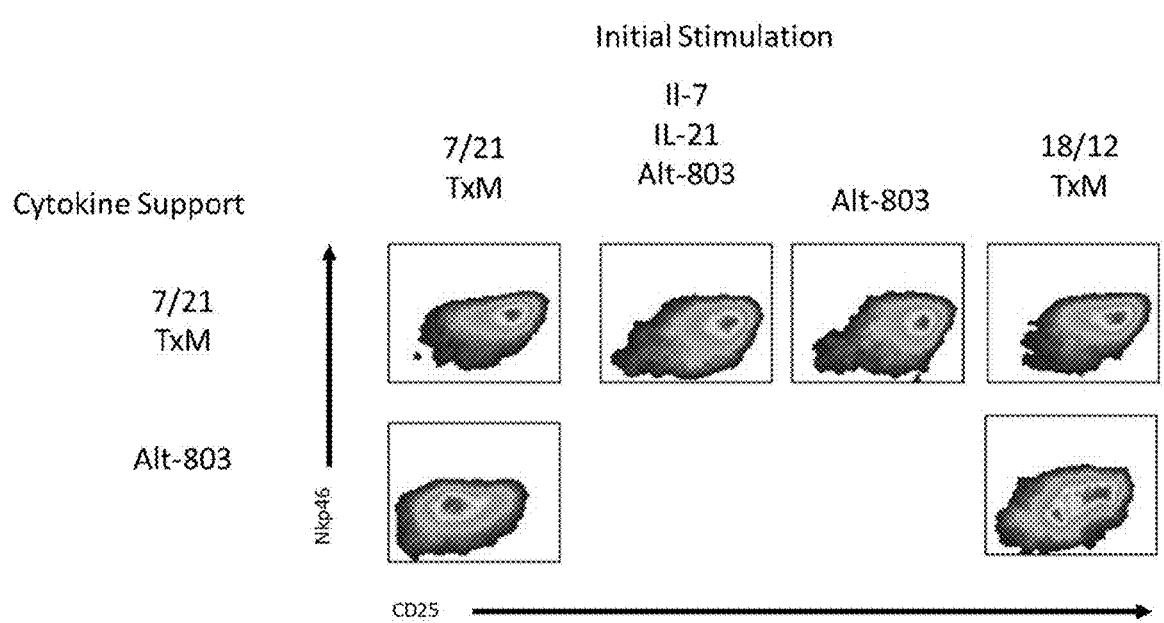
FIG. 17 are density plots showing the phenotype of purified human NK cells following incubation in media containing hIL7/IL21/TxM fusion protein complex; compared to IL-7+IL-21+ALT-803, ALT-803 alone or hIL18/IL12/TxM fusion protein complex containing media.

The results of this study indicated that hIL7/IL21/TxM provided better cytokine support (day 4-10) for expansion of purified human NK cells than ALT-803 regardless of the cytokine used for initial stimulation (day 1-3), such that a majority of the NK cell cultures showed greater than a 10-fold expansion by day 10 following growth from day 4-10 in media containing hIL7/IL21/TxM (FIG. 16). Based on flow cytometry staining with NKp46 and CD25 antibodies, the hIL7/IL21/TxM-supported NK cells showed an activated CD25+ phenotype comparable to the cytokine-induced memory-like (CIMK) NK cells observed following short term incubation with hIL18/IL12/TxM followed by ALT-803 cytokine support (FIG. 17).

Figure 18:
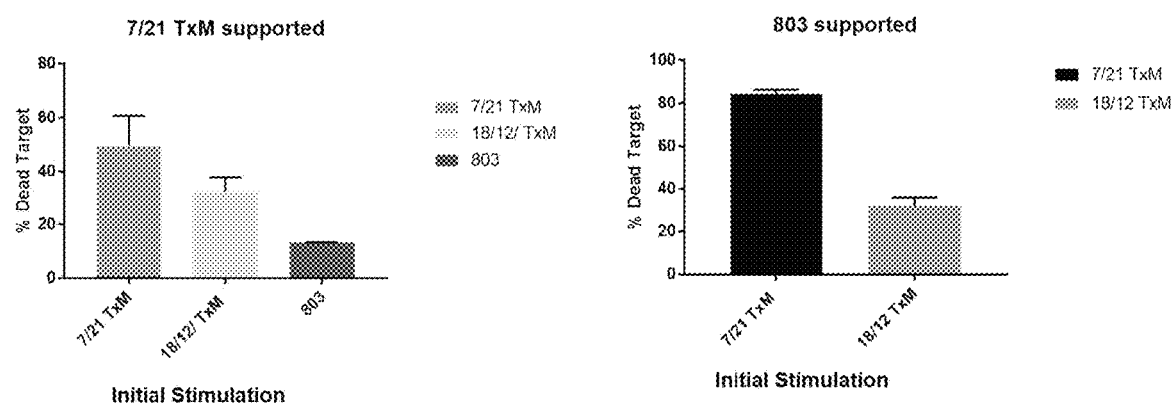
FIG. 18 are bar graphs showing levels of K562 target cell killing mediated by purified human NK cells following incubation in media containing hIL7/IL21/TxM fusion protein complex; compared to IL-7+IL-21+ALT-803, ALT-803 alone or hIL18/IL12/TxM fusion protein complex containing media.

The cytotoxic activity of these cells was assessed in 4 hour killing assays with K562 target cells. Briefly, K562 target cells were labeled with Celltrace violet (CVT) and then co-cultured with expanded human NK effector cells at a ratio of 2.5:1 (effector:target) for 4 hours. Cells are harvested washed and resuspended in RPMI containing 2 µg/mL propidium iodide. Tumor cell lysis was measured by co-staining of propidium iodide and CTV. Percent specific killing is calculated by subtracting the any background death of K562 cells measured from wells that were not co-cultured with NK cells. Human NK cells provided an initial 3-day stimulation with hIL7/IL21/TxM followed by cytokine support with either hIL7/IL21/TxM or ALT-803 showed better cytotoxicity against K562 cells than those receiving initial hIL18/IL12/TxM stimulation with followed by hIL7/IL21/TxM or ALT-803 cytokine support (FIG. 18). This result was surprising since the activation phenotype of these cells appeared to be comparable based on CD25 staining. Together these findings indicate that hIL7/IL21/TxM is highly effective at inducing human NK cell proliferation resulting in an activated phenotype with elevated cytotoxic activity.

Figure 19:
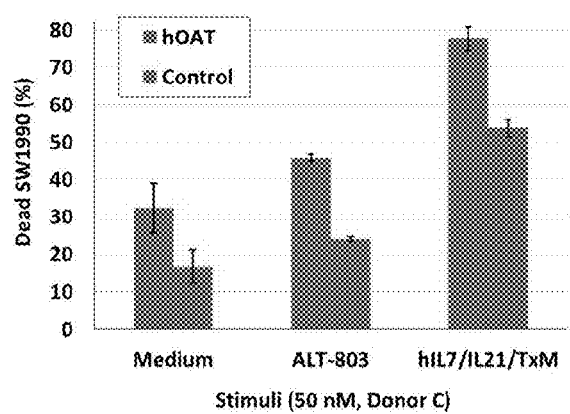
FIG. 19 are bar graphs showing levels of human NK cell cytotoxicity and NK-mediated antibody dependent cellular cytotoxicity (ADCC) against pancreatic tumor cell targets induced by hIL7/IL21/TxM fusion protein complex; compared to ALT-803 or control media. Data from NK cells isolated 2 different donors is shown.
Figure 19:
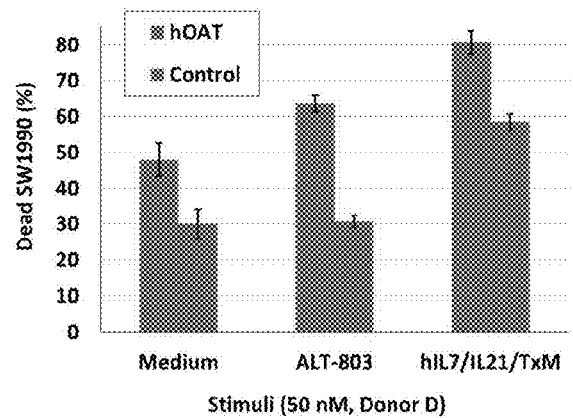

Additional studies were conducted to further characterize the ability of hIL7/IL21/TxM to induce NK cell cytotoxicity against human tumor cells. Purified human fresh NK cells from 2 different donors were mixed with CellTrace violet-labeled human TF-positive pancreatic cancer SW1990 cells for 40 hrs at an effector:target ratio (E:T) of 2:1. ALT-803 or hIL7/IL21/TxM at 50 nM was added to activate the human NK cells and media alone served as a control. In some cultures, humanized anti-human tissue factor antibody IgG1 (hOAT) was added at 0.1 nM to induce ADCC. At the end of the incubation period, the percentage of dead violet-labeled SW1990 cells was determined by staining with propidium iodide followed by flow cytometry (FIG. 19). Following stimulation with hIL7/IL21/TxM alone, human NK cells exhibited significant cytotoxicity against SW1990 tumor cells compared to ALT-803 or control media. These results are consistent with the enhanced cytotoxicity observed with hIL7/IL21/TxM-stimulated NK cell against K562 targets. Addition of anti-TF antibody resulted in a further increase in NK-mediated ADCC of the TF-positive tumor cell, again with NK cells stimulated with hIL7/IL21/TxM showing the highest cytotoxicity. These findings indicate that hIL7/IL21/TxM provides potent activation of human NK cells resulting in enhanced natural killing and ADCC against tumor cells.

Figure 20:
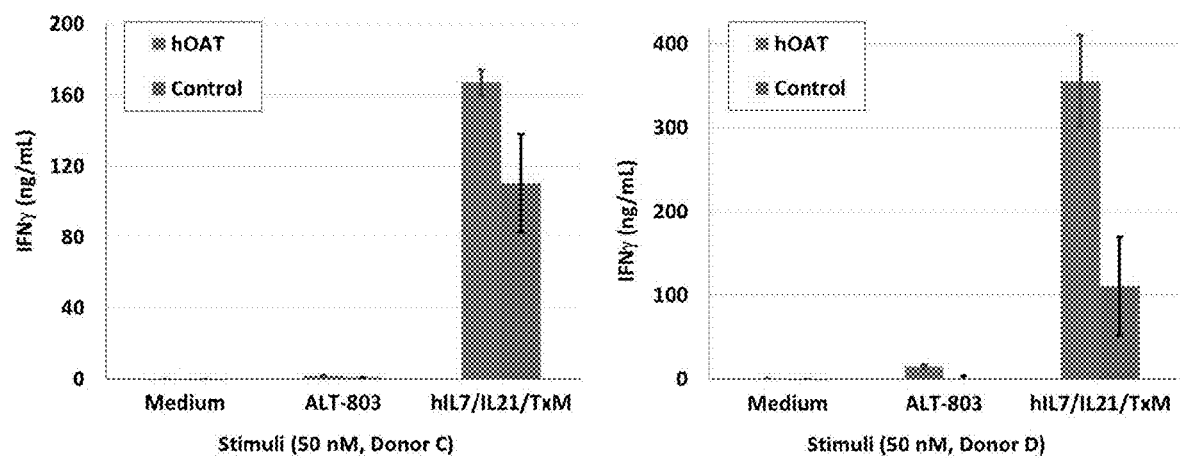
FIG. 20 are bar graphs showing levels of IFNγ released by human NK cells in response to hIL7/IL21/TxM fusion protein complex; compared to ALT-803 or control media. Data from NK cells isolated 2 different donors is shown.

To assess the potential mechanism of action of hIL7/IL21/TxM, levels of IFNγ were determine by ELISA using the supernatant of the NK cell/SW1990 tumor cell cultures described above. Elevated levels of IFNγ were found in the NK cell/SW1990 cell cultures containing hIL7/IL21/TxM whereas little or no IFNγ was seen in the ALT-803 or control media conditions (FIG. 20). IFNγ release was further induced by addition of the anti-TF antibody to the hIL7/IL21/TxM stimulated cells, but to a much lesser degree or not at all in the ALT-803 or control media conditions. The results indicate that hIL7/IL21/TxM is highly effective at inducing NK cell IFNγ production, which can be further elevated by addition of ADCC antibodies.

Figure 21:
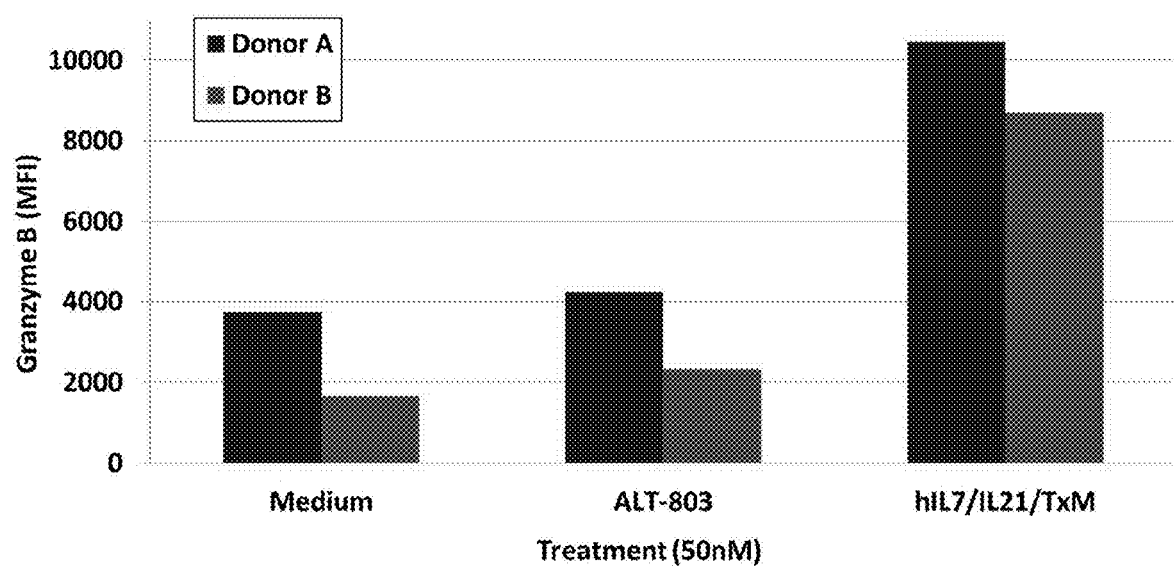
FIG. 21 is a bar graph showing levels of granzyme B expressed by human NK cells in response to hIL7/IL21/TxM fusion protein complex; compared to ALT-803 or control media. Data from NK cells isolated 2 different donors is shown.
Figure 23A:
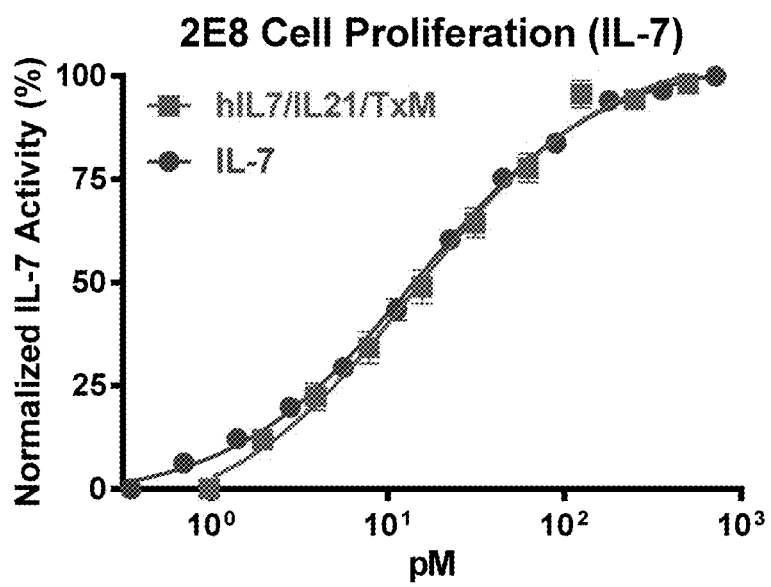
FIGS. 23A-23C are a series of graphs showing that hIL7/IL21/TxM induces specific activation of IL-7 (FIG. 23A), IL-21 (FIG. 23B) and IL-15 (FIG. 23C) receptors.
Figure 23B:
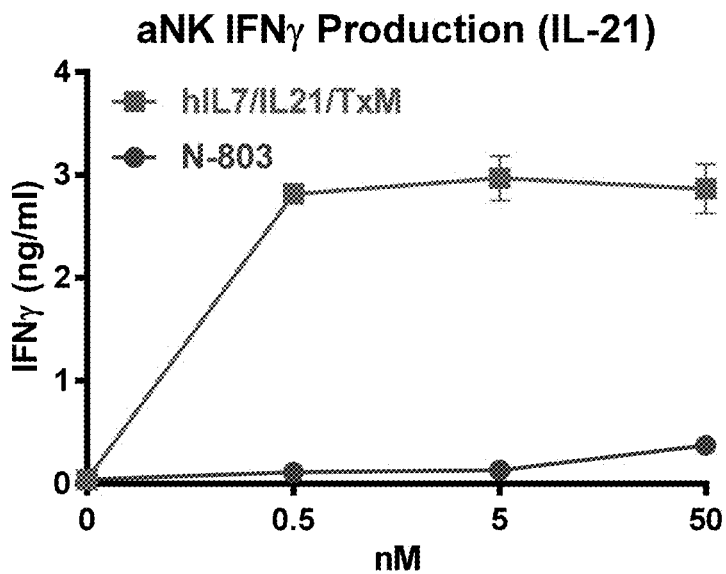
Figure 23C:
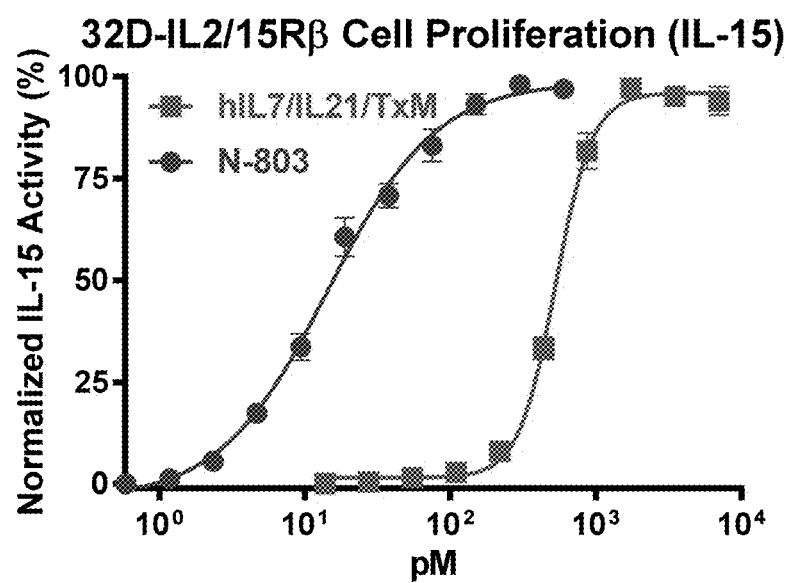
Figure 24:
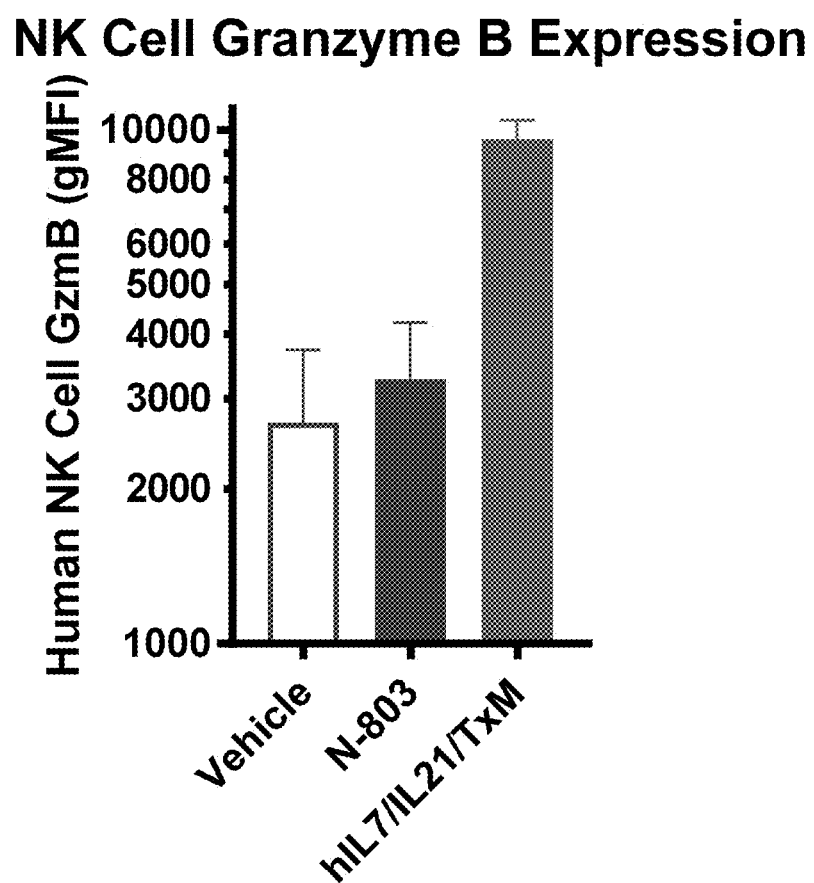
FIG. 24 is a graph demonstrating the enhancement of granzyme B expression in human NK cells induced by hIL7/IL21/TxM. Granzyme B expression in pre-activated human NK cells (16 h, 50 nM, n=2).
Figure 25A:
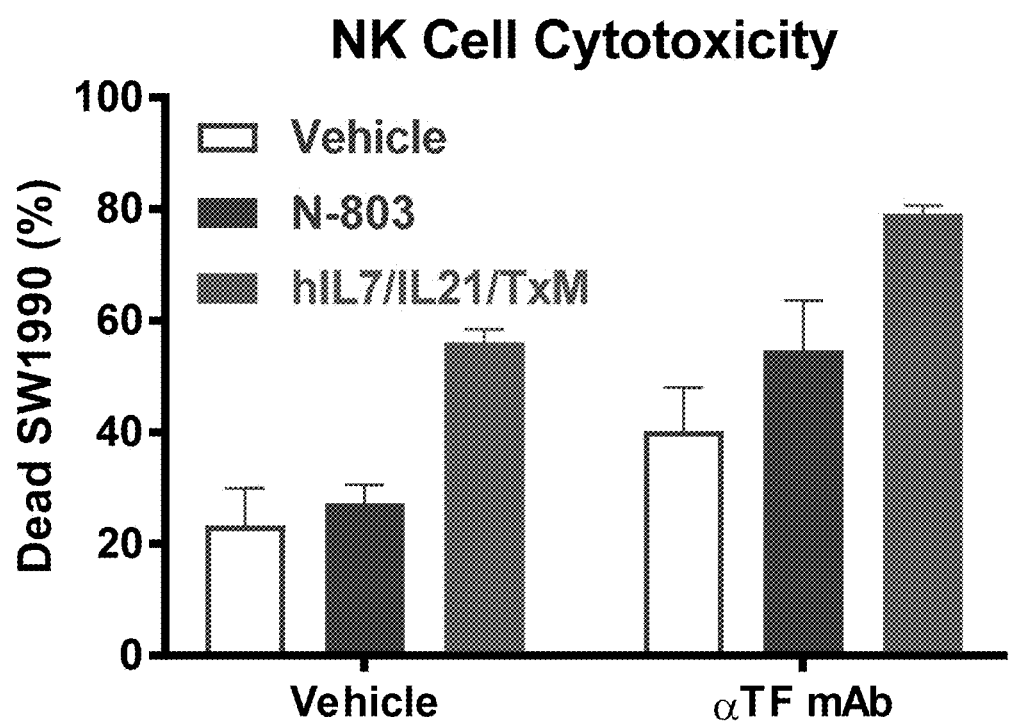
FIGS. 25A, 25B are graphs demonstrating the cytotoxicity and ADCC activity of hIL7/IL21/TxM-activated human NK cells against SW1990 pancreatic cancer cells. Fresh NK cells were mixed with SW1990 cells for 40 h at E:T of 2:1. αTF=0.1 nM. N-803 or hIL7/IL21/TxM=50.
Figure 25B:
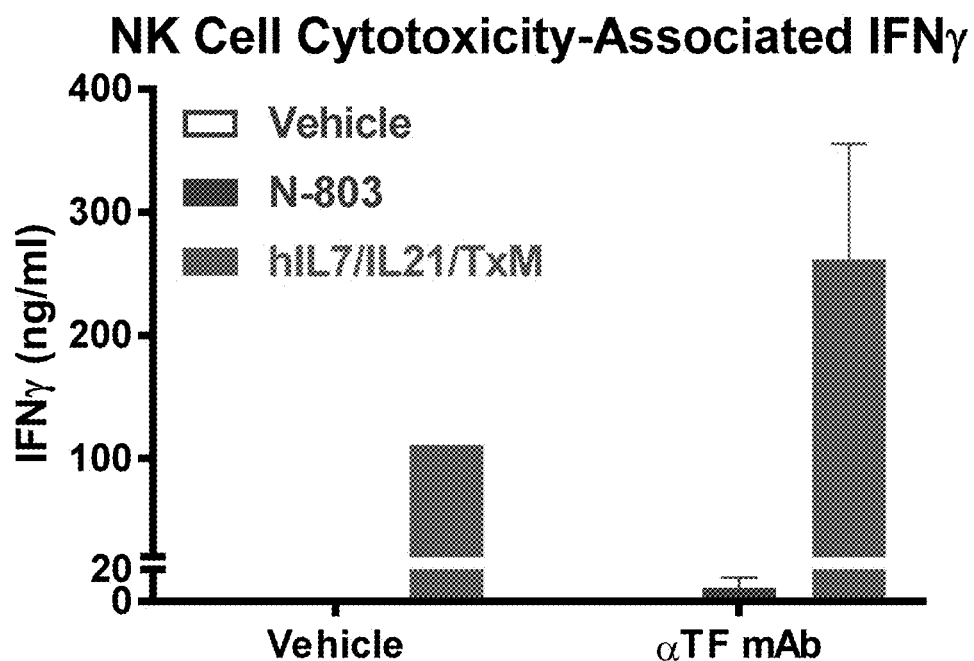
Figure 26:
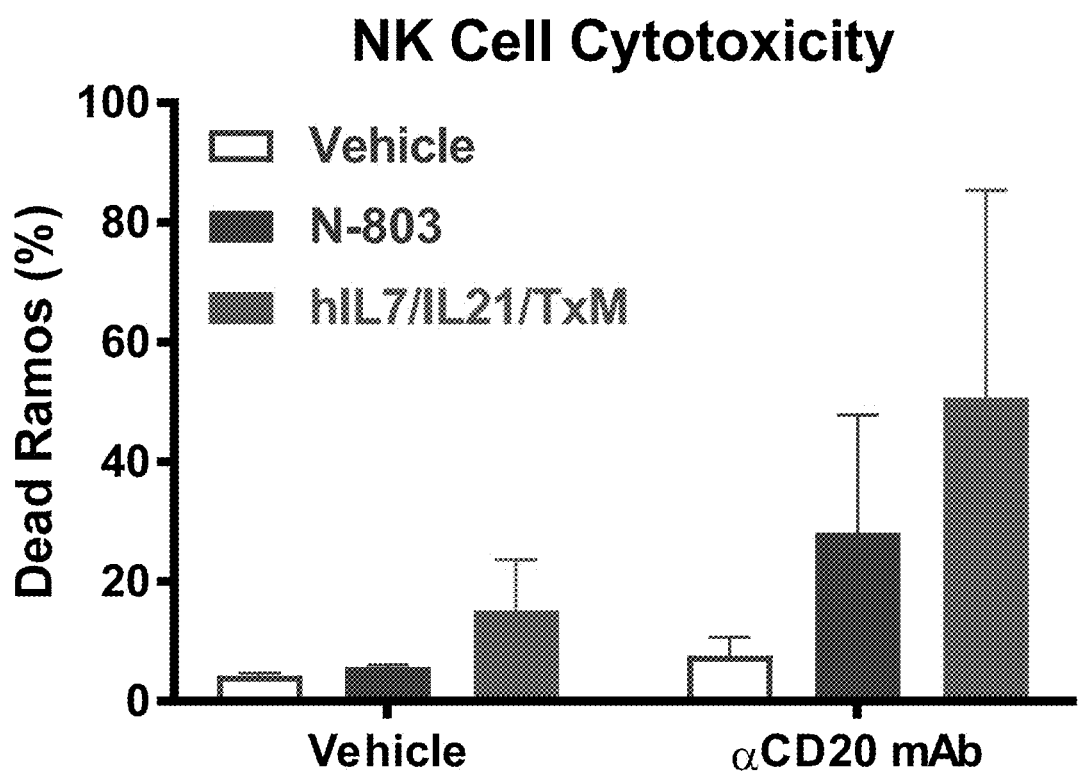
FIG. 26 is a graph demonstrating the cytotoxicity and ADCC activity of hIL7/IL21/TxM-activated human NK cells against Ramos lymphoma cells. Fresh NK cells were mixed with Ramos cells for 40 h at E:T of 1:1. αCD20=1 nM. N-803 or hIL7/IL21/TxM=0.5 nM. To show n=2.
Figure 29A:
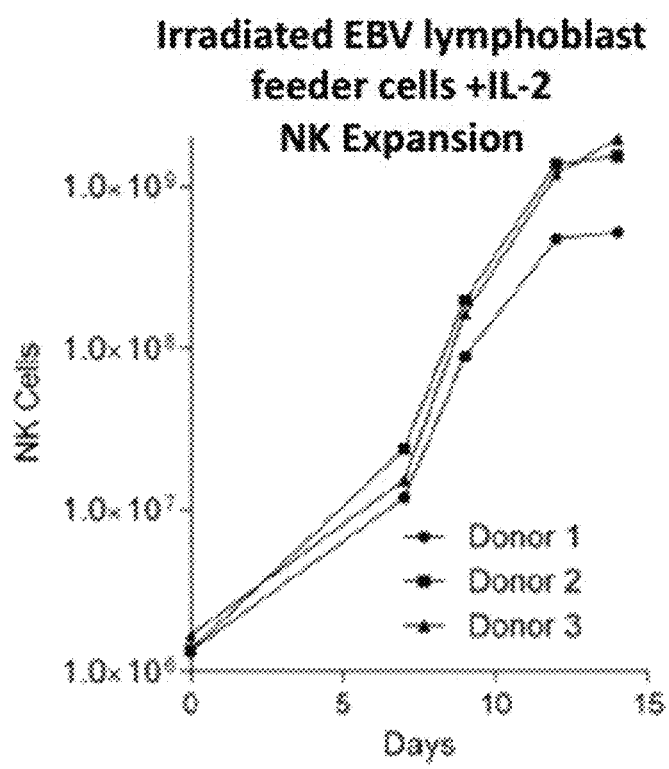
FIGS. 29A-29C are a series of graphs comparing hIL7/IL21/TxM to other ex vivo NK expansion methods.
Figure 29B:
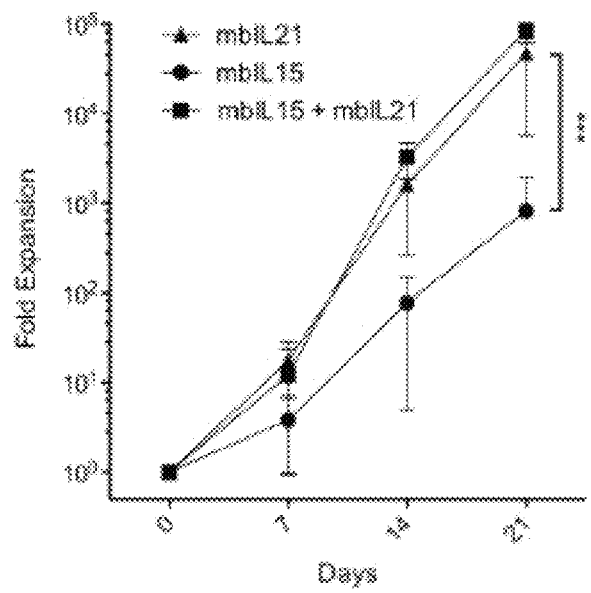
Figure 29C:
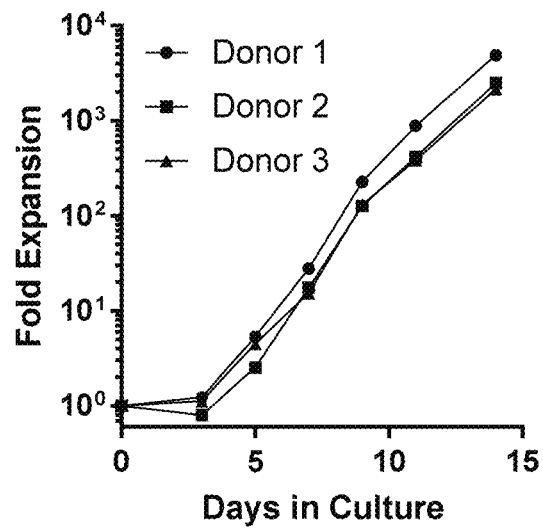
Figure 30A:
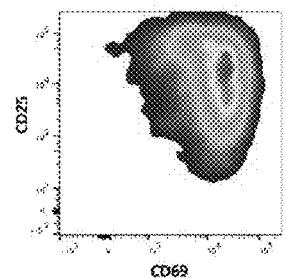
FIGS. 30A-30D is a series of density plots showing the NK cell phenotype following hIL7/IL21/TxM expansion.
Figure 30B:
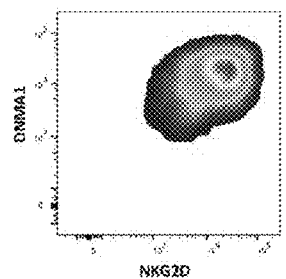
Figure 30C:
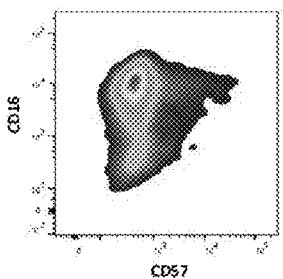
Figure 30D:
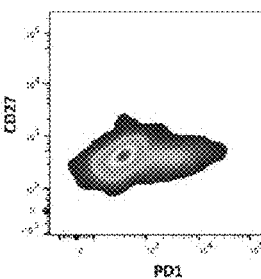
Figure 31A:
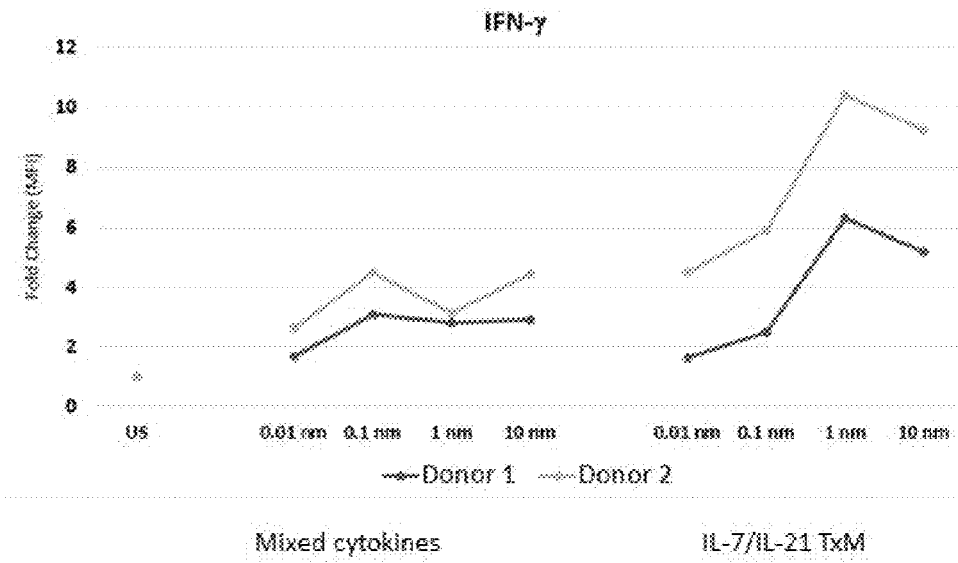
FIGS. 31A-31C are graphs demonstrating that hIL7/IL21/TxM induces IFNγ (FIG. 31A), granzyme (FIG. 31B), and perforin (FIG. 31C) in NK cells. hIL7/IL21/TxM-expanded NK cells were stimulated by separate cytokines or TxM overnight.
Figure 31B:
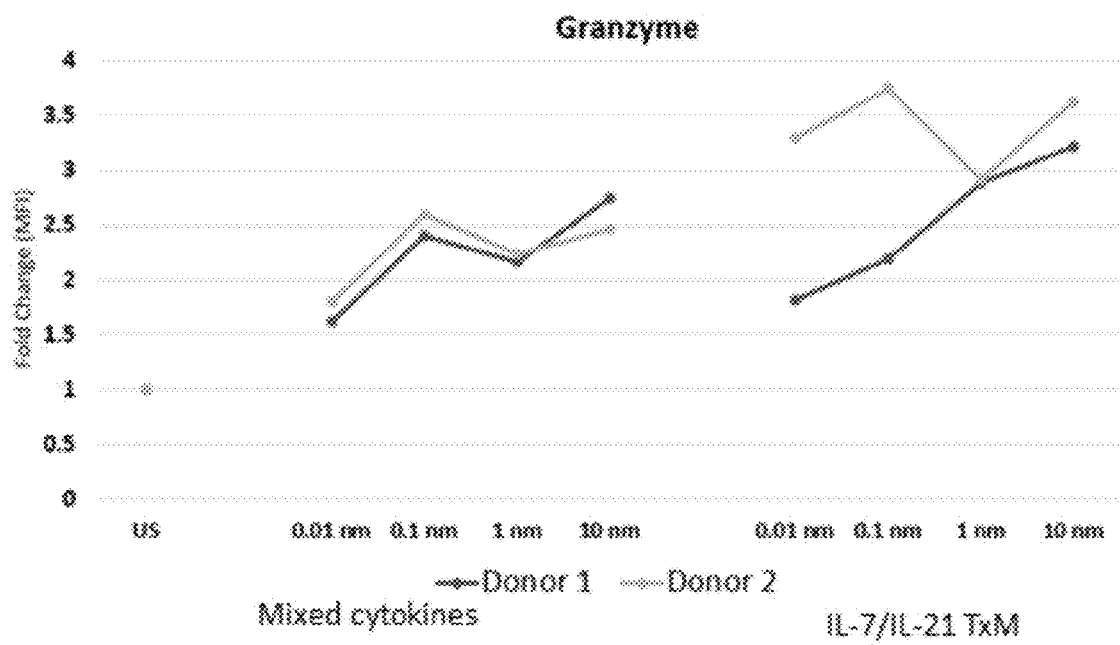
Figure 31C:
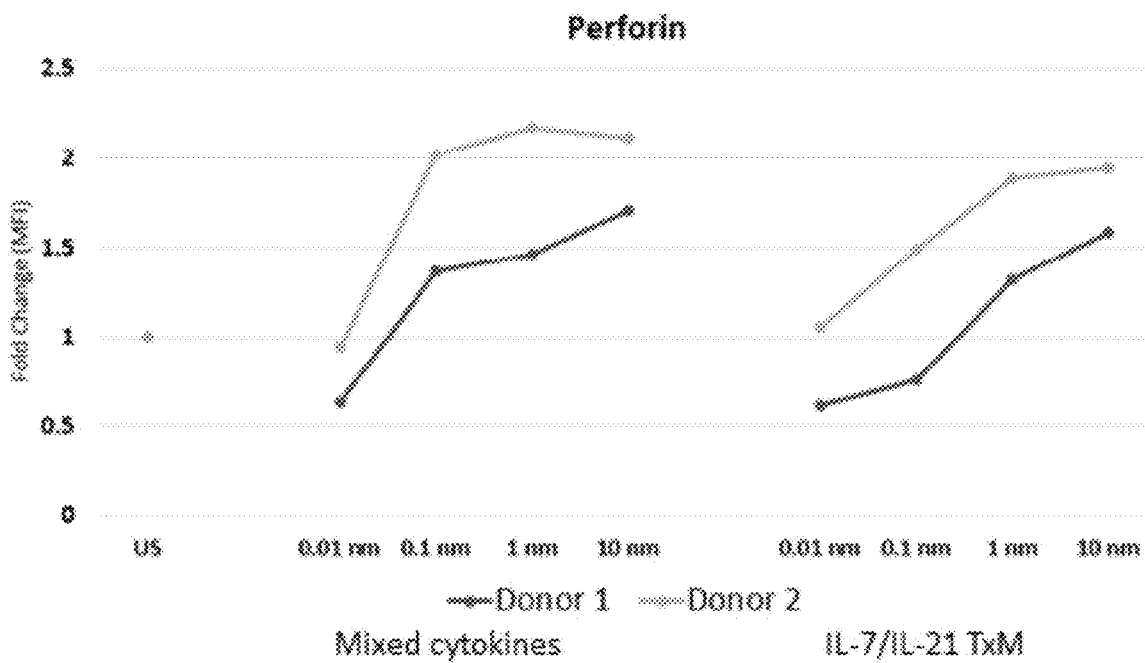
Figure 32:
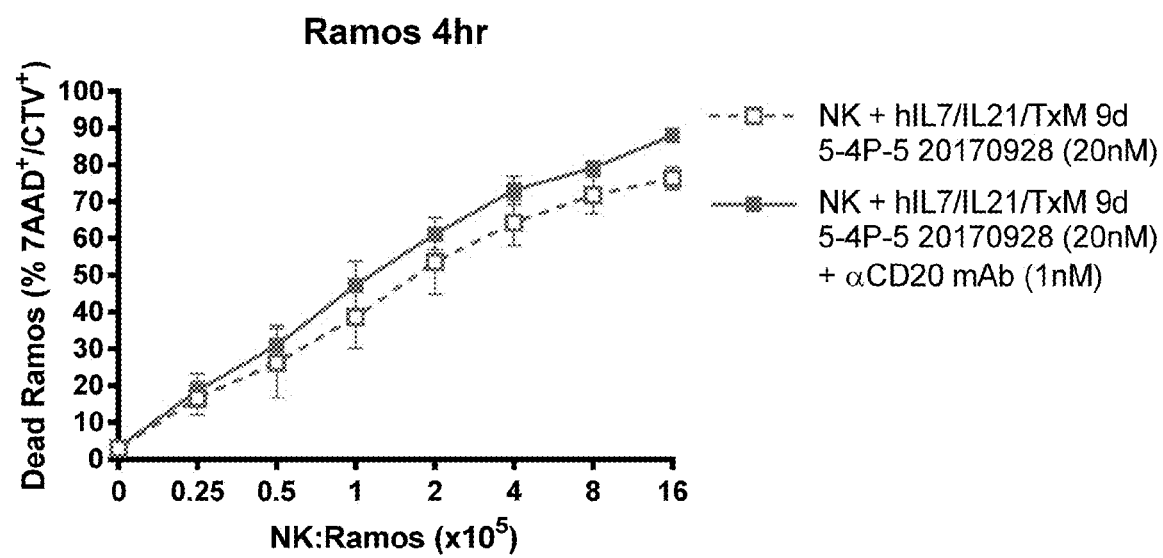
FIG. 32 is a graph demonstrating the direct and antibody-mediated cytotoxicity of hIL7/IL21/TxM-expanded NK cells: 9 days. Purified human NK cells ($0.5\times10^6$/ml) were expanded with 20 nM hIL7/IL21/TxM for 9 d, washed once, and mixed with CellTrace Violet labeled $CD20^+$ Ramos Burkitt's lymphoma cells ($10^5$) for 4 hr, followed by flow cytometry analysis in the presence of 7-AAD viability reagent.
Figure 34A:
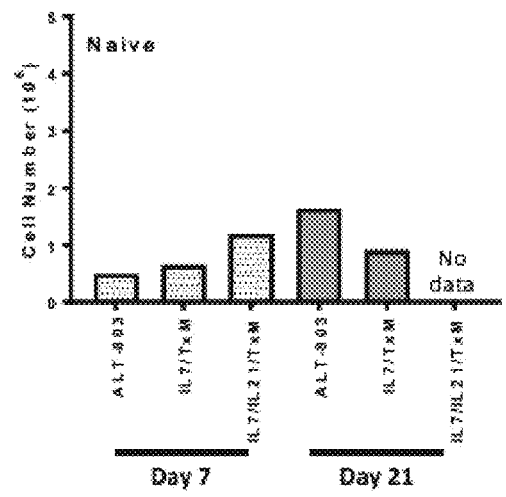
FIGS. 34A-34D depicts a series of graphs demonstrating that hIL7/IL21/TxM effectively expands sorted $CD8^+$ T cell populations following brief exposure to αCD3/CD28 beads.
Figure 34B:
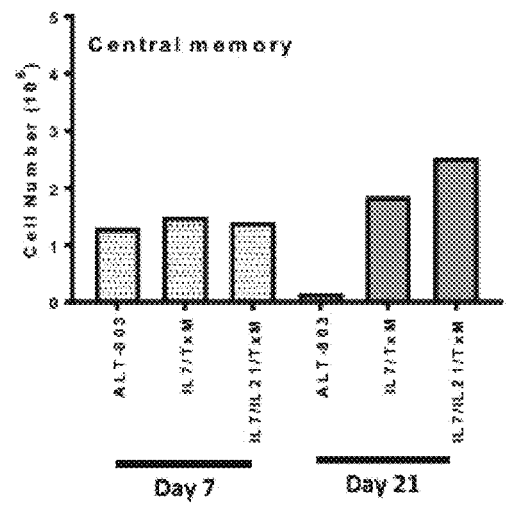
Figure 34C:
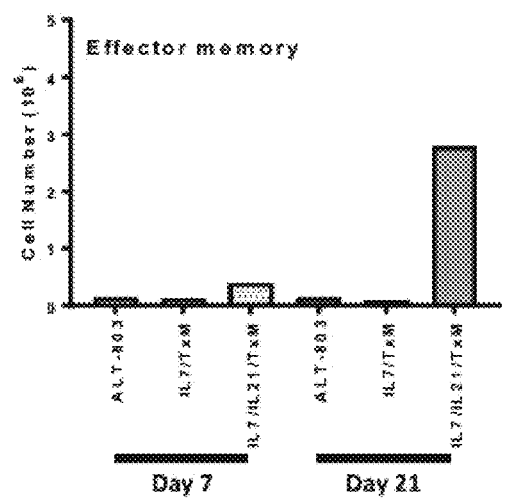
Figure 34D:
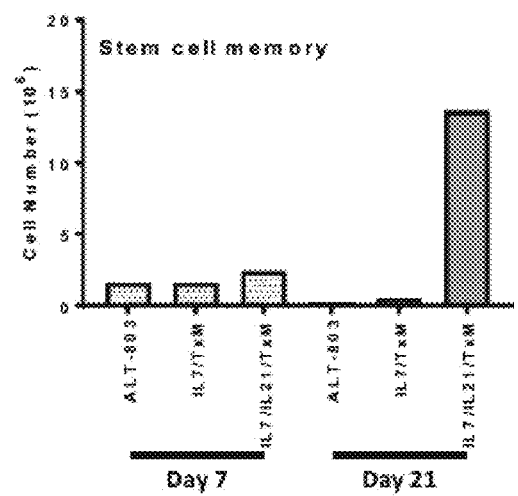
Figure 35:
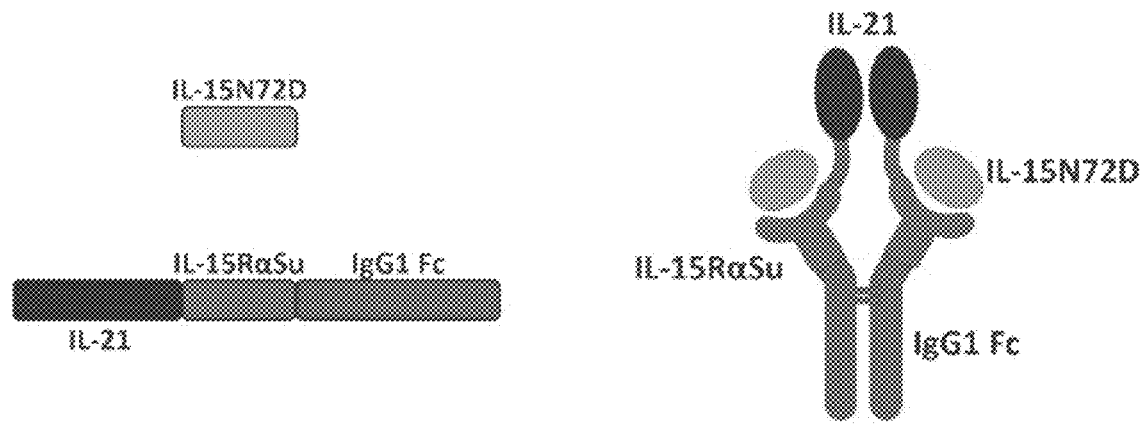
FIG. 35 is a schematic representation of h2*IL21/TxM (IL15N72D:IL21-IL15RαSuFc).
Figure 36A:
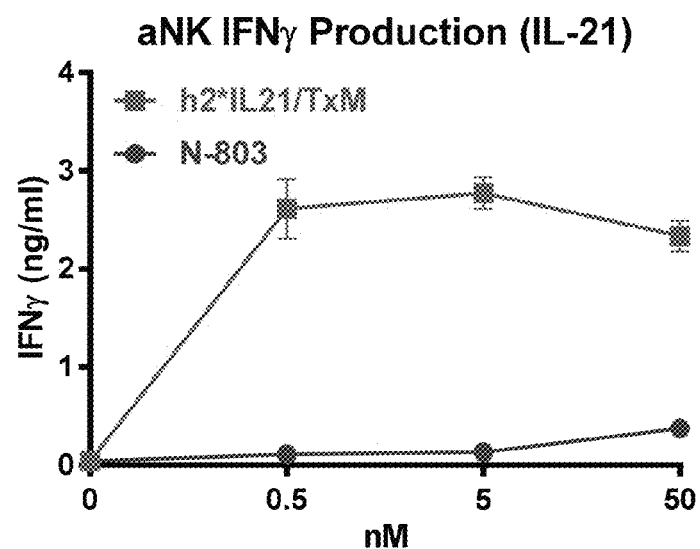
FIGS. 36A and 36B are graphs demonstrating that h2*IL21/TxM induces specific activation of IL-21 (FIG. 36A) and IL-15 (FIG. 36B) receptors.
Figure 36B:
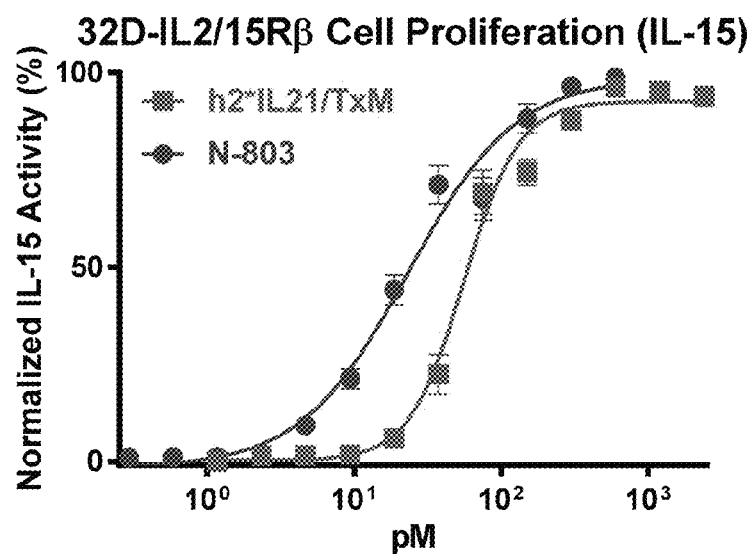
Figure 37:
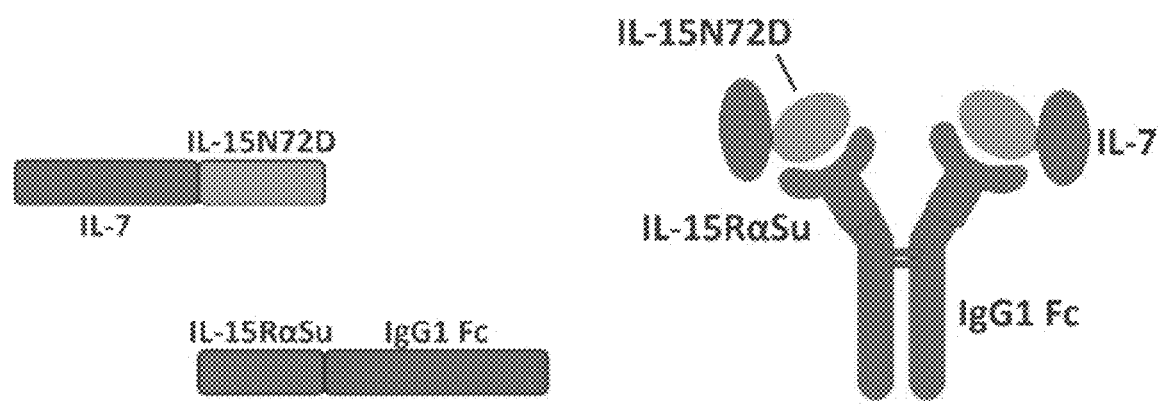
FIG. 37 is a schematic representation of h2*IL7(IL15)/TxM (IL7-IL15N72D:IL15RαSuFc).
Figure 38A:
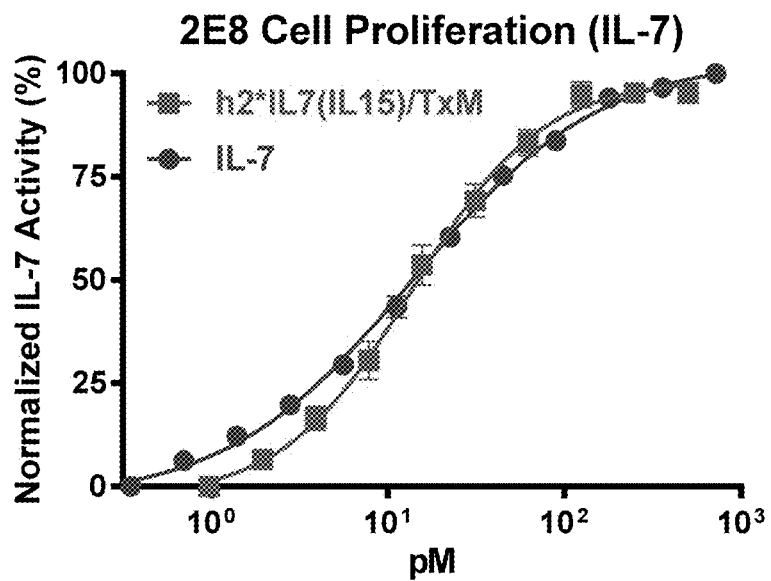
FIGS. 38A-38C are graphs showing that h2*IL7(IL15)/TxM induces specific activation of IL-7 (FIG. 38A) and IL-15 (FIG. 38C) receptors.
Figure 38B:
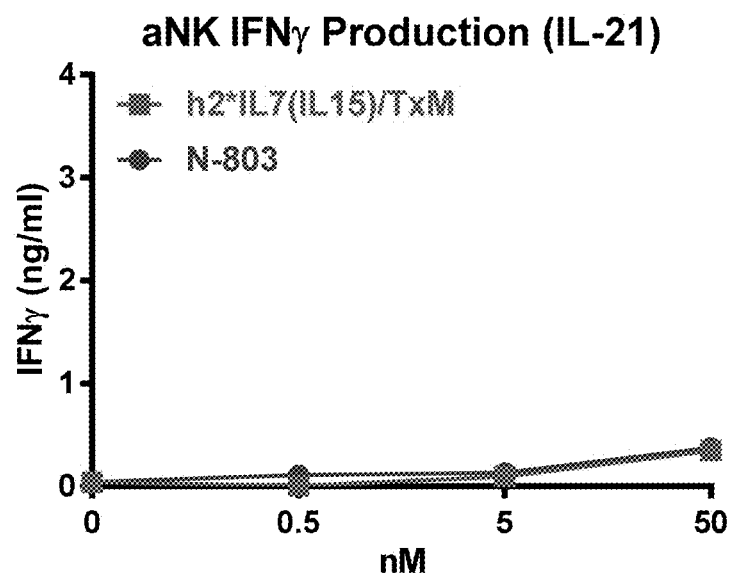
Figure 38C:
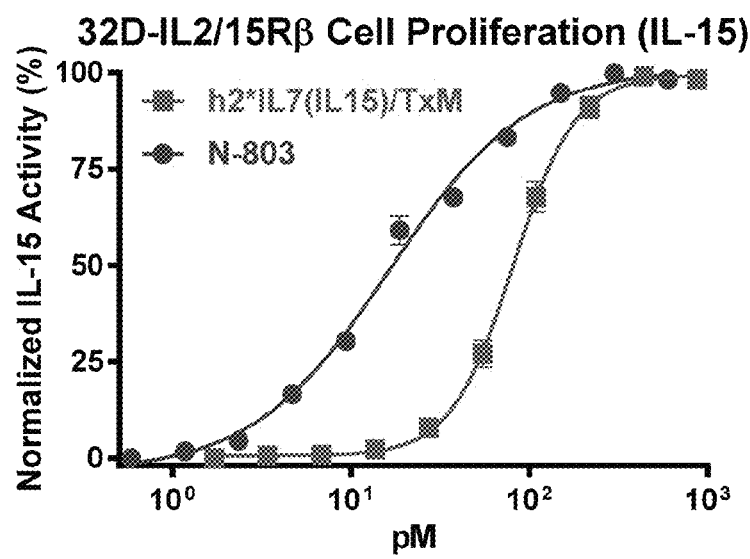
Figure 39:
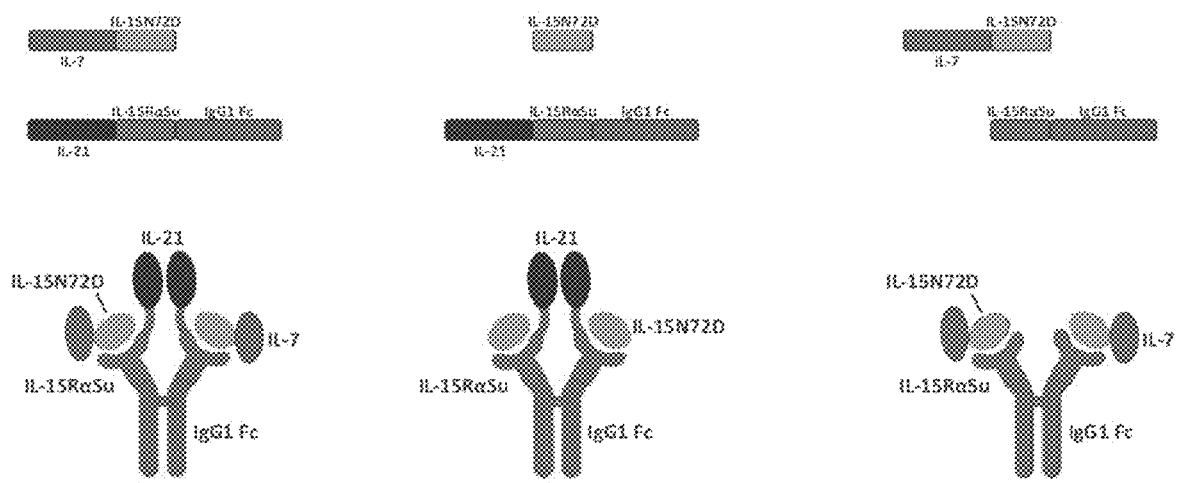
FIG. 39 is a schematic representation showing a comparison of the structures of hIL7/IL21/TxM vs. h2*IL21/TxM vs. h2*IL7(IL15)/TxM.
Figure 40A:
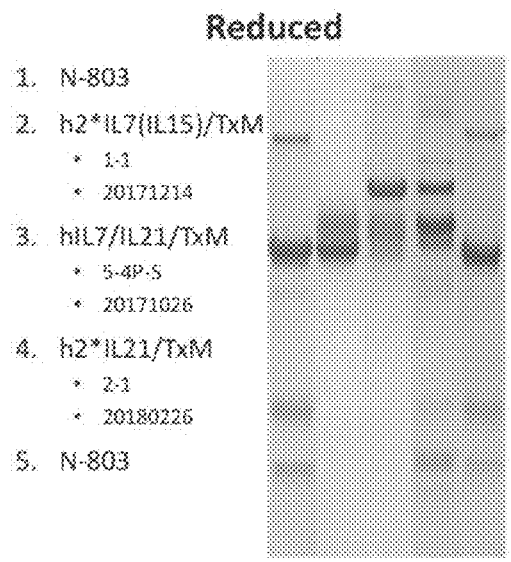
FIGS. 40A-40B show hIL7/IL21/TxM vs. h2*IL21/TxM vs. h2*IL7(IL15)/TxM run on gels under reduced (FIG. 40A) and non-reduced (FIG. 40B) conditions.
Figure 40B:
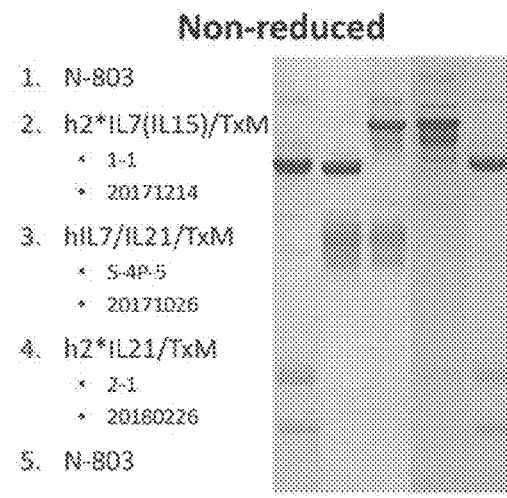
Figure 41:
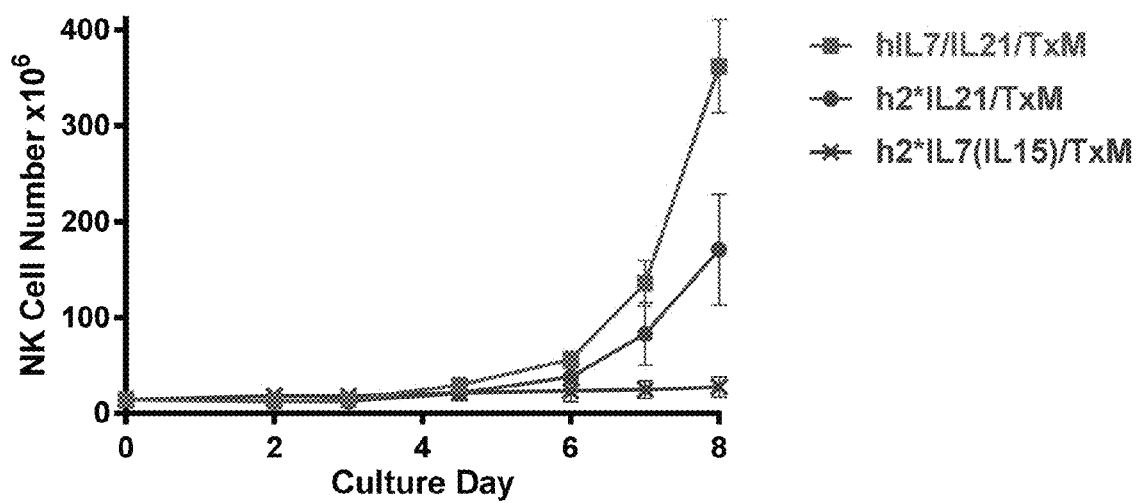
FIG. 41 is a graph demonstrating NK cell expansion stimulated with hIL7/IL21/TxM vs. h2*IL21/TxM vs. h2*IL7(IL15)/TxM. Purified human NK cells were stimulated with 19.4 nM hIL7/IL21/TxM, h2*IL21/TxM, or hIL7(IL15)/TxM, and cell number was maintained between 0.5-$2\times10^6$/ml. Cell number assessed with Vi-CELL XR. n=2 from 1 experiment.
Figure 42:
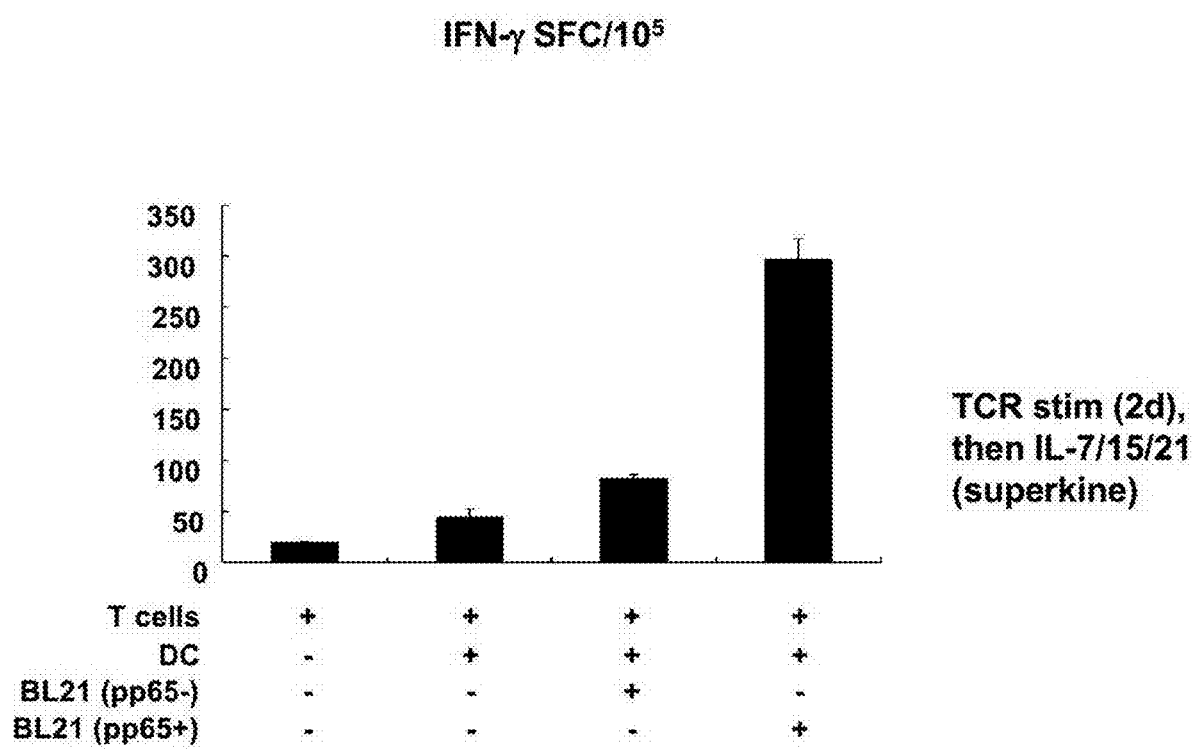
FIG. 42 is a graph showing enhanced antigen specific CD8 T cell responses in the presence of superkine (hIL7IL15//IL21/TxM fusion protein complex. T cells were selected from non-adherent PBMC, then cultured with a TCR stimulus (CD2/3/28 agonist Abs, 2 d), then washed of TCR stimulus, followed by culture with IL-7/15/21 superkine. After T cell expansion, T cells were added to autologous dendritic cells (DC), which were derived from the adherent fraction of PBMC. To the T/DC cultures were also added, nothing, BL21 E. coli expressing no pp65 (from CMV) or BL21 expressing pp65. Cultures were stimulated overnight, then ELISPOT developed to indicate the number of spot forming cells (IFN-γ producing)

The effect of hIL7/IL21/TxM on human NK cell expression of granzyme B was also assessed. Purified human NK cells ($4 \times 10^6$ cells/well) from 2 different donors were incubated in RPMI-10 medium with 50 nM hIL7/IL21/TxM, 50 nM ALT-803 or control media for 16 hours. The NK cells were then intracellularly stained with FITC-conjugated anti-granzyme B antibody and levels (MFI-mean fluorescent intensity) of granzyme B were analyzed by flow cytometry. Incubation in hIL7/IL21/TxM resulted in a 2.8 to 5.3-fold increase in granzyme B levels in NK cells whereas only modest increases (1.1 to 1.4-fold) were observed in ALT-803 treated NK cells. See FIG. 21. These findings further exemplify the ability of hIL7/IL21/TxM to enhance the cytotoxic potential of human NK cells.

Example 6: In Vitro and In Vivo Activity of IL-7/IL-21/TxM Complexes and Adoptive Cell Transfer of IL-7/IL-21/TxM-Stimulated Immune Cells on Senescent Cells and Senescent Cell- and Age-Related Pathologies As indicated above, accumulation of senescent cells in organs and tissues is associated with age-related diseases.

Methods have been developed to evaluate therapeutic strategies for reducing senescent cells and their associated pathologies in vitro and in vivo. To assess that activity of hIL7/IL21/TxM complexes, senescent cells will be generated in vitro through methods known in the art. Briefly, human diploid fibroblasts, IMR-90 and WI38 (ATCC, Manassas, Va., USA), human foreskin fibroblasts BJ (ATCC, Manassas, Va., USA) and primary human hepatic myofibroblasts (activated hepatic stellate (HS) cells) will be grown in standard conditions (i.e., DMEM supplemented with 10% FCS, 1% L-Glutamine and 1% penicillin-streptomycin and kept at 37° C. with 7.5% $CO_2$). DNA damage induced senescent (DIS) cells will be generated by treating growing cells with Etoposide (100 µM, Sigma) for 48 hours. Cells were considered senescent 7 days after Etoposide removal. Alternatively, oncogene induced senescence will be achieved by retroviral infection of IMR-90 cells with mCherry-H-Rasv12 (or mCherry as a control), and cells were considered senescent 9 days after the end of infection. IMR-90 cells can also be induced to senescence by treatment twice with 0.1 µM Doxorubicin with a 2-day interval and analyzed 7 days later. Such cells are representative of chemotherapy induced senescence. Senescent cells express elevated levels of beta-galactosidase which can be assayed as a immunohistochemical (IHC) biomarker to detect these cells in vitro and in tissues (Dimri et al., *Proc. Natl. Acad. Sci. USA.* 1995; 92, 9363-9367). Other detectable biomarkers of senescent cells include p16ink4a, IL-1α (early SASP factor) and IL-6 (late SASP factor) (Baar et al. *Cell.* 2017; 169, 132-47).

The cytotoxic activity of human NK cell lines (i.e., NK-92) and purified human NK cells against senescent cells will be assessed in vitro. Briefly, growing or DIS IMR-90 target cells (or growing or DIS WI38, BJ or HS cells) will plated in a 12-well plate at $5\times10^5$ per well; $10\times10^5$ NK-92 or purified NK cells will be subsequently added to each well. Following 2 hours of co-incubation, the non-adherent NK cells will be washed gently and cytotoxicity will be determined based on quantification of remaining adherent target cells using Presto Blue (Life Technologies, CA, USA) (or PI or crystal violet staining) according to the manufacturer's instructions. Based on published results (see for example, Sagiv, et al. *Oncogene* 2013; 32, 1971-1977), DIS cells are expected to be more sensitive than growing cells to NK cell-mediated cytotoxicity at a range of E:T ratios. To assess the effects of hIL7/IL21/TxM complexes on immune cell activity in this model, human NK cell lines (i.e., NK-92) and purified human NK cells will be incubated with various concentrations of hIL7/IL21/TxM complexes or IL-7, IL-21 and ALT-803 alone or in combination. The activated NK cells will then be co-incubated at various E:T ratios with growing or DIS target cells as described above and NK-mediated cytotoxicity against the DIS targets will be determined. It is anticipated that NK cells activated with hIL7/IL21/TxM complexes will exhibit more potent cytotoxicity against DIS cells that untreated NK cell controls. The selectivity of hIL7/IL21/TxM-treated NK cells against growing and DIS targets will also be evaluated. The results of these studies are anticipated to demonstrate that hIL7/IL21/TxM is an effective "senolytic" agent (defined as an agent that can reduce levels of senescent cells with minimal harm to normal cells). Additionally, hIL7/IL21/TxM-treated NK cells, including adoptively transferred cells, are expected to exhibit senolytic activity. Similar studies will be carried out with T cells to demonstrate the ability of hIL7/IL21/TxM complexes to stimulate immune responses against DIS target cells.

The effects of IL-7/IL-21/TxM complexes on senescent cell- and age-related diseases will be evaluated in animal models. It has previously shown the doxorubicin treatment induces senescence in mice resulting in reduced body weight, increased levels of senescent cells in the liver and decreased liver function as measured by elevated plasma levels of aspartate aminotransferase (AST) (Baar et al. *Cell.* 2017; 169, 132-47). To evaluate the effects of IL-7/IL-21/TxM complexes in this model, 10-40-week-old C57BL6 mice will be treated i.p. with 10 mg/kg doxorubicin on days 0 and 10 to induce senescence and liver damage. Untreated mice will serve as a control. The mice will then be treated with various doses of IL-7/IL-21/TxM complexes (mouse or human versions) or IL-7, IL-21 or ALT-803 alone or in combination. PBS will serve as a control treatment. The treatments will be given once or twice weekly by i.v. or s.c. routes starting on day 24. Body weights will be measured throughout the treatment period. On day 38, animals will be sacrificed and plasma AST levels will be assessed using an AST Activity Assay Kit (Sigma). Liver sections will also be evaluated for histology and the presence of senescent cells by IHC using the biomarkers described above. Treatment effects on immune cells (i.e., NK and T cells and subsets) will be assessed in blood, spleen and liver by flow cytometry using antibodies to detect specific immune cell subsets and activation/cytotoxicity markers and by methods to detect serum cytokine levels. Functional activity of treatment-stimulated immune cells (i.e., from blood or spleen) against senescent cells will be determined using the methods described above. Compared to the PBS control group, administration of IL-7/IL-21/TxM complexes is expected to reduce weight loss observed in mice following doxorubicin treatment. Levels of plasma AST and incidence of senescent cells and lesions in the liver are also expected to be reduced in doxorubicin-treated mice by IL-7/IL-21/TxM therapy. Corresponding activation of immune responses by IL-7/IL-21/TxM will provide evidence supporting the immune-mediated mechanism of action. Comparison of the treatment effects of IL-7/IL-21/TxM with IL-7, IL-21 or ALT-803 alone or in combination are expected to demonstrate the more potent anti-senescence activity of IL-7/IL-21/TxM therapy.

In addition to evaluation of direct IL-7/IL-21/TxM injection, the anti-senescence activity of adoptively transferred IL-7/IL-21/TxM-stimulated NK or T cells will be evaluated in the doxorubicin treated C57BL6 mouse model. In this study, mice will be treated with doxorubicin as described above and on day 24, NK or T cells that had been treated ex vivo with IL-7/IL-21/TxM complexes (mouse or human versions) or IL-7, IL-21 or ALT-803 alone or in combination will be adoptively transferred into the mice. Further treatment of the mice with IL-7/IL-21/TxM or cytokines may be carried out in some groups to provide cytokine support to the adoptively transferred cells. Treatment effects on immune responses, body weight and doxorubicin-induced liver senescence and damage will be assessed as described above. It is anticipated that adoptive transfer of IL-7/IL-21/TxM-stimulated NK or T cells will provide significant therapeutic benefit to mice with doxorubicin-induced senescence.

Further studies of IL-7/IL-21/TxM therapy and adoptive cell transfer of IL-7/IL-21/TxM-stimulated NK or T cells will be carried out in naturally aged mice. IL-7/IL-21/TxM complexes or IL-7, IL-21 or ALT-803 alone or in combination will be administered for up to 4 weeks as described above to 115-130-week-old (aged) or 26-week-old (young)

C57BL6 mice. Alternatively, the activity of adoptively transferred IL-7/IL-21/TxM-stimulated NK or T cells will be evaluated in aged and young mice as described above. Changes in body weight, fur density and responsiveness of the mice to stimuli will be assessed throughout the treatment period as describe previously (Baar et al. *Cell*. 2017; 169, 132-47). In addition, plasma levels of urea and creatinine will be measured with a QuantiChrom Urea Assay Kit (Gentaur) and Creatinine Assay Kit (Sigma), respectively, from samples collected before and after treatment as an assessment of age related loss of kidney function. Kidney sections will also be evaluated for the presence of senescent cells as described above. Compared to the PBS control group, administration of IL-7/IL-21/TxM complexes is expected to ameliorate age-related decreases in fur density and inactivity in aged mice. Levels of plasma urea and creatinine and incidence of senescent cells in the kidneys of aged mice are also expected to be reduced by IL-7/IL-21/TxM therapy. Similar therapeutic benefits are expected in aged mice receiving adoptively transferred IL-7/IL-21/TxM-stimulated NK or T cells. Together, the results of these studies are anticipated to show that treatment with IL-7/IL-21/TxM complex and adoptive cell transfer of IL-7/IL-21/TxM-stimulated NK or T cells exhibit senolytic activity in vivo and reduced senescent cell- and age-related pathologies.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated soluble fusion protein complex comprising at least two soluble proteins, wherein: a first soluble protein comprises a polypeptide according to SEQ ID NO:4, and a second soluble protein comprises a polypeptide according to SEQ ID NO:2, wherein the first and second soluble proteins are covalently linked by a disulfide bond to form the soluble fusion protein complex.

2. The soluble fusion protein complex of claim 1, wherein the first soluble protein consists of SEQ ID NO:4 and the second soluble protein consists of SEQ ID NO:2.

3. The soluble fusion protein complex of claim 1, wherein the first and/or second soluble protein are associated with a biologically active moiety.

4. The soluble fusion protein complex of claim 3, wherein the biologically active moiety comprises cytokines, antibodies, T cell receptors, receptor binding molecules, receptor domains, immune checkpoint agonists, immune checkpoint antagonists, chemokines, growth factors, toxins, cytotoxic agents, or combinations thereof.

5. The soluble fusion protein complex of claim 4, wherein the biologically active moiety comprises one or more cytokines.

6. The soluble fusion protein complex of claim 1, wherein the first soluble protein contains an Fc domain and is covalently linked to the second soluble protein by a disulfide bond linking the Fc domain of the first soluble protein to the Fc domain of the second soluble protein.

* * * * *

SEQUENCE LISTING

```
<160> NUMBER OF SEQ ID NOS: 4

<210> SEQ ID NO 1
<211> LENGTH: 1344
<212> TYPE: DNA
<213> ORGANISM: Homo sapiens

<400> SEQUENCE: 1
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc      180
gagtggtccg ccttctcctg ctttcagaag gcccagctga agtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tccatcacgt gtcctcctcc tatgtccgtg     480
gaacacgcag acatctgggt caagagctac agcttgtact ccagggagcg gtacatttgt     540
aactctggtt tcaagcgtaa agccggcacg tccagcctga cggagtgcgt gttgaacaag     600
gccacgaatg tcgcccactg gacaaccccc agtctcaaat gcattagaga gccgaaatct     660
tgtgacaaaa ctcacacatg cccaccgtgc ccagcacctg aactcctggg gggaccgtca     720
gtcttcctct ccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
```

```
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctcctgg taaa                                           1344
```

<210> SEQ ID NO 2
<211> LENGTH: 448
<212> TYPE: PRT
<213> ORGANISM: Homo sapiens

<400> SEQUENCE: 2

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                325                 330                 335
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 3
<211> LENGTH: 852
<212> TYPE: DNA
<213> ORGANISM: Homo sapiens

<400> SEQUENCE: 3
atgaagtggg tgaccttcat cagcctgctg ttcctgttct ccagcgccta ctccgattgc      60
gacatcgagg gcaaggacgg caagcagtac gagagcgtgc tgatggtgtc catcgaccag     120
ctgctggaca gcatgaagga gatcggctcc aactgcctca caacgagtt caacttcttc     180 aagcggcaca tctgcgacgc caacaaggag ggcatgttcc tgttcagggc cgccaggaaa     240
ctgcggcagt cctgaagat gaactccacc ggcgacttcg acctgcacct gctgaaggtg     300
tccgagggca ccaccatcct gctgaactgc accggacagg tgaagggccg aaacctgct      360 gctctgggag aggcccaacc caccaagagc ctggaggaga caagtccct gaaggagcag      420 aagaagctga cgacctgtg cttcctgaag aggctgctgc aggagatcaa gacctgctgg     480
aacaagatcc tgatgggcac caaggagcat aactgggtta cgtaataag tgatttgaaa     540 aaaattgaag atcttattca atctatgcat attgatgcta ctttatatac ggaaagtgat     600
gttcacccca gttgcaaagt aacagcaatg aagtgctttc tcttggagtt acaagttatt     660
tcacttgagt ccggagatgc aagtattcat gatacagtag aaaatctgat catcctagca     720
aacgacagtt tgtcttctaa tgggaatgta acagaatctg gatgcaaaga atgtgaggaa     780
ctggaggaaa aaaatattaa agaattttg cagagttttg tacatattgt ccaaatgttc      840
atcaacactt ct                                                         852

<210> SEQ ID NO 4
<211> LENGTH: 284
<212> TYPE: PRT
<213> ORGANISM: Homo sapiens

<400> SEQUENCE: 4

Met Lys Trp Val Thr Phe Ile Ser Leu Leu Phe Leu Phe Ser Ser Ala
1               5                  10                  15

Tyr Ser Asp Cys Asp Ile Glu Gly Lys Asp Gly Lys Gln Tyr Glu Ser
                20                  25                  30

Val Leu Met Val Ser Ile Asp Gln Leu Leu Asp Ser Met Lys Glu Ile
            35                  40                  45

Gly Ser Asn Cys Leu Asn Asn Glu Phe Asn Phe Phe Lys Arg His Ile
```

-continued

```
            50                  55                  60
Cys Asp Ala Asn Lys Glu Gly Met Phe Leu Phe Arg Ala Ala Arg Lys
65                      70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
                100                 105                 110

Gln Val Lys Gly Arg Lys Pro Ala Ala Leu Gly Glu Ala Gln Pro Thr
            115                 120                 125

Lys Ser Leu Glu Glu Asn Lys Ser Leu Lys Glu Gln Lys Lys Leu Asn
        130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Asn Trp Val Asn Val Ile
                165                 170                 175

Ser Asp Leu Lys Lys Ile Glu Asp Leu Ile Gln Ser Met His Ile Asp
                180                 185                 190

Ala Thr Leu Tyr Thr Glu Ser Asp Val His Pro Ser Cys Lys Val Thr
            195                 200                 205

Ala Met Lys Cys Phe Leu Leu Glu Leu Gln Val Ile Ser Leu Glu Ser
        210                 215                 220

Gly Asp Ala Ser Ile His Asp Thr Val Glu Asn Leu Ile Ile Leu Ala
225                 230                 235                 240

Asn Asp Ser Leu Ser Ser Asn Gly Asn Val Thr Glu Ser Gly Cys Lys
                245                 250                 255

Glu Cys Glu Glu Leu Glu Glu Lys Asn Ile Lys Glu Phe Leu Gln Ser
                260                 265                 270

Phe Val His Ile Val Gln Met Phe Ile Asn Thr Ser
            275                 280
```